US006905856B2

(12) United States Patent
Canfield et al.

(10) Patent No.: US 6,905,856 B2
(45) Date of Patent: Jun. 14, 2005

(54) SOLUBLE GLCNAC PHOSPHOTRANSFERASE

(75) Inventors: William Canfield, Oklahoma City, OK (US); Mariko Kudo, Oklahoma City, OK (US)

(73) Assignee: Genzyme Glycobiology Research Institute, Inc., Oklahoma City, OK (US)

( * ) Notice: Subject to any disclaimer, the term of this patent is extended or adjusted under 35 U.S.C. 154(b) by 0 days.

(21) Appl. No.: 10/023,888

(22) Filed: Dec. 21, 2001

(65) Prior Publication Data

US 2003/0119088 A1 Jun. 26, 2003

(51) Int. Cl.$^7$ ............................. C12N 9/12; C12N 9/14; C12P 21/06; C07H 21/04
(52) U.S. Cl. ...................... 435/194; 435/195; 435/68.1; 536/23.2
(58) Field of Search .......................... 435/194, 14, 195, 435/68.1; 536/23.2

(56) References Cited

U.S. PATENT DOCUMENTS

| | | |
|---|---|---|
| 3,957,578 A | 5/1976 | Narita et al. |
| 3,966,555 A | 6/1976 | Arnaud et al. |
| 3,972,777 A | 8/1976 | Yamada et al. |
| 4,140,107 A | 2/1979 | Lancee et al. |
| 4,156,013 A | 5/1979 | Bruinvels et al. |
| 4,195,126 A | 3/1980 | Hall |
| 4,328,215 A | 5/1982 | Bueding |
| 4,332,894 A | 6/1982 | Whistler |
| 4,401,662 A | 8/1983 | Lormeau et al. |
| 4,401,758 A | 8/1983 | Lormeau et al. |
| 4,431,737 A | 2/1984 | Olivieri et al. |
| 4,433,946 A | 2/1984 | Christianson et al. |
| 4,452,794 A | 6/1984 | Kort et al. |
| 4,474,770 A | 10/1984 | Lormeau et al. |
| 4,492,761 A | 1/1985 | Durack |
| 4,496,722 A | 1/1985 | Gallop et al. |
| 4,595,015 A | 6/1986 | Jansen et al. |
| 4,615,884 A | 10/1986 | Harshman |
| 4,639,420 A | 1/1987 | Schaffner |
| 4,659,817 A | 4/1987 | Gallop et al. |
| 4,749,570 A | 6/1988 | Poznansky |
| 4,798,169 A | 1/1989 | Rosen et al. |
| 4,851,390 A | 7/1989 | Morishige |
| 4,866,042 A | 9/1989 | Neuwelt |
| 4,975,441 A | 12/1990 | Gibson |
| 4,981,801 A | 1/1991 | Suzuki et al. |
| 4,986,274 A | 1/1991 | Stephens |
| 4,987,223 A | 1/1991 | Choay et al. |
| 4,997,760 A | 3/1991 | Hirabayashi et al. |
| 5,001,072 A | 3/1991 | Olson |
| 5,015,470 A | 5/1991 | Gibson ........................ 514/2 |
| 5,055,401 A | 10/1991 | Liljestroem et al. |
| 5,060,428 A | 10/1991 | Arthur, Jr. et al. ......... 52/125.6 |
| 5,075,231 A | 12/1991 | Moreau et al. ............. 435/198 |
| 5,077,200 A | 12/1991 | Habenstein ................. 435/14 |
| 5,082,778 A | 1/1992 | Overbeeke et al. ......... 435/208 |
| 5,089,392 A | 2/1992 | Miller et al. ................ 435/21 |
| 5,126,247 A | 6/1992 | Palmer et al. ............... 435/25 |
| 5,143,841 A | 9/1992 | Hirabayashi et al. ....... 435/227 |
| 5,166,320 A | 11/1992 | Wu et al. .................... 530/395 |
| 5,179,023 A | 1/1993 | Calhoun et al. ......... 435/235.1 |
| 5,202,253 A | 4/1993 | Esmon et al. |
| 5,205,917 A | 4/1993 | Klock, Jr. ................... 436/506 |
| 5,208,148 A | 5/1993 | Haugland et al. ........... 435/14 |
| 5,217,865 A | 6/1993 | Myerowitz ..................... 435/6 |
| 5,242,805 A | 9/1993 | Naleway et al. ............. 435/18 |
| 5,260,447 A | 11/1993 | Nakajima et al. ........... 548/222 |
| 5,281,394 A | 1/1994 | Holub ........................ 422/65 |
| 5,296,365 A | 3/1994 | Overbeeke et al. ......... 435/208 |
| 5,310,646 A | 5/1994 | Whitley ........................ 435/4 |
| 5,316,906 A | 5/1994 | Haugland et al. ............. 435/4 |
| 5,344,352 A | 9/1994 | Horne et al. ................ 445/24 |
| 5,356,804 A | 10/1994 | Desnick et al. |
| 5,362,628 A | 11/1994 | Haugland ..................... 435/18 |
| 5,366,883 A | 11/1994 | Asada et al. ................. 435/202 |
| 5,382,524 A | 1/1995 | Desnick et al. ............. 435/200 |
| 5,401,650 A | 3/1995 | Desnick et al. |
| 5,405,751 A | 4/1995 | Roncarolo .................. 435/7.24 |
| 5,420,112 A | 5/1995 | Lewis et al. ................. 514/12 |
| 5,433,946 A | 7/1995 | Allen, Jr. et al. .......... 424/94.3 |
| 5,439,935 A | 8/1995 | Rawlings et al. ........... 514/451 |
| 5,443,986 A | 8/1995 | Haughland et al. ........... 435/4 |
| 5,449,604 A | 9/1995 | Schellenberg et al. ......... 435/6 |
| 5,466,809 A | 11/1995 | Dime .......................... 546/183 |
| 5,475,095 A | 12/1995 | Myerowitz .................. 536/23.1 |
| 5,491,075 A | 2/1996 | Desnick et al. ............. 435/69.7 |
| 5,494,810 A | 2/1996 | Barany et al. ............. 435/91.52 |
| 5,501,957 A | 3/1996 | Dennis et al. ................ 435/15 |
| 5,512,471 A | 4/1996 | Smith .......................... 435/208 |
| 5,534,615 A | 7/1996 | Baker et al. ................ 530/350 |
| 5,545,402 A | 8/1996 | Watkinson ............... 424/94.63 |
| 5,554,366 A | 9/1996 | Rawlings et al. ......... 424/78.03 |

(Continued)

FOREIGN PATENT DOCUMENTS

WO 99/31117 6/1999

OTHER PUBLICATIONS

Sasaki, K., et al., Expression cloning of a novel alpha 2,3–sialyltransferase using lectin resistance selection. J. Biol. Chem., Oct. 1993, vol. 268, No. 30, pp. 22782–22787.
Michel, B., et al., Selection of an expression host for human glucocerebrosidase: importance of host cell glycosylation. UCLA Symposia on Molecular and Cellular Biology, 1990, vol. 111 (Glycobiology), pp. 159–172.
Stanley, P., et al., Selection and characterization of eight phenotypically distinct lines of lactin–resistant chinese hamster ovary cells. Cell, Oct. 1975, vol. 6, No. 2, pp. 121–128.

(Continued)

*Primary Examiner*—Elizabeth Slobodyansky
(74) *Attorney, Agent, or Firm*—Oblon, Spivak, McClelland, Maier & Neustadt, P.C.

(57) ABSTRACT

The present invention relates to a soluble GlcNAc phosphotransferase, a method of making the same and a method of phosphorylating with the same.

29 Claims, 9 Drawing Sheets

U.S. PATENT DOCUMENTS

| | | | |
|---|---|---|---|
| 5,565,362 A | 10/1996 | Rosen | 435/320.1 |
| 5,569,648 A | 10/1996 | Lewis et al. | 514/12 |
| 5,571,675 A | 11/1996 | Baker et al. | 435/6 |
| 5,571,893 A | 11/1996 | Baker et al. | 530/350 |
| 5,576,424 A | 11/1996 | Mao et al. | 536/17.9 |
| 5,578,479 A | 11/1996 | Laderman et al. | 435/202 |
| 5,580,757 A | 12/1996 | Desnick et al. | |
| 5,583,160 A | 12/1996 | Igarashi et al. | 514/669 |
| 5,585,247 A | 12/1996 | Habenstein | 435/18 |
| 5,612,206 A | 3/1997 | Valerio et al. | 435/456 |
| 5,621,106 A | 4/1997 | Dime | 546/183 |
| 5,624,806 A | 4/1997 | Baker et al. | 435/7.1 |
| 5,627,073 A | 5/1997 | Baker et al. | 435/331 |
| 5,627,171 A | 5/1997 | Park et al. | 514/114 |
| 5,633,228 A | 5/1997 | Lewis et al. | 514/12 |
| 5,633,261 A | 5/1997 | Dime | 514/299 |
| 5,635,383 A | 6/1997 | Wu et al. | |
| 5,639,607 A | 6/1997 | Desnick et al. | 435/6 |
| 5,639,939 A | 6/1997 | McCune, III | 800/11 |
| 5,648,229 A | 7/1997 | Habenstein | 435/18 |
| 5,648,335 A | 7/1997 | Lewis et al. | 514/12 |
| 5,658,567 A | 8/1997 | Calhoun et al. | 424/94.61 |
| 5,663,076 A | 9/1997 | Rostoker et al. | 438/14 |
| 5,663,254 A | 9/1997 | Lee et al. | 526/238.2 |
| 5,665,366 A | 9/1997 | Rawlings et al. | 424/401 |
| 5,679,545 A | 10/1997 | Baker et al. | 435/69.1 |
| 5,686,240 A | 11/1997 | Schuchman et al. | 435/6 |
| 5,691,181 A | 11/1997 | Lowe | 435/325 |
| 5,693,622 A | 12/1997 | Wolff et al. | 514/44 |
| 5,696,001 A | 12/1997 | Habenstein | 436/518 |
| 5,704,910 A | 1/1998 | Humes | 604/502 |
| 5,707,865 A | 1/1998 | Kohn et al. | 435/325 |
| 5,716,614 A | 2/1998 | Katz et al. | 424/94.3 |
| 5,719,031 A | 2/1998 | Haugland et al. | 435/7.4 |
| 5,721,367 A | 2/1998 | Kay et al. | 800/18 |
| 5,723,585 A | 3/1998 | Baker et al. | 530/413 |
| 5,728,381 A | 3/1998 | Wilson et al. | 424/94.6 |
| RE35,770 E | 4/1998 | Lormeau et al. | |
| 5,736,360 A | 4/1998 | Gaulton et al. | 435/69.1 |
| 5,741,957 A | 4/1998 | Deboer et al. | 800/7 |
| 5,750,172 A | 5/1998 | Meade et al. | 426/580 |
| 5,759,775 A | 6/1998 | Caras et al. | 435/6 |
| 5,773,236 A | 6/1998 | Diwu et al. | 435/15 |
| 5,773,278 A | 6/1998 | Schuchman et al. | |
| 5,792,647 A | 8/1998 | Roseman et al. | 435/252.3 |
| 5,798,239 A | 8/1998 | Wilson et al. | 435/183 |
| 5,798,366 A | 8/1998 | Platt et al. | |
| 5,798,448 A | 8/1998 | Caras et al. | 530/387.1 |
| 5,807,943 A | 9/1998 | Lee et al. | 526/238.2 |
| 5,830,711 A | 11/1998 | Barany et al. | 435/91.1 |
| 5,830,850 A | 11/1998 | Gelb et al. | 514/2 |
| 5,830,916 A | 11/1998 | Hannun et al. | 514/625 |
| 5,840,578 A | 11/1998 | Desnick et al. | 435/235 |
| 5,849,885 A | 12/1998 | Nuyens et al. | 530/416 |
| 5,851,782 A | 12/1998 | Hannun et al. | 435/7.71 |
| 5,854,207 A | 12/1998 | Lee et al. | 514/2 |
| 5,858,351 A | 1/1999 | Podsakoff et al. | 424/93.2 |
| 5,858,744 A | 1/1999 | Baum et al. | 435/183 |
| 5,858,755 A | 1/1999 | Lowe | 435/198 |
| 5,861,491 A | 1/1999 | Nuijens et al. | 530/417 |
| 5,871,946 A | 2/1999 | Lucas et al. | 435/18 |
| 5,874,297 A | 2/1999 | Wu et al. | 435/320.1 |
| 5,879,937 A | 3/1999 | Roncarolo | 435/235 |
| 5,895,833 A | 4/1999 | Berg | 800/18 |
| 5,906,817 A | 5/1999 | Moullier et al. | 424/93.21 |
| 5,911,704 A | 6/1999 | Humes | 604/93.01 |
| 5,912,146 A | 6/1999 | Nishimura et al. | 435/91.1 |
| 5,914,231 A | 6/1999 | Hennink et al. | 435/6 |
| 5,916,870 A | 6/1999 | Lee et al. | 514/2 |
| 5,916,911 A | 6/1999 | Shayman et al. | 514/428 |
| 5,917,122 A | 6/1999 | Byrne | 800/18 |
| 5,919,690 A | 7/1999 | Knap et al. | 435/208 |
| 5,919,913 A | 7/1999 | Nuyens et al. | 530/395 |
| 5,928,928 A | 7/1999 | Aerts | 435/201 |
| 5,929,036 A | 7/1999 | McEver | 514/25 |
| 5,929,304 A | 7/1999 | Radin et al. | |
| 5,932,211 A | 8/1999 | Wilson et al. | 424/94.6 |
| 5,939,279 A | 8/1999 | Smith et al. | 435/7.32 |
| 5,968,502 A | 10/1999 | Treco et al. | |
| 6,118,045 A | 9/2000 | Reuser et al. | 800/14 |

OTHER PUBLICATIONS

Do, H. et al., Human Mannose 6–Phosphate–uncovering Enzyme is Synthesized as a Proenzyme that is Activated by the Endoprotease Furin. Aug. 2002, J. Biol. Chem., vol. 277, No. 33, pp. 29737–29744.

Lee, W.S., "Multiple Signals Regulate Trafficking of the Mennose 6–Phosphute–uncovering Enayme", Feb. 2002, vol. 277, No. 5, pp. 3544–3551.

Alan D. Elbein et al, "Kifunenshine, A Potent Inhibitor of the Glycorprotein Processing, Mannosidase I", The Journal of Biological Chemistry, vol. 265, No. 26, Issue of Sep. 15, pp. 15599–I5605, 1990.

SLY, "The Missing Llink in Lysosomal Enzyme Targeting", The Journal of Clinical Investigation, vol. 105, No. 5, pp. 563–564, Mar. 2000.

Raas–Rothschild et al., "Molecular Basis of Variant Pseudo–Hurler Polydystrophy (Mucolipidosis IIIC)", The Journal of Clinical Investigation, vol. 105, No. 5, pp. 673–681, Mar. 2000.

Bao at aI., "Bovine Udp–N–Acetylglucosamine: Lysosoma-l–Enzyme N–Acetylglucosamine–1–Phosphotransferase", The Journal of Biological Chemistry, vol., 271, No. 49, pp. 31446–31451, Dec. 6, 1996.

Kornfield, "Purification and MuItimeric Structure of Bovine N–Acetylglucosamine–1–Phosphodiester α–N–AcetylgIu-cosaminidase", The Journal of Biological Chemistry, vol. 273, No. 36, pp. 23203–23210, Sep. 4, 1998.

Ke–Wei Zhao, et al., "Purification and characterization of human lymphoblast N–acetytglucosamine–1– phosphotransferase", Glycobiology. vol. 2, No. 2, pp. 119–125, 1992

Takahiro Nagase, et al., "Prediction of the Coding Sequences of Unidentified Human Genes. XV. The Complete Sequences of 100 New(cDNA Clones from Brain Which Code for Large Proteins in vitro", DNA Research, vol. 6, pp. :337–345. 1999.

XP–002226188, "KIAA1208 protein (Fragment)", From Takahiro Nagase, et al., "Prediction of the Coding Sequences of Unidentified Human Genes, XV, The Complete Sequences of 100 New(cDNA Clones from Brain Which Code for Large Proteins in vitro", DNA research, vol. 6, pp. 337–445, 1999.

XP–002226187, Basic domain/leucine zipper transcription factor (Fragment), From CORDES, et al., "The mouse segmentation gene kr encodes a novel basic domain–Ieucine zipper transcription factor" (1994), Cell, vol. 7, No. 9, pp. 1025–1034.

Karen Gheeslling Mullis, et al., "Purification and Kinetic Parameters of Bovine Liver N–Acetylglucosamine–1– phosphodiester alpha–N–AcetylglucosaminIdase", The Journal of Biological Chemistry, vol. 269, No. 3, Issue of Jan. 21, pp. 1718–1726, 1994.

Jin Kyu Lee, et al., "Purification and Characterization of Human Serum N–Acetylglucosamine–1–phosphodiester alpha–N–Acetylglucosaminidase", Archives of Biochemistry and Biophysics, vol. 319, No. 2. Jun. 1, pp. 413–425, 1995.

Theodore Page, et al., "Purification and characterization of human lymphoblast N–acetylglucosamine–1– phosphodiester alpha–N–acetylglucosaminidase", Glycobiology, vol. 6, No. 6, pp. 619–626, 1996.

Thomas J. Baranski, et al., "Lysosmal Enzyme Phosphorylation", The Journal of Biological Chemistry, vol. 267, No. 32, Issue of Nov. 15, pp. 23342–23348, 1992.

Ritva Tikkanen, et al., "Several cooperating binding sites mediate the interaction of a lysosomal enzyme with phosphotransferase", The EMBO Journal, vol. 16, No.22, pp. 6684.6693, 1997.

Fumito Matsuura et al., "Human alpha–galactosidase A: characterization of the N–linked oligosaccharides on the intracellular and secreted glycoforrms overexpressed by Chinese hamster ovary cells", Glycobiology, vol. 8, No. 4, pp. 329–339, 1998.

Shiroh Maguchi, et al., "Elevated Activity and Increased Mannose–6–phosphate in the Carbohydrate Moiety of Cathepsin D from Human Hepatoma[1]", Cancer Research, vol. 48, pp. 362–367, Jan. 15, 1988.

Norman W. Barton. et al., "Therapeutic response to intravenous infusions of glucocerebrosidase in a patient with Gaucher disease", Proc. Natl. Acad. Sci, USA, vol. 87, pp. 1913–1916, Mar. 1990.

R.O. Brady, et al., "Modifying Exogenous Glucocerebrosidase for Effective Replacement Therapy in Gaucher Disease", J. Inher. Metab. Dis., vol. 17, (1994), pp. 510–519.

Emil D. Kakkis, et al., "Overexpression of the Human Lysosomal Enzyme α–L–iduronidase in Chinese Hamster Ovary Cells", Protein Expression and Purification, vol. 5, (1994), pp. 225–252.

Ke–Wei, Zhao, et al., "Carbohydrate Structures of Recombinant Human α–L–Iduronldas Secreted by Chinese Hamster Ovary Cells", The Journal of Biological Chemistry, vol. 272, No. 36, Issue of Sep. 5, 1997, pp. 22758–22765.

Robin J. Ziegler, et al., "Correction of Enzymatic and Lysosomal Storage Defects in Fabry Mice by Adenovirus–Mediated Gene Transfer", Human Gene Therapy, vol. 10, pp. 1667–1682, (Jul. 1, 1999).

Huaichang Sun, "Retrovirus Vector–Mediated Correction and Cross–Correction of Lysosomal α–Mannosidase Deficiency in Human and Feline Fibroblasts", Human Gene Therapy, vol. 10, pp. 1311–1319, (May 20, 1999).

Ajj Reuser,, et al., "Lysosomal storage diseases: cellular pathology, clinical and genetic heterogeneity, therapy", Ann Biol Clin., vol. 52, (1994), pp. 721–728.

Database EST on STIC, GenBank accession No. BG291336, Strausberg, National Institutes of Health, Mammalian Gene Collection, Feb. 21, 2001 (Feb. 21, 2001), 567 bp that are 100% identical to nucleotides 3040–3598 of SEQ ID NO:1.

SEQUENCE LISTING

<160> NUMBER OF SEQ ID NOS: 38

<210> SEQ ID NO 1
<211> LENGTH: 3600
<212> TYPE: DNA
<213> ORGANISM: hybrid

<400> SEQUENCE: 1

```
atggagacag acacactcct gctatgggta ctgctgctct gggttccagg ttccactggt      60
gacgaagatc aggtagatcc gcggttaatc gacggtaagc ttagccgaga tcaataccat     120
gttttgtttg attcctatag agacaatatt gctggaaagt cctttcagaa tcggctttgt     180
ctgcccatgc cgattgacgt tgtttacacc tgggtgaatg gcacagatct tgaactactg     240
aaggaactac agcaggtcag agaacagatg gaggaggagc agaaagcaat gagagaaatc     300
cttgggaaaa acacaacgga acctactaag aagagtgaga agcagttaga gtgtttgcta     360
acacactgca ttaaggtgcc aatgcttgtc ctggacccag ccctgccagc caacatcacc     420
ctgaaggacc tgccatctct ttatccttct tttcattctg ccagtgacat tttcaatgtt     480
gcaaaaccaa aaaaccttc taccaatgtc tcagttgttg tttttgacag tactaaggat     540
gttgaagatg cccactctgg actgcttaaa ggaaatagca gacagacagt atggagggc     600 tacttgacaa cagataaaga agtccctgga ttagtgctaa tgcaagattt ggctttcctg     660
agtggatttc caccaacatt caaggaaaca aatcaactaa aaacaaaatt gccagaaaat     720
ctttcctcta aagtcaaact gttgcagttg tattcagagg ccagtgtagc gcttctaaaa     780
ctgaataacc ccaaggattt tcaagaattg aataagcaaa ctaagaagaa catgaccatt     840
gatggaaaag aactgaccat aagtcctgca tatttattat gggatctgag cgccatcagc     900
cagtctaagc aggatgaaga catctctgcc agtcgttttg aagataacga agaactgagg     960
tactcattgc gatctatcga gaggcatgca ccatgggttc ggaatatttt cattgtcacc    1020
aacgggcaga ttccatcctg gctgaacctt gacaatcctc gagtgacaat agtaacacac    1080
caggatgttt ttcgaaattt gagccacttg cctaccttta gttcacctgc tattgaaagt    1140
cacgttcatc gcatcgaagg gctgtcccag aagtttattt acctaaatga tgatgtcatg    1200
tttgggaagg atgtctggcc agatgatttt tacagtcact ccaaaggcca gaaggtttat    1260
ttgacatggc ctgtgccaaa ctgtgccgag ggctgcccag gttcctggat taaggatggc    1320
tattgtgaca aggcttgtaa taattcagcc tgcgattggg atggtgggga ttgctctgga    1380
aacagtggag ggagtcgcta tattgcagga ggtgaggta ctgggagtat tggagttgga    1440
```

-continued

```
cagccctggc agtttggtgg aggaataaac agtgtctctt actgtaatca gggatgtgcg    1500
aattcctggc tcgctgataa gttctgtgac caagcatgca atgtcttgtc ctgtgggttt    1560
gatgctggcg actgtgggca agatcatttt catgaattgt ataaagtgat ccttctccca    1620
aaccagactc actatattat tccaaaaggt gaatgcctgc cttatttcag ctttgcagaa    1680
gtagccaaaa gaggagttga aggtgcctat agtgacaatc caataattcg acatgcttct    1740
attgccaaca agtggaaaac catccacctc ataatgcaca gtggaatgaa tgccaccaca    1800
atacatttta atctcacgtt tcaaaataca acgatgaag  agttcaaaat gcagataaca    1860
gtggaggtgg acacaaggga gggaccaaaa ctgaattcta cggcccagaa gggttacgaa    1920
aatttagtta gtcccataac acttcttcca gaggcggaaa tccttttttga ggatattccc    1980 aaagaaaaac gcttcccgaa gtttaagaga catgatgtta actcaacaag gagagcccag    2040
gaagaggtga aaattcccct ggtaaatatt tcactccttc caaagacgc  ccagttgagt    2100 ctcaatacct tggatttgca actggaacat ggagacatca ctttgaaagg atacaatttg    2160
tccaagtcag ccttgctgag atcatttctg atgaactcac agcatgctaa ataaaaaat     2220 caagctataa taacagatga aacaaatgac agtttggtgg ctccacagga aaaacaggtt    2280
cataaaagca tcttgccaaa cagcttagga gtgtctgaaa gattgcagag gttgactttt    2340
cctgcagtga gtgtaaaagt gaatggtcat gaccagggtc agaatccacc cctggacttg    2400
gagaccacag caagatttag agtggaaact cacacccaaa aaaccatagg cggaaatgtg    2460 acaaagaaa  agcccccatc tctgattgtt ccactgaaa  gccagatgac aaaagaaaag    2520 aaatcacag  ggaaagaaaa agagaacagt agaatggagg aaaatgctga aaatcacata    2580
ggcgttactg aagtgttact tggaagaaag ctgcagcatt acacagatag ttacttgggc    2640
tttttgccat gggagaaaaa aaagtatttc ctagatcttc tcgacgaaga agagtcattg    2700
aagacacaat tggcctactt cactgatagc aagaatagag ccagatacaa gagagataca    2760
tttgcagatt ccctcagata tgtaaataaa attctaaata gcaagtttgg attcacatcg    2820
cggaaagtcc ctgctcacat gcctcacatg attgaccgga ttgttatgca agaactgcaa    2880
gatatgttcc ctgaagaatt tgacaagacg tcatttcaca aagtgcgcca ttctgaggat    2940
atgcagtttg ccttctctta ttttttattat ctcatgagtg cagtgcagcc actgaatata    3000
tctcaagtct ttgatgaagt tgatacagat caatctggtg tcttgtctga cagagaaatc    3060
cgaacactgg ctaccagaat tcacgaactg ccgttaagtt tgcaggattt gacaggtctg    3120
gaacacatgc taataaattg ctcaaaaatg cttcctgctg atatcacgca gctaaataat    3180
attccaccaa ctcaggaatc ctactatgat cccaacctgc caccggtcac taaaagtcta    3240
gtaacaaact gtaaaccagt aactgacaaa atccacaaag catataagga caaaaacaaa    3300
tataggtttg aaatcatggg agaagaagaa atcgctttta aaatgattcg taccaacgtt    3360
tctcatgtgg ttggccagtt ggatgacata agaaaaaacc ctaggaagtt tgtttgcctg    3420
aatgacaaca ttgaccacaa tcataaagat gctcagacag tgaaggctgt tctcagggac    3480
ttctatgaat ccatgttccc cataccttcc caatttgaac tgccaagaga gtatcgaaac    3540
cgtttccttc atatgcatga gctgcaggaa tggagggctt atcgagacaa attgaagtag    3600
```

<210> SEQ ID NO 2
<211> LENGTH: 1199
<212> TYPE: PRT
<213> ORGANISM: hybrid

```
<400> SEQUENCE: 2

Met Glu Thr Asp Thr Leu Leu Leu Trp Val Leu Leu Leu Trp Val Pro
1               5                   10                  15

Gly Ser Thr Gly Asp Glu Asp Gln Val Asp Pro Arg Leu Ile Asp Gly
                20                  25                  30

Lys Leu Ser Arg Asp Gln Tyr His Val Leu Phe Asp Ser Tyr Arg Asp
            35                  40                  45

Asn Ile Ala Gly Lys Ser Phe Gln Asn Arg Leu Cys Leu Pro Met Pro
        50                  55                  60

Ile Asp Val Val Tyr Thr Trp Val Asn Gly Thr Asp Leu Glu Leu Leu
65                  70                  75                  80

Lys Glu Leu Gln Gln Val Arg Glu Gln Met Glu Glu Glu Gln Lys Ala
                85                  90                  95

Met Arg Glu Ile Leu Gly Lys Asn Thr Thr Glu Pro Thr Lys Lys Ser
                100                 105                 110

Glu Lys Gln Leu Glu Cys Leu Leu Thr His Cys Ile Lys Val Pro Met
            115                 120                 125

Leu Val Leu Asp Pro Ala Leu Pro Ala Asn Ile Thr Leu Lys Asp Leu
        130                 135                 140

Pro Ser Leu Tyr Pro Ser Phe His Ser Ala Ser Asp Ile Phe Asn Val
145                 150                 155                 160

Ala Lys Pro Lys Asn Pro Ser Thr Asn Val Ser Val Val Phe Asp
                165                 170                 175

Ser Thr Lys Asp Val Glu Asp Ala His Ser Gly Leu Leu Lys Gly Asn
                180                 185                 190

Ser Arg Gln Thr Val Trp Arg Gly Tyr Leu Thr Thr Asp Lys Glu Val
            195                 200                 205

Pro Gly Leu Val Leu Met Gln Asp Leu Ala Phe Leu Ser Gly Phe Pro
        210                 215                 220

Pro Thr Phe Lys Glu Thr Asn Gln Leu Lys Thr Lys Leu Pro Glu Asn
225                 230                 235                 240

Leu Ser Ser Lys Val Lys Leu Leu Gln Leu Tyr Ser Glu Ala Ser Val
                245                 250                 255

Ala Leu Leu Lys Leu Asn Asn Pro Lys Asp Phe Gln Glu Leu Asn Lys
            260                 265                 270

Gln Thr Lys Lys Asn Met Thr Ile Asp Gly Lys Glu Leu Thr Ile Ser
        275                 280                 285

Pro Ala Tyr Leu Leu Trp Asp Leu Ser Ala Ile Ser Gln Ser Lys Gln
        290                 295                 300

Asp Glu Asp Ile Ser Ala Ser Arg Phe Glu Asp Asn Glu Glu Leu Arg
305                 310                 315                 320

Tyr Ser Leu Arg Ser Ile Glu Arg His Ala Pro Trp Val Arg Asn Ile
                325                 330                 335

Phe Ile Val Thr Asn Gly Gln Ile Pro Ser Trp Leu Asn Leu Asp Asn
            340                 345                 350

Pro Arg Val Thr Ile Val Thr His Gln Asp Val Phe Arg Asn Leu Ser
        355                 360                 365

His Leu Pro Thr Phe Ser Ser Pro Ala Ile Glu Ser His Val His Arg
        370                 375                 380

Ile Glu Gly Leu Ser Gln Lys Phe Ile Tyr Leu Asn Asp Asp Val Met
385                 390                 395                 400

Phe Gly Lys Asp Val Trp Pro Asp Asp Phe Tyr Ser His Ser Lys Gly
                405                 410                 415
```

```
Gln Lys Val Tyr Leu Thr Trp Pro Val Pro Asn Cys Ala Glu Gly Cys
            420                 425                 430

Pro Gly Ser Trp Ile Lys Asp Gly Tyr Cys Asp Lys Ala Cys Asn Asn
            435                 440                 445

Ser Ala Cys Asp Trp Asp Gly Gly Asp Cys Ser Gly Asn Ser Gly Gly
    450                 455                 460

Ser Arg Tyr Ile Ala Gly Gly Gly Thr Gly Ser Ile Gly Val Gly
465                 470                 475                 480

Gln Pro Trp Gln Phe Gly Gly Gly Ile Asn Ser Val Ser Tyr Cys Asn
                485                 490                 495

Gln Gly Cys Ala Asn Ser Trp Leu Ala Asp Lys Phe Cys Asp Gln Ala
            500                 505                 510

Cys Asn Val Leu Ser Cys Gly Phe Asp Ala Gly Asp Cys Gly Gln Asp
            515                 520                 525

His Phe His Glu Leu Tyr Lys Val Ile Leu Pro Asn Gln Thr His
    530                 535                 540

Tyr Ile Ile Pro Lys Gly Glu Cys Leu Pro Tyr Phe Ser Phe Ala Glu
545                 550                 555                 560

Val Ala Lys Arg Gly Val Gly Ala Tyr Ser Asp Asn Pro Ile Ile
                565                 570                 575

Arg His Ala Ser Ile Ala Asn Lys Trp Lys Thr Ile His Leu Ile Met
            580                 585                 590

His Ser Gly Met Asn Ala Thr Thr Ile His Phe Asn Leu Thr Phe Gln
            595                 600                 605

Asn Thr Asn Asp Glu Glu Phe Lys Met Gln Ile Thr Val Glu Val Asp
    610                 615                 620

Thr Arg Glu Gly Pro Lys Leu Asn Ser Thr Ala Gln Lys Gly Tyr Glu
625                 630                 635                 640

Asn Leu Val Ser Pro Ile Thr Leu Leu Pro Glu Ala Glu Ile Leu Phe
                645                 650                 655

Glu Asp Ile Pro Lys Glu Lys Arg Phe Pro Lys Phe Lys Arg His Asp
            660                 665                 670

Val Asn Ser Thr Arg Arg Ala Gln Glu Glu Val Lys Ile Pro Leu Val
    675                 680                 685

Asn Ile Ser Leu Leu Pro Lys Asp Ala Gln Leu Ser Leu Asn Thr Leu
    690                 695                 700

Asp Leu Gln Leu Glu His Gly Asp Ile Thr Leu Lys Gly Tyr Asn Leu
705                 710                 715                 720

Ser Lys Ser Ala Leu Leu Arg Ser Phe Leu Met Asn Ser Gln His Ala
                725                 730                 735

Lys Ile Lys Asn Gln Ala Ile Ile Thr Asp Glu Thr Asn Asp Ser Leu
            740                 745                 750

Val Ala Pro Gln Glu Lys Gln Val His Lys Ser Ile Leu Pro Asn Ser
    755                 760                 765

Leu Gly Val Ser Glu Arg Leu Gln Arg Leu Thr Phe Pro Ala Val Ser
    770                 775                 780

Val Lys Val Asn Gly His Asp Gln Gly Gln Asn Pro Pro Leu Asp Leu
785                 790                 795                 800

Glu Thr Thr Ala Arg Phe Arg Val Glu Thr His Thr Gln Lys Thr Ile
                805                 810                 815

Gly Gly Asn Val Thr Lys Glu Lys Pro Pro Ser Leu Ile Val Pro Leu
            820                 825                 830
```

-continued

Glu Ser Gln Met Thr Lys Glu Lys Lys Ile Thr Gly Lys Glu Lys Glu
            835                 840                 845

Asn Ser Arg Met Glu Glu Asn Ala Glu Asn His Ile Gly Val Thr Glu
        850                 855                 860

Val Leu Leu Gly Arg Lys Leu Gln His Tyr Thr Asp Ser Tyr Leu Gly
865                 870                 875                 880

Phe Leu Pro Trp Glu Lys Lys Tyr Phe Leu Asp Leu Asp Glu
                    885                 890                 895

Glu Glu Ser Leu Lys Thr Gln Leu Ala Tyr Phe Thr Asp Ser Lys Asn
                900                 905                 910

Arg Ala Arg Tyr Lys Arg Asp Thr Phe Ala Asp Ser Leu Arg Tyr Val
            915                 920                 925

Asn Lys Ile Leu Asn Ser Lys Phe Gly Phe Thr Ser Arg Lys Val Pro
        930                 935                 940

Ala His Met Pro His Met Ile Asp Arg Ile Val Met Gln Glu Leu Gln
945                 950                 955                 960

Asp Met Phe Pro Glu Glu Phe Asp Lys Thr Ser Phe His Lys Val Arg
                    965                 970                 975

His Ser Glu Asp Met Gln Phe Ala Phe Ser Tyr Phe Tyr Leu Met
            980                 985                 990

Ser Ala Val Gln Pro Leu Asn Ile Ser Gln Val Phe Asp Glu Val Asp
        995                 1000                1005

Thr Asp Gln Ser Gly Val Leu Ser Asp Arg Glu Ile Arg Thr Leu
    1010                1015                1020

Ala Thr Arg Ile His Glu Leu Pro Leu Ser Leu Gln Asp Leu Thr
    1025                1030                1035

Gly Leu Glu His Met Leu Ile Asn Cys Ser Lys Met Leu Pro Ala
    1040                1045                1050

Asp Ile Thr Gln Leu Asn Asn Ile Pro Pro Thr Gln Glu Ser Tyr
    1055                1060                1065

Tyr Asp Pro Asn Leu Pro Pro Val Thr Lys Ser Leu Val Thr Asn
    1070                1075                1080

Cys Lys Pro Val Thr Asp Lys Ile His Lys Ala Tyr Lys Asp Lys
    1085                1090                1095

Asn Lys Tyr Arg Phe Glu Ile Met Gly Glu Glu Ile Ala Phe
    1100                1105                1110

Lys Met Ile Arg Thr Asn Val Ser His Val Val Gly Gln Leu Asp
    1115                1120                1125

Asp Ile Arg Lys Asn Pro Arg Lys Phe Val Cys Leu Asn Asp Asn
    1130                1135                1140

Ile Asp His Asn His Lys Asp Ala Gln Thr Val Lys Ala Val Leu
    1145                1150                1155

Arg Asp Phe Tyr Glu Ser Met Phe Pro Ile Pro Ser Gln Phe Glu
    1160                1165                1170

Leu Pro Arg Glu Tyr Arg Asn Arg Phe Leu His Met His Glu Leu
    1175                1180                1185

Gln Glu Trp Arg Ala Tyr Arg Asp Lys Leu Lys
    1190                1195

<210> SEQ ID NO 3
<211> LENGTH: 5597
<212> TYPE: DNA
<213> ORGANISM: Homo sapiens

<400> SEQUENCE: 3

-continued

```
cggagccgag cgggcgtccg tcgccggagc tgcaatgagc ggcgcccgga ggctgtgacc      60
tgcgcgcggc ggcccgaccg ggcccctga atggcggctc gctgaggcgg cggcggcggc     120
ggcggctcag gctcctcggg gcgtggcgtg gcggtgaagg ggtgatgctg ttcaagctcc     180
tgcagagaca aacctatacc tgcctgtccc acaggtatgg gctctacgtg tgcttcttgg     240
gcgtcgttgt caccatcgtc tccgccttcc agttcggaga ggtggttctg gaatggagcc     300
gagatcaata ccatgttttg tttgattcct atagagacaa tattgctgga aagtcctttc     360
agaatcggct ttgtctgccc atgccgattg acgttgttta cacctgggtg aatggcacag     420
atcttgaact actgaaggaa ctacagcagg tcagagaaca gatggaggag gagcagaaag     480
caatgagaga aatccttggg aaaaacacaa cggaacctac taagaagagt gagaagcagt     540
tagagtgttt gctaacacac tgcattaagg tgccaatgct tgtactggac ccagccctgc     600
cagccaacat caccctgaag gacgtgccat ctctttatcc ttcttttcat tctgccagtg     660
acattttcaa tgttgcaaaa ccaaaaaacc cttctaccaa tgtctcagtt gttgtttttg     720
acagtactaa ggatgttgaa gatgcccact ctggactgct taaggaaat agcagacaga     780
cagtatggag ggggtacttg acaacagata agaagtccc tggattagtg ctaatgcaag     840
atttggcttt cctgagtgga tttccaccaa cattcaagga aacaaatcaa ctaaaaacaa     900
aattgccaga aaatctttcc tctaaagtca actgttgca gttgtattca gaggccagtg     960
tagcgcttct aaaactgaat aaccccaagg attttcaaga attgaataag caaactaaga    1020
agaacatgac cattgatgga aaagaactga ccataagtcc tgcatattta ttatgggatc    1080
tgagcgccat cagccagtct aagcaggatg aagacatctc tgccagtcgt tttgaagata    1140
acgaagaact gaggtactca ttgcgatcta tcgagaggca tgcaccatgg gttcggaata    1200
ttttcattgt caccaacggg cagattccat cctggctgaa ccttgacaat cctcgagtga    1260
caatagtaac acaccaggat gttttttcgaa atttgagcca cttgcctacc tttagttcac    1320
ctgctattga aagtcacatt catcgcatcg aagggctgtc ccagaagttt atttacctaa    1380
atgatgatgt catgtttggg aaggatgtct ggccagatga ttttacagt cactccaaag    1440
gccagaaggt ttatttgaca tggcctgtgc caaactgtgc cgagggctgc ccaggttcct    1500
ggattaagga tggctattgt gacaaggctt gtaataattc agcctgcgat tgggatggtg    1560
gggattgctc tggaaacagt ggagggagtc gctatattgc aggaggtgga ggtactggga    1620
gtattggagt tggacacccc tggcagtttg gtggaggaat aaacagtgtc tcttactgta    1680
atcagggatg tgcgaattcc tggctcgctg ataagttctg tgaccaagca tgcaatgtct    1740
tgtcctgtgg gttgatgct ggcgactgtg gcaagatca ttttcatgaa ttgtataaag    1800
tgatccttct cccaaaccag actcactata ttattccaaa aggtgaatgc ctgccttatt    1860
tcagctttgc agaagtagcc aaaagaggag ttgaaggtgc ctatagtgac aatccaataa    1920
ttcgacatgc ttctattgcc aacaagtgga aaaccatcca cctcataatg cacagtggaa    1980
tgaatgccac cacaatacat tttaatctca cgtttcaaaa tacaaacgat gaagagttca    2040
aaatgcagat aacagtggag gtggacacaa gggagggacc aaaactgaat tctacggccc    2100
agaagggtta cgaaaattta gttagtccca taacacttct tccagaggcg gaaatccttt    2160
ttgaggatat tcccaaagaa aaacgcttcc cgaagtttaa gagacatgat gttaactcaa    2220
caaggagagc ccaggaagag gtgaaaattc cctggtaaaa tatttcactc cttccaaaag    2280
acgcccagtt gagtctcaat accttggatt tgcaactgga acatggagac atcactttga    2340
```

```
aaggatacaa tttgtccaag tcagccttgc tgagatcatt tctgatgaac tcacagcatg    2400
ctaaaataaa aaatcaagct ataataacag atgaaacaaa tgacagtttg gtggctccac    2460
aggaaaaaca ggttcataaa agcatcttgc caaacagctt aggagtgtct gaaagattgc    2520
agaggttgac ttttcctgca gtgagtgtaa aagtgaatgg tcatgaccag ggtcagaatc    2580 caccccctgga cttggagacc acagcaagat ttagagtgga aactcacacc caaaaaacca    2640
taggcggaaa tgtgacaaaa gaaaagcccc catctctgat tgttccactg gaaagccaga    2700
tgacaaaaga aaagaaaatc acagggaaag aaaaagagaa cagtagaatg gaggaaaatg    2760
ctgaaaatca cataggcgtt actgaagtgt tacttggaag aaagctgcag cattacacag    2820
atagttactt gggcttttttg ccatgggaga aaaaaaagta tttccaagat cttctcgacg    2880
aagaagagtc attgaagaca caattggcat acttcactga tagcaaaaat actgggaggc    2940
aactaaaaga tacatttgca gattccctca gatatgtaaa taaaattcta aatagcaagt    3000
ttggattcac atcgcggaaa gtccctgctc acatgcctca catgattgac cggattgtta    3060
tgcaagaact gcaagatatg ttccctgaag aatttgacaa gacgtcattt cacaaagtgc    3120
gccattctga ggatatgcag tttgccttct cttattttta ttatctcatg agtgcagtgc    3180
agccactgaa tatatctcaa gtctttgatg aagttgatac agatcaatct ggtgtcttgt    3240
ctgacagaga aatccgaaca ctggctacca gaattcacga actgccgtta agtttgcagg    3300
atttgacagg tctggaacac atgctaataa attgctcaaa aatgcttcct gctgatatca    3360
cgcagctaaa taatattcca ccaactcagg aatcctacta tgatcccaac ctgccaccgg    3420
tcactaaaag tctagtaaca aactgtaaac cagtaactga caaaatccac aaagcatata    3480
aggacaaaaa caaatatagg tttgaaatca tgggagaaga agaaatcgct tttaaaatga    3540
ttcgtaccaa cgtttctcat gtggttggcc agttggatga cataagaaaa aaccctagga    3600
agtttgtttg cctgaatgac aacattgacc acaatcataa agatgctcag acagtgaagg    3660
ctgttctcag ggacttctat gaatccatgt tccccatacc ttcccaattt gaactgccaa    3720
gagagtatcg aaaccgtttc cttcatatgc atgagctgca ggaatggagg gcttatcgag    3780
acaaattgaa gttttggacc cattgtgtac tagcaacatt gattatgttt actatattct    3840 catttttttgc tgagcagtta attgcactta agcggaagat atttcccaga aggaggatac    3900
acaaagaagc tagtcccaat cgaatcagag tatagaagat cttcatttga aaaccatcta    3960
cctcagcatt tactgagcat tttaaaactc agcttcacag agatgtcttt gtgatgtgat    4020
gcttagcagt ttggcccgaa gaaggaaaat atccagtacc atgctgtttt gtggcatgaa    4080
tatagcccac tgactaggaa ttatttaacc aacccactga aaacttgtgt gtcgagcagc    4140
tctgaactga ttttactttt aaagaatttg ctcatggacc tgtcatcctt tttataaaaa    4200
ggctcactga caagagacag ctgttaattt cccacagcaa tcattgcaga ctaactttat    4260
taggagaagc ctatgccagc tgggagtgat tgctaagagg ctccagtctt tgcattccaa    4320
agccttttgc taaagttttg cactttttttt ttttcatttc ccatttttaa gtagttacta    4380
agttaactag ttattcttgc ttctgagtat aacgaattgg gatgtctaaa cctattttta    4440
tagatgttat ttaaataatg cagcaatatc acctcttatt gacaatacct aaattatgag    4500 tttttattaat atttaagact gtaaatggtc ttaaaccact aactactgaa gagctcaatg    4560
attgacatct gaaatgcttt gtaattattg acttcagccc ctaagaatgc tatgatttca    4620
cgtgcaggtc taatttcaac aggctagagt tagtactact taccagatgt aattatgttt    4680
tggaaatgta catattcaaa cagaagtgcc tcatttttaga aatgagtagt gctgatggca    4740
```

-continued

```
ctggcacatt acagtggtgt cttgtttaat actcattggt atattccagt agctatctct    4800
ctcagttggt ttttgataga acagaggcca gcaaactttc tttgtaaaag gctggttagt    4860
aaattattgc aggccacctg tgtctttgtc atacattctt cttgctgttg tttagtttgt    4920
ttttttttcaa acaaccctct aaaaatgtaa aaaccatgtt tagcttgcag ctgtacaaaa   4980
actgcccacc agccagatgt gaccctcagg ccatcatttg ccaatcactg agaattattt    5040
ttgttgttgt tgttgttgtt gttttttgaga cagagtctct ctctgttgcc caggctggag   5100
tgcagtggcg caatctcagc tcactgcaac ctccgcctcc cgggttcaag cagttctgtc    5160
tcagccttct gagtagctgg gactacaggt gcatgccacc acccctgct aattttttgta   5220
tttttagtag agacgggggt tccaccatat tggtcaggct tatcttgaac tcctgacctc    5280
aggtgatcca cctgcctctg cctcccaaag tgctgagatt acaggcataa gccagtgcac    5340
ccagccgaga attagtattt ttatgtatgg ttaaaccttg gcgtctagcc atattttatg    5400
tcataataca atggatttgt gaagagcaga ttccatgagt aactctgaca ggtatttag     5460
atcatgatct caacaatatt cctcccaaat ggcatacatc ttttgtacaa agaacttgaa    5520
atgtaaatac tgtgtttgtg ctgtaagagt tgtgtatttc aaaaactgaa atctcataaa    5580
aagttaaatt ttgaaaa                                                    5597
```

<210> SEQ ID NO 4
<211> LENGTH: 928
<212> TYPE: PRT
<213> ORGANISM: Homo sapiens

<400> SEQUENCE: 4

```
Met Leu Phe Lys Leu Leu Gln Arg Gln Thr Tyr Thr Cys Leu Ser His
1               5                   10                  15

Arg Tyr Gly Leu Tyr Val Cys Phe Leu Gly Val Val Thr Ile Val
            20                  25                  30

Ser Ala Phe Gln Phe Gly Glu Val Val Leu Glu Trp Ser Arg Asp Gln
        35                  40                  45

Tyr His Val Leu Phe Asp Ser Tyr Arg Asp Asn Ile Ala Gly Lys Ser
    50                  55                  60

Phe Gln Asn Arg Leu Cys Leu Pro Met Pro Ile Asp Val Val Tyr Thr
65                  70                  75                  80

Trp Val Asn Gly Thr Asp Leu Glu Leu Leu Lys Glu Leu Gln Gln Val
                85                  90                  95

Arg Glu Gln Met Glu Glu Gln Lys Ala Met Arg Glu Ile Leu Gly
            100                 105                 110

Lys Asn Thr Thr Glu Pro Thr Lys Lys Ser Lys Gln Leu Glu Cys
            115                 120                 125

Leu Leu Thr His Cys Ile Lys Val Pro Met Leu Val Leu Asp Pro Ala
    130                 135                 140

Leu Pro Ala Asn Ile Thr Leu Lys Asp Val Pro Ser Leu Tyr Pro Ser
145                 150                 155                 160

Phe His Ser Ala Ser Asp Ile Phe Asn Val Ala Lys Pro Lys Asn Pro
                165                 170                 175

Ser Thr Asn Val Ser Val Val Phe Asp Ser Thr Lys Asp Val Glu
            180                 185                 190

Asp Ala His Ser Gly Leu Leu Lys Gly Asn Ser Arg Gln Thr Val Trp
        195                 200                 205

Arg Gly Tyr Leu Thr Thr Asp Lys Glu Val Pro Gly Leu Val Leu Met
```

-continued

```
            210                 215                 220
Gln Asp Leu Ala Phe Leu Ser Gly Phe Pro Thr Phe Lys Glu Thr
225                 230                 235                 240

Asn Gln Leu Lys Thr Lys Leu Pro Glu Asn Leu Ser Ser Lys Val Lys
                245                 250                 255

Leu Leu Gln Leu Tyr Ser Glu Ala Ser Val Ala Leu Leu Lys Leu Asn
                260                 265                 270

Asn Pro Lys Asp Phe Gln Glu Leu Asn Lys Gln Thr Lys Lys Asn Met
            275                 280                 285

Thr Ile Asp Gly Lys Glu Leu Thr Ile Ser Pro Ala Tyr Leu Leu Trp
290                 295                 300

Asp Leu Ser Ala Ile Ser Gln Ser Lys Gln Asp Glu Asp Ile Ser Ala
305                 310                 315                 320

Ser Arg Phe Glu Asp Asn Glu Glu Leu Arg Tyr Ser Leu Arg Ser Ile
                325                 330                 335

Glu Arg His Ala Pro Trp Val Arg Asn Ile Phe Ile Val Thr Asn Gly
                340                 345                 350

Gln Ile Pro Ser Trp Leu Asn Leu Asp Asn Pro Arg Val Thr Ile Val
            355                 360                 365

Thr His Gln Asp Val Phe Arg Asn Leu Ser His Leu Pro Thr Phe Ser
370                 375                 380

Ser Pro Ala Ile Glu Ser His Ile His Arg Ile Glu Gly Leu Ser Gln
385                 390                 395                 400

Lys Phe Ile Tyr Leu Asn Asp Asp Val Met Phe Gly Lys Asp Val Trp
                405                 410                 415

Pro Asp Asp Phe Tyr Ser His Ser Lys Gly Gln Lys Val Tyr Leu Thr
                420                 425                 430

Trp Pro Val Pro Asn Cys Ala Glu Gly Cys Pro Gly Ser Trp Ile Lys
            435                 440                 445

Asp Gly Tyr Cys Asp Lys Ala Cys Asn Asn Ser Ala Cys Asp Trp Asp
450                 455                 460

Gly Gly Asp Cys Ser Gly Asn Ser Gly Gly Ser Arg Tyr Ile Ala Gly
465                 470                 475                 480

Gly Gly Gly Thr Gly Ser Ile Gly Val Gly His Pro Trp Gln Phe Gly
                485                 490                 495

Gly Gly Ile Asn Ser Val Ser Tyr Cys Asn Gln Gly Cys Ala Asn Ser
            500                 505                 510

Trp Leu Ala Asp Lys Phe Cys Asp Gln Ala Cys Asn Val Leu Ser Cys
            515                 520                 525

Gly Phe Asp Ala Gly Asp Cys Gly Gln Asp His Phe His Glu Leu Tyr
530                 535                 540

Lys Val Ile Leu Leu Pro Asn Gln Thr His Tyr Ile Ile Pro Lys Gly
545                 550                 555                 560

Glu Cys Leu Pro Tyr Phe Ser Phe Ala Glu Val Ala Lys Arg Gly Val
                565                 570                 575

Glu Gly Ala Tyr Ser Asp Asn Pro Ile Ile Arg His Ala Ser Ile Ala
                580                 585                 590

Asn Lys Trp Lys Thr Ile His Leu Ile Met His Ser Gly Met Asn Ala
            595                 600                 605

Thr Thr Ile His Phe Asn Leu Thr Phe Gln Asn Thr Asn Asp Glu Glu
610                 615                 620

Phe Lys Met Gln Ile Thr Val Glu Val Asp Thr Arg Glu Gly Pro Lys
625                 630                 635                 640
```

-continued

Leu Asn Ser Thr Ala Gln Lys Gly Tyr Glu Asn Leu Val Ser Pro Ile
            645                 650                 655

Thr Leu Leu Pro Glu Ala Glu Ile Leu Phe Glu Asp Ile Pro Lys Glu
            660                 665                 670

Lys Arg Phe Pro Lys Phe Lys Arg His Asp Val Asn Ser Thr Arg Arg
            675                 680                 685

Ala Gln Glu Glu Val Lys Ile Pro Leu Val Asn Ile Ser Leu Leu Pro
        690                 695                 700

Lys Asp Ala Gln Leu Ser Leu Asn Thr Leu Asp Leu Gln Leu Glu His
705                 710                 715                 720

Gly Asp Ile Thr Leu Lys Gly Tyr Asn Leu Ser Lys Ser Ala Leu Leu
                725                 730                 735

Arg Ser Phe Leu Met Asn Ser Gln His Ala Lys Ile Lys Asn Gln Ala
                740                 745                 750

Ile Ile Thr Asp Glu Thr Asn Asp Ser Leu Val Ala Pro Gln Glu Lys
            755                 760                 765

Gln Val His Lys Ser Ile Leu Pro Asn Ser Leu Gly Val Ser Glu Arg
        770                 775                 780

Leu Gln Arg Leu Thr Phe Pro Ala Val Ser Val Lys Val Asn Gly His
785                 790                 795                 800

Asp Gln Gly Gln Asn Pro Pro Leu Asp Leu Glu Thr Thr Ala Arg Phe
                805                 810                 815

Arg Val Glu Thr His Thr Gln Lys Thr Ile Gly Gly Asn Val Thr Lys
                820                 825                 830

Glu Lys Pro Pro Ser Leu Ile Val Pro Leu Glu Ser Gln Met Thr Lys
            835                 840                 845

Glu Lys Lys Ile Thr Gly Lys Glu Lys Glu Asn Ser Arg Met Glu Glu
        850                 855                 860

Asn Ala Glu Asn His Ile Gly Val Thr Glu Val Leu Leu Gly Arg Lys
865                 870                 875                 880

Leu Gln His Tyr Thr Asp Ser Tyr Leu Gly Phe Leu Pro Trp Glu Lys
                885                 890                 895

Lys Lys Tyr Phe Gln Asp Leu Leu Asp Glu Glu Ser Leu Lys Thr
            900                 905                 910

Gln Leu Ala Tyr Phe Thr Asp Ser Lys Asn Thr Gly Arg Gln Leu Lys
        915                 920                 925

<210> SEQ ID NO 5
<211> LENGTH: 328
<212> TYPE: PRT
<213> ORGANISM: Homo sapiens

<400> SEQUENCE: 5

Asp Thr Phe Ala Asp Ser Leu Arg Tyr Val Asn Lys Ile Leu Asn Ser
1               5                   10                  15

Lys Phe Gly Phe Thr Ser Arg Lys Val Pro Ala His Met Pro His Met
            20                  25                  30

Ile Asp Arg Ile Val Met Gln Glu Leu Gln Asp Met Phe Pro Glu Glu
        35                  40                  45

Phe Asp Lys Thr Ser Phe His Lys Val Arg His Ser Glu Asp Met Gln
    50                  55                  60

Phe Ala Phe Ser Tyr Phe Tyr Leu Met Ser Ala Val Gln Pro Leu
65                  70                  75                  80

Asn Ile Ser Gln Val Phe Asp Glu Val Asp Thr Asp Gln Ser Gly Val

```
                    85                  90                  95
Leu Ser Asp Arg Glu Ile Arg Thr Leu Ala Thr Arg Ile His Glu Leu
                100                 105                 110
Pro Leu Ser Leu Gln Asp Leu Thr Gly Leu Glu His Met Leu Ile Asn
            115                 120                 125
Cys Ser Lys Met Leu Pro Ala Asp Ile Thr Gln Leu Asn Asn Ile Pro
        130                 135                 140
Pro Thr Gln Glu Ser Tyr Tyr Asp Pro Asn Leu Pro Pro Val Thr Lys
145                 150                 155                 160
Ser Leu Val Thr Asn Cys Lys Pro Val Thr Asp Lys Ile His Lys Ala
                165                 170                 175
Tyr Lys Asp Lys Asn Lys Tyr Arg Phe Glu Ile Met Gly Glu Glu Glu
            180                 185                 190
Ile Ala Phe Lys Met Ile Arg Thr Asn Val Ser His Val Val Gly Gln
        195                 200                 205
Leu Asp Asp Ile Arg Lys Asn Pro Arg Lys Phe Val Cys Leu Asn Asp
    210                 215                 220
Asn Ile Asp His Asn His Lys Asp Ala Gln Thr Val Lys Ala Val Leu
225                 230                 235                 240
Arg Asp Phe Tyr Glu Ser Met Phe Pro Ile Pro Ser Gln Phe Glu Leu
                245                 250                 255
Pro Arg Glu Tyr Arg Asn Arg Phe Leu His Met His Glu Leu Gln Glu
            260                 265                 270
Trp Arg Ala Tyr Arg Asp Lys Leu Lys Phe Trp Thr His Cys Val Leu
        275                 280                 285
Ala Thr Leu Ile Met Phe Thr Ile Phe Ser Phe Phe Ala Glu Gln Leu
    290                 295                 300
Ile Ala Leu Lys Arg Lys Ile Phe Pro Arg Arg Ile His Lys Glu
305                 310                 315                 320
Ala Ser Pro Asn Arg Ile Arg Val
                325

<210> SEQ ID NO 6
<211> LENGTH: 1219
<212> TYPE: DNA
<213> ORGANISM: Homo sapiens

<400> SEQUENCE: 6
gtagagcgca ggtgcgcggc tcgatggcgg cggggctggc gcggctcctg ttgctcctcg      60
ggctctcggc cggcgggccc gcgccggcag gtgcagcgaa gatgaaggtg gtggaggagc     120
ccaacgcgtt tggggtgaac aacccgttct tgcctcaggc cagtcgcctc caggccaaga     180
gggatccttc acccgtgtct ggacccgtgc atctcttccg actctcgggc aagtgcttca     240
gcctggtgga gtccacgtac aagtatgagt tctgcccgtt ccacaacgtg acccagcacg     300
agcagacctt ccgctggaac gcctacagtg ggatcctcgg catctggcac gagtgggaga     360
tcgccaacaa caccttcacg ggcatgtgga tgagggacgg tgacgcctgc cgttcccgga     420
gccggcagag caaggtggag ctggcgtgtg aaaaagcaa ccggctggcc catgtgtccg     480
agccgagcac ctgcgtctat gcgctgacgt cgagacccc cctcgtctgc caccccacg      540
ccttgctagt gtacccaacc ctgccagagg ccctgcagcg gcagtgggac caggtagagc     600
aggacctggc cgatgagctg atcaccccc agggccatga agttgctg aggacacttt       660
ttgaggatgc tggctactta aagaccccag aagaaaatga acccacccag ctggagggag     720
```

-continued

```
gtcctgacag cttggggttt gagaccctgg aaaactgcag gaaggctcat aaagaactct    780
caaaggagat caaaaggctg aaaggtttgc tcacccagca cggcatcccc tacacgaggc    840
ccacagaaac ttccaacttg gagcacttgg ccacgagac gcccagagcc aagtctccag     900
agcagctgcg gggtgaccca ggactgcgtg ggagtttgtg accttgtggt gggagagcag    960
aggtggacgc ggccgagagc cctacagaga agctggctgg taggacccgc aggaccagct   1020
gaccaggctt gtgctcagag aagcagacaa aacaaagatt caaggtttta attaattccc   1080
atactgataa aaataactcc atgaattctg taaaccattg cataaatgct atagtgtaaa   1140
aaaatttaaa caagtgttaa ctttaaacag ttcgctacaa gtaaatgatt ataaatacta   1200
aaaaaaaaaa aaaaaaaa                                                 1219
```

<210> SEQ ID NO 7
<211> LENGTH: 305
<212> TYPE: PRT
<213> ORGANISM: Homo sapiens

<400> SEQUENCE: 7

```
Met Ala Ala Gly Leu Ala Arg Leu Leu Leu Leu Gly Leu Ser Ala
1               5                  10                  15

Gly Gly Pro Ala Pro Ala Gly Ala Ala Lys Met Lys Val Val Glu Glu
            20                  25                  30

Pro Asn Ala Phe Gly Val Asn Asn Pro Phe Leu Pro Gln Ala Ser Arg
        35                  40                  45

Leu Gln Ala Lys Arg Asp Pro Ser Pro Val Ser Gly Pro Val His Leu
    50                  55                  60

Phe Arg Leu Ser Gly Lys Cys Phe Ser Leu Val Glu Ser Thr Tyr Lys
65                  70                  75                  80

Tyr Glu Phe Cys Pro Phe His Asn Val Thr Gln His Glu Gln Thr Phe
                85                  90                  95

Arg Trp Asn Ala Tyr Ser Gly Ile Leu Gly Ile Trp His Glu Trp Glu
            100                 105                 110

Ile Ala Asn Asn Thr Phe Thr Gly Met Trp Met Arg Asp Gly Asp Ala
        115                 120                 125

Cys Arg Ser Arg Ser Arg Gln Ser Lys Val Glu Leu Ala Cys Gly Lys
    130                 135                 140

Ser Asn Arg Leu Ala His Val Ser Glu Pro Ser Thr Cys Val Tyr Ala
145                 150                 155                 160

Leu Thr Phe Glu Thr Pro Leu Val Cys His Pro His Ala Leu Leu Val
                165                 170                 175

Tyr Pro Thr Leu Pro Glu Ala Leu Gln Arg Gln Trp Asp Gln Val Glu
            180                 185                 190

Gln Asp Leu Ala Asp Glu Leu Ile Thr Pro Gln Gly His Glu Lys Leu
        195                 200                 205

Leu Arg Thr Leu Phe Glu Asp Ala Gly Tyr Leu Lys Thr Pro Glu Glu
    210                 215                 220

Asn Glu Pro Thr Gln Leu Glu Gly Gly Pro Asp Ser Leu Gly Phe Glu
225                 230                 235                 240

Thr Leu Glu Asn Cys Arg Lys Ala His Lys Glu Leu Ser Lys Glu Ile
                245                 250                 255

Lys Arg Leu Lys Gly Leu Leu Thr Gln His Gly Ile Pro Tyr Thr Arg
            260                 265                 270

Pro Thr Glu Thr Ser Asn Leu Glu His Leu Gly His Glu Thr Pro Arg
        275                 280                 285
```

Ala Lys Ser Pro Glu Gln Leu Arg Gly Asp Pro Gly Leu Arg Gly Ser
    290                 295                 300

Leu
305

<210> SEQ ID NO 8
<211> LENGTH: 5229
<212> TYPE: DNA
<213> ORGANISM: Mus musculus

<400> SEQUENCE: 8

| | | | | | |
|---|---|---|---|---|---|
| ggcggtgaag | gggtgatgct | gttcaagctc | ctgcagagac | agacctatac | ctgcctatcc | 60 |
| cacaggtatg | ggctctacgt | ctgcttcgtg | ggcgtcgttg | tcaccatcgt | ctcggctttc | 120 |
| cagttcggag | aggtggttct | ggaatggagc | cgagatcagt | accatgtttt | gtttgattcc | 180 |
| tacagagaca | acattgctgg | gaaatccttt | cagaatcggc | tctgtctgcc | catgccaatc | 240 |
| gacgtggttt | acacctgggt | gaatggcact | gaccttgaac | tgctaaagga | gctacagcag | 300 |
| gtccgagagc | acatggagga | agagcagaga | gccatgcggg | aaaccctcgg | aagaacaca | 360 |
| accgaaccga | caaagaagag | tgagaagcag | ctggaatgtc | tgctgacgca | ctgcattaag | 420 |
| gtgcccatgc | ttgttctgga | cccggccctg | ccagccacca | tcaccctgaa | ggatctgcca | 480 |
| acccttacc | catctttcca | cgcgtccagc | gacatgttca | atgttgcgaa | accaaaaaat | 540 |
| ccgtctacaa | atgtccccgt | tgtcgttttt | gacactacta | aggatgttga | agacgcccat | 600 |
| gctggaccgt | ttaagggagg | ccagcaaaca | gatgtttgga | gagcctactt | gacaacagac | 660 |
| aaagacgccc | ctggcttagt | gctgatacaa | ggcttggcgt | tcctgagtgg | attcccaccg | 720 |
| accttcaagg | agacgagtca | actgaagaca | agctgccaa | gaaagctttt | ccctctaaaa | 780 |
| ataaagctgt | tgcggctgta | ctcggaggcc | agtgtcgctc | ttctgaaatt | gaataatccc | 840 |
| aagggttttcc | aagagctgaa | caagcagacc | aagaagaaca | tgaccatcga | tgggaaggaa | 900 |
| ctgaccatca | gccctgcgta | tctgctgtgg | gacctgagtg | ccatcagcca | gtccaagcag | 960 |
| gatgaggacg | cgtctgccag | ccgctttgag | gataatgaag | agctgaggta | ctcgctgcga | 1020 |
| tctatcgaga | gacacgcgcc | atgggtacgg | aatattttca | ttgtcaccaa | cgggcagatt | 1080 |
| ccatcctggc | tgaaccttga | caaccctcga | gtgaccatag | tgacccacca | ggacattttc | 1140 |
| caaaatctga | gccacttgcc | tactttcagt | tcccctgcta | ttgaaagtca | cattcaccgc | 1200 |
| atcgaagggc | tgtcccagaa | gtttatttat | ctaaatgacg | atgtcatgtt | cggtaaggac | 1260 |
| gtctggccgg | acgattttta | cagccactcc | aaaggtcaaa | aggtttattt | gacatggcct | 1320 |
| gtgccaaact | gtgcagaggg | ctgcccgggc | tcctggataa | aggacggcta | ttgtgataag | 1380 |
| gcctgtaata | cctcaccctg | tgactgggat | ggcggaaact | gctctggtaa | tactgcaggg | 1440 |
| aaccggtttg | ttgcaagagg | tgggggtacc | gggaatattg | gagctggaca | gcactggcag | 1500 |
| tttggtggag | gaataaacac | catctcttac | tgtaaccaag | gatgtgcaaa | ctcctggctg | 1560 |
| gctgacaagt | tctgtgacca | gcctgtaac | gtcttatcct | gcgggtttga | tgctggtgac | 1620 |
| tgtggacaag | atcattttca | tgaattgtat | aaagtaacac | ttctcccaaa | ccagactcac | 1680 |
| tatgttgtcc | ccaaaggtga | atacctgtct | tatttcagct | ttgcaaacat | agccagaaaa | 1740 |
| agaattgaag | ggacctacag | cgacaacccc | atcatccgcc | acgcgtccat | tgcaaacaag | 1800 |
| tggaaaaccc | tacacctgat | aatgcccggg | gggatgaacg | ccaccacgat | ctatttttaac | 1860 |
| ctcactcttc | aaaacgccaa | cgacgaagag | ttcaagatcc | agatagcagt | agaggtggac | 1920 |

-continued

```
acgagggagg cgcccaaact gaattctaca acccagaagg cctatgaaag tttggttagc    1980
ccagtgacac ctcttcctca ggctgacgtc ccttttgaag atgtccccaa agagaaacgc    2040
ttccccaaga tcaggagaca tgatgtaaat gcaacaggga gattccaaga ggaggtgaaa    2100
atccccgggg taaatatttc actccttccc aaagaggccc aggtgaggct gagcaacttg    2160
gatttgcaac tagaacgtgg agacatcact ctgaaaggat ataacttgtc caagtcagcc    2220
ctgctaaggt ctttcctggg gaattcacta gatactaaaa taaaacctca agctaggacc    2280
gatgaaacaa aaggcaacct ggaggtccca caggaaaacc cttctcacag acgtccacat    2340
ggctttgctg gtgaacacag atcagagaga tggactgccc cagcagagac agtgaccgtg    2400
aaaggccgtg accacgcttt gaatccaccc ccggtgttgg agaccaatgc aagattggcc    2460
cagcctacac taggcgtgac tgtgtccaaa gagaaccttt caccgctgat cgttcccca    2520 gaaagccact tgccaaaaga agaggagagt gacagggcag aaggcaatgc tgtacctgta    2580
aaggagttag tgcctggcag acggttgcag cagaattatc caggctttt gccctgggag    2640 aaaaaaaagt atttccaaga ccttcttgat gaggaagagt cattgaagac ccagttggcg    2700
tactttacag accgcaaaca taccggggagg caactaaaag atacatttgc agactccctc    2760
cgatacgtca ataaaattct caacagcaag tttggattca catccaggaa agtccctgca    2820
cacatgccgc acatgattga caggatcgtt atgcaagaac tccaagatat gttccctgaa    2880
gaatttgaca agacttcatt tcacaaggtg cgtcactctg aggacatgca gtttgccttc    2940
tcctactttt attacctcat gagtgcagtt cagcccctca atatttccca agtctttcat    3000
gaagtagaca cagaccaatc tggtgtcttg tctgataggg aaatccgaac wctggccacg    3060
agaattcacg acctaccttt aagcttgcag gatttgacag gtttggaaca catgttaata    3120
aattgctcaa aaatgctccc cgctaatatc actcaactca caacatccc accgactcag    3180 gaagcatact acgaccccaa cctgcctccg gtcactaaga gtcttgtcac caactgtaag    3240
ccagtaactg acaagatcca caaagcctat aaagacaaga acaaatacag gtttgaaatc    3300
atgggagagg aagaaatcgc tttcaagatg atacgaacca atgtttctca tgtggttggt    3360
cagttggatg acatcagaaa aaaccccagg aagttcgttt gtctgaatga caacattgac    3420
cacaaccata aagatgcccg gacagtgaag gctgtcctca gggacttcta tgagtccatg    3480
tttcccatac cttcccagtt tgagctgcca agagagtatc ggaaccgctt tctgcacatg    3540
catgagctcc aagaatggcg ggcatatcga gacaagctga agttttggac ccactgcgta    3600
ctagcaacgt tgattatatt tactatattc tcatttttg ctgaacagat aattgctctg    3660
aagcgaaaga tatttcccag gaggaggata cacaaagaag ctagtccaga ccgaatcagg    3720
gtgtagaaga tcttcatttg aaagtcacct accttagcat ctgtgaacat ctccctcctc    3780
gacaccacag cggagtccct gtgatgtggc acagaggcag cctcgtgggg agaagggaca    3840
tcgtgcagac cgggttcttc tgcaatggga agagagccca ctgacctgga attattcagc    3900
acactaagaa cctgtgtcaa tagcttgtac agcttgtact tttaaaggat ttgccgaagg    3960
acctgtcggc ttgttgacaa accctccctg acaagctgct ggtttcttcc cccagttact    4020
gcagactgag aaaccagtcc atcttgaaag caagtgcgga ggggcccag tctttgcatt    4080 ccaaagcttt ccagcataat ttctggcttg tctcctcctt tgatccattt ccatttttt    4140 tttaaaaaac aataagtggc tactaagtta gtcattctca cttctcaaaa taacaaatca    4200
ggatgtcaaa acatttgtat agatcttatt taaataatat agaacgatta cttctttagc    4260
ctatctaaat tattgatttt tattaacagt caagtggtct tgaaccgcta acaactactg    4320
```

-continued

```
aagagctcga gattgacgtt gaaagtgctt tgagcttgtt taactcattc cccaagaata    4380
ctgtgacctc gtgtgcgggc ctgattgcga agggctagtg tcacgtagca gtgctgctca    4440
ccggatgtaa ttatgtcgtg gaaatgtaca tacagacaaa agtgcctcac ttcagaaatg    4500
agtagtgctg atggcaccag cgagtgatgg tgtccatttg gaaacccatg ataccttcca    4560
atgcccaccc tgcttacttt atacagagca ggggttaacc aacttctgtc aaagaacagt    4620
aaagaacttg agatacatcc atctttgtca aatagttttc cttgctaaca tttattattg    4680
ttggtgtttt gggaggttta ttttatttta ttgctttgtt attttttcaag acggggattc    4740 tctgtgtagc tctggctgtt tggtaattca ctctaaagac caggctggcc ttgaacttag    4800
agattcacct gcttctgctt cctgaatggt aggacatgtg cccacattgc ctacccaccc    4860
cccttttggg ggggtgagc aactcaataa aaagatgaaa acctgcttta gtttgcagct    4920
atacaaaagc agcaggcctc agccagactt gaccccgggg gccattgttg cccacggga    4980 gaatcatttt tgacgtgggt aagcaaaccc tgatattggt catgctgtgt tatgtcatta    5040
tgtggtggtt ttgaattttg gaagatattt tcagtcatga tttcagtagt attcctccaa    5100
aatggcacac attttgtaa taagaacttg aaatgtaaat attgtgtttg tgctgtaaat    5160
tttgtgtatt tcaaaaactg aagtttcata aaaaaacaca cttattggaa aaaaaaaaa    5220 aaaaaaaaa                                                          5229
```

<210> SEQ ID NO 9
<211> LENGTH: 908
<212> TYPE: PRT
<213> ORGANISM: Mus musculus

<400> SEQUENCE: 9

```
Met Leu Phe Lys Leu Leu Gln Arg Gln Thr Tyr Thr Cys Leu Ser His
1               5                   10                  15

Arg Tyr Gly Leu Tyr Val Cys Phe Gly Val Val Thr Ile Val
                20                  25                  30

Ser Ala Phe Gln Phe Gly Glu Val Val Leu Glu Trp Ser Arg Asp Gln
            35                  40                  45

Tyr His Val Leu Phe Asp Ser Tyr Arg Asp Asn Ile Ala Gly Lys Ser
        50                  55                  60

Phe Gln Asn Arg Leu Cys Leu Pro Met Pro Ile Asp Val Val Tyr Thr
65                  70                  75                  80

Trp Val Asn Gly Thr Asp Leu Glu Leu Leu Lys Glu Leu Gln Gln Val
                85                  90                  95

Arg Glu His Met Glu Glu Glu Gln Arg Ala Met Arg Glu Thr Leu Gly
                100                 105                 110

Lys Asn Thr Thr Glu Pro Thr Lys Lys Ser Glu Lys Gln Leu Glu Cys
            115                 120                 125

Leu Leu Thr His Cys Ile Lys Val Pro Met Leu Val Leu Asp Pro Ala
        130                 135                 140

Leu Pro Ala Thr Ile Thr Leu Lys Asp Leu Pro Thr Leu Tyr Pro Ser
145                 150                 155                 160

Phe His Ala Ser Ser Asp Met Phe Asn Val Ala Lys Pro Lys Asn Pro
                165                 170                 175

Ser Thr Asn Val Pro Val Val Phe Asp Thr Thr Lys Asp Val Glu
            180                 185                 190

Asp Ala His Ala Gly Pro Phe Lys Gly Gly Gln Thr Asp Val Trp
        195                 200                 205
```

-continued

```
Arg Ala Tyr Leu Thr Thr Asp Lys Asp Ala Pro Gly Leu Val Leu Ile
    210                 215                 220
Gln Gly Leu Ala Phe Leu Ser Gly Phe Pro Pro Thr Phe Lys Glu Thr
225                 230                 235                 240
Ser Gln Leu Lys Thr Lys Leu Pro Arg Lys Ala Phe Pro Leu Lys Ile
                245                 250                 255
Lys Leu Leu Arg Leu Tyr Ser Glu Ala Ser Val Ala Leu Leu Lys Leu
            260                 265                 270
Asn Asn Pro Lys Gly Phe Gln Glu Leu Asn Lys Gln Thr Lys Lys Asn
        275                 280                 285
Met Thr Ile Asp Gly Lys Glu Leu Thr Ile Ser Pro Ala Tyr Leu Leu
    290                 295                 300
Trp Asp Leu Ser Ala Ile Ser Gln Ser Lys Gln Asp Glu Asp Ala Ser
305                 310                 315                 320
Ala Ser Arg Phe Glu Asp Asn Glu Glu Leu Arg Tyr Ser Leu Arg Ser
                325                 330                 335
Ile Glu Arg His Ala Pro Trp Val Arg Asn Ile Phe Ile Val Thr Asn
            340                 345                 350
Gly Gln Ile Pro Ser Trp Leu Asn Leu Asp Asn Pro Arg Val Thr Ile
        355                 360                 365
Val Thr His Gln Asp Ile Phe Gln Asn Leu Ser His Leu Pro Thr Phe
    370                 375                 380
Ser Ser Pro Ala Ile Glu Ser His Ile His Arg Ile Glu Gly Leu Ser
385                 390                 395                 400
Gln Lys Phe Ile Tyr Leu Asn Asp Asp Val Met Phe Gly Lys Asp Val
                405                 410                 415
Trp Pro Asp Asp Phe Tyr Ser His Ser Lys Gly Gln Lys Val Tyr Leu
            420                 425                 430
Thr Trp Pro Val Pro Asn Cys Ala Glu Gly Cys Pro Gly Ser Trp Ile
        435                 440                 445
Lys Asp Gly Tyr Cys Asp Lys Ala Cys Asn Thr Ser Pro Cys Asp Trp
    450                 455                 460
Asp Gly Gly Asn Cys Ser Gly Asn Thr Ala Gly Asn Arg Phe Val Ala
465                 470                 475                 480
Arg Gly Gly Gly Thr Gly Asn Ile Gly Ala Gly Gln His Trp Gln Phe
                485                 490                 495
Gly Gly Gly Ile Asn Thr Ile Ser Tyr Cys Asn Gln Gly Cys Ala Asn
            500                 505                 510
Ser Trp Leu Ala Asp Lys Phe Cys Asp Gln Ala Cys Asn Val Leu Ser
        515                 520                 525
Cys Gly Phe Asp Ala Gly Asp Cys Gly Gln Asp His Phe His Glu Leu
    530                 535                 540
Tyr Lys Val Thr Leu Leu Pro Asn Gln Thr His Tyr Val Val Pro Lys
545                 550                 555                 560
Gly Glu Tyr Leu Ser Tyr Phe Ser Phe Ala Asn Ile Ala Arg Lys Arg
                565                 570                 575
Ile Glu Gly Thr Tyr Ser Asp Asn Pro Ile Ile Arg His Ala Ser Ile
            580                 585                 590
Ala Asn Lys Trp Lys Thr Leu His Leu Ile Met Pro Gly Gly Met Asn
        595                 600                 605
Ala Thr Thr Ile Tyr Phe Asn Leu Thr Leu Gln Asn Ala Asn Asp Glu
    610                 615                 620
```

```
Glu Phe Lys Ile Gln Ile Ala Val Glu Val Asp Thr Arg Glu Ala Pro
625                 630                 635                 640

Lys Leu Asn Ser Thr Thr Gln Lys Ala Tyr Glu Ser Leu Val Ser Pro
            645                 650                 655

Val Thr Pro Leu Pro Gln Ala Asp Val Pro Phe Glu Asp Val Pro Lys
                660                 665                 670

Glu Lys Arg Phe Pro Lys Ile Arg Arg His Asp Val Asn Ala Thr Gly
            675                 680                 685

Arg Phe Gln Glu Glu Val Lys Ile Pro Arg Val Asn Ile Ser Leu Leu
690                 695                 700

Pro Lys Glu Ala Gln Val Arg Leu Ser Asn Leu Asp Leu Gln Leu Glu
705                 710                 715                 720

Arg Gly Asp Ile Thr Leu Lys Gly Tyr Asn Leu Ser Lys Ser Ala Leu
                725                 730                 735

Leu Arg Ser Phe Leu Gly Asn Ser Leu Asp Thr Lys Ile Lys Pro Gln
                740                 745                 750

Ala Arg Thr Asp Glu Thr Lys Gly Asn Leu Glu Val Pro Gln Glu Asn
            755                 760                 765

Pro Ser His Arg Arg Pro His Gly Phe Ala Gly Glu His Arg Ser Glu
770                 775                 780

Arg Trp Thr Ala Pro Ala Glu Thr Val Thr Val Lys Gly Arg Asp His
785                 790                 795                 800

Ala Leu Asn Pro Pro Val Leu Glu Thr Asn Ala Arg Leu Ala Gln
                805                 810                 815

Pro Thr Leu Gly Val Thr Val Ser Lys Glu Asn Leu Ser Pro Leu Ile
                820                 825                 830

Val Pro Pro Glu Ser His Leu Pro Lys Glu Glu Ser Asp Arg Ala
                835                 840                 845

Glu Gly Asn Ala Val Pro Val Lys Glu Leu Val Pro Gly Arg Arg Leu
850                 855                 860

Gln Gln Asn Tyr Pro Gly Phe Leu Pro Trp Glu Lys Lys Tyr Phe
865                 870                 875                 880

Gln Asp Leu Leu Asp Glu Glu Glu Ser Leu Lys Thr Gln Leu Ala Tyr
                885                 890                 895

Phe Thr Asp Arg Lys His Thr Gly Arg Gln Leu Lys
                900                 905

<210> SEQ ID NO 10
<211> LENGTH: 328
<212> TYPE: PRT
<213> ORGANISM: Mus musculus

<400> SEQUENCE: 10

Asp Thr Phe Ala Asp Ser Leu Arg Tyr Val Asn Lys Ile Leu Asn Ser
1               5                   10                  15

Lys Phe Gly Phe Thr Ser Arg Lys Val Pro Ala His Met Pro His Met
                20                  25                  30

Ile Asp Arg Ile Val Met Gln Glu Leu Gln Asp Met Phe Pro Glu Glu
            35                  40                  45

Phe Asp Lys Thr Ser Phe His Lys Val Arg His Ser Glu Asp Met Gln
50                  55                  60

Phe Ala Phe Ser Tyr Phe Tyr Leu Met Ser Ala Val Gln Pro Leu
65                  70                  75                  80

Asn Ile Ser Gln Val Phe His Glu Val Asp Thr Asp Gln Ser Gly Val
                85                  90                  95
```

```
Leu Ser Asp Arg Glu Ile Arg Thr Leu Ala Thr Arg Ile His Asp Leu
            100                 105                 110
Pro Leu Ser Leu Gln Asp Leu Thr Gly Leu Glu His Met Leu Ile Asn
        115                 120                 125
Cys Ser Lys Met Leu Pro Ala Asn Ile Thr Gln Leu Asn Asn Ile Pro
    130                 135                 140
Pro Thr Gln Glu Ala Tyr Tyr Asp Pro Asn Leu Pro Pro Val Thr Lys
145                 150                 155                 160
Ser Leu Val Thr Asn Cys Lys Pro Val Thr Asp Lys Ile His Lys Ala
                165                 170                 175
Tyr Lys Asp Lys Asn Lys Tyr Arg Phe Glu Ile Met Gly Glu Glu Glu
            180                 185                 190
Ile Ala Phe Lys Met Ile Arg Thr Asn Val Ser His Val Val Gly Gln
        195                 200                 205
Leu Asp Asp Ile Arg Lys Asn Pro Arg Lys Phe Val Cys Leu Asn Asp
    210                 215                 220
Asn Ile Asp His Asn His Lys Asp Ala Arg Thr Val Lys Ala Val Leu
225                 230                 235                 240
Arg Asp Phe Tyr Glu Ser Met Phe Pro Ile Pro Ser Gln Phe Glu Leu
                245                 250                 255
Pro Arg Glu Tyr Arg Asn Arg Phe Leu His Met His Glu Leu Gln Glu
            260                 265                 270
Trp Arg Ala Tyr Arg Asp Lys Leu Lys Phe Trp Thr His Cys Val Leu
        275                 280                 285
Ala Thr Leu Ile Ile Phe Thr Ile Phe Ser Phe Phe Ala Glu Gln Ile
    290                 295                 300
Ile Ala Leu Lys Arg Lys Ile Phe Pro Arg Arg Ile His Lys Glu
305                 310                 315                 320
Ala Ser Pro Asp Arg Ile Arg Val
                325

<210> SEQ ID NO 11
<211> LENGTH: 2070
<212> TYPE: DNA
<213> ORGANISM: Mus musculus
<220> FEATURE:
<221> NAME/KEY: misc_feature
<222> LOCATION: (186)..(186)
<223> OTHER INFORMATION: n is a, t, c, or g

<400> SEQUENCE: 11
gtgagaccct aggagcaatg gccgggcggc tggctggctt cctgatgttg ctggggctcg        60
cgtcgcaggg gcccgcgccg gcatgtgccg ggaagatgaa ggtggtggag gagcctaaca       120
cattcgggtg agcggatcac ggtcctgcgg cttggggacc gagcctggct ggttcttctg       180
accttntcaa ttccataggc tgaataaccc gttcttgccc caggcaagcc gccttcagcc       240
caagagagag ccttcagctg tatcccgcaa attaagagaa attaatttca aacgatttag       300
aaagtattct agccaggcga tgatggcgca cgcctttaat cccagcactt gggaggcaga       360
ggcaggcaga tttccgagtt caaggccatc agaactgact gtacatctta gtacagttta       420
gcatgtgatc agagatctga atcacaaagc tgggcctgcg tggtaaagca ggtcctttct       480
aataaggttg cagtttagat tttctttctt aactctttta ttctttgaga cagggtttct       540
caacagtggg tgtcctggaa ctcacttttg taaaccaggc tgcccttaaa ctcacaaagc       600
tctgtcagcc tctgcctcct gagtgctggg attaaaggtc cacaccctgt tcattcattt       660
```

-continued

```
ttaattttg agactgggtc tcattatgtg ccctagaca gatactgaga gcctcctcca      720
caggaacaag catgggaatc ctgccacaga caaccagttc tgtggtctgg agatgagttt      780
gtcagtccct aggagttagg tcagcctgcc tctgcattcc caataattta ggaaaggagc      840
ttggggcgtt ctggccttga tggttagtgc cctcctgcca accttagctt ccagctttag      900
gggtagcaga gtttataccg atgctaaact gctgttgtgt tcttccccag gcccctgca      960
tctcttcaga cttgctggca agtgctttag cctagtggag tccacgtgag tgccaggctg     1020
gtgggtggag tgggcggagt ctgcagagct cctgatgtgc ctgtgtttcc caggtacaag     1080
tatgaattct gccctttcca caacgtcacc cagcacgagc agaccttccg ctggaatgcc     1140
tacagcggga tccttggcat ctggcatgag tgggaaatca tcaacaatac cttcaagggc     1200
atgtggatga ctgatgggga ctcctgccac tcccggagcc ggcagagcaa ggtggagctc     1260
acctgtggaa agatcaaccg actggccac gtgtctgagc caagcacctg tgtctatgca     1320
ttgacattcg agacccctct tgtttgccat ccccactctt tgttagtgta tccaactctg     1380
tcagaagccc tgcagcagcc cttggaccag gtggaacagg acctggcaga tgaactgatc     1440
acaccacagg gctatgagaa gttgctaagg gtacttttg aggatgctgg ctacttaaag     1500
gtcccaggag aaacccatcc cacccagctg gcaggaggtt ccaagggcct ggggcttgag     1560
actctggaca actgtagaaa ggcacatgca gagctgtcac aggaggtaca aagactgacg     1620
agtctgctgc aacagcatgg aatccccac actcagccca caggtcagtc tgcctgccct     1680
ggtcagctgc cagccactcc ggggcctgca gcactggggc agatctttat tgctacccat     1740
tctggcagaa accactcact ctcagcacct gggtcagcag ctccccatag gtgcaatcgc     1800
agcagagcat ctgcggagtg acccaggact acgtgggaac atcctgtgag caaggtggcc     1860
acgaagaata gaaatatcct gagctttgag tgtcctttca cagagtgaac aaaactggtg     1920
tggtgtagac acggcttctt ttggcatatt ctagatcaga cagtgtcact gacaaacaag     1980
agggacctgc tggccagcct ttgttgtgcc caaagatcca gacaaaataa agattcaaag     2040
ttttaattaa aaaaaaaaaa aaaggaattc                                       2070
```

<210> SEQ ID NO 12
<211> LENGTH: 307
<212> TYPE: PRT
<213> ORGANISM: Mus musculus

<400> SEQUENCE: 12

```
Met Ala Gly Arg Leu Ala Gly Phe Leu Met Leu Leu Gly Leu Ala Ser
1               5                   10                  15

Gln Gly Pro Ala Pro Ala Cys Ala Gly Lys Met Lys Val Val Glu Glu
            20                  25                  30

Pro Asn Thr Phe Gly Leu Asn Asn Pro Phe Leu Pro Gln Ala Ser Arg
        35                  40                  45

Leu Gln Pro Lys Arg Glu Pro Ser Ala Val Ser Gly Pro Leu His Leu
    50                  55                  60

Phe Arg Leu Ala Gly Lys Cys Phe Ser Leu Val Glu Ser Thr Tyr Lys
65                  70                  75                  80

Tyr Glu Phe Cys Pro Phe His Asn Val Thr Gln His Glu Gln Thr Phe
                85                  90                  95

Arg Trp Asn Ala Tyr Ser Gly Ile Leu Gly Ile Trp His Glu Trp Glu
            100                 105                 110

Ile Ile Asn Asn Thr Phe Lys Gly Met Trp Met Thr Asp Gly Asp Ser
```

```
            115                 120                     125
Cys His Ser Arg Ser Arg Gln Ser Lys Val Glu Leu Thr Cys Gly Lys
    130                 135                 140

Ile Asn Arg Leu Ala His Val Ser Glu Pro Ser Thr Cys Val Tyr Ala
145                 150                 155                 160

Leu Thr Phe Glu Thr Pro Leu Val Cys His Pro His Ser Leu Leu Val
                165                 170                 175

Tyr Pro Thr Leu Ser Glu Ala Leu Gln Gln Arg Leu Asp Gln Val Glu
            180                 185                 190

Gln Asp Leu Ala Asp Glu Leu Ile Thr Pro Gln Gly Tyr Glu Lys Leu
        195                 200                 205

Leu Arg Val Leu Phe Glu Asp Ala Gly Tyr Leu Lys Val Pro Gly Glu
    210                 215                 220

Thr His Pro Thr Gln Leu Ala Gly Gly Ser Lys Gly Leu Gly Leu Glu
225                 230                 235                 240

Thr Leu Asp Asn Cys Arg Lys Ala His Ala Glu Leu Ser Gln Glu Val
                245                 250                 255

Gln Arg Leu Thr Ser Leu Leu Gln Gln His Gly Ile Pro His Thr Gln
            260                 265                 270

Pro Thr Glu Thr Thr His Ser Gln His Leu Gly Gln Gln Leu Pro Ile
        275                 280                 285

Gly Ala Ile Ala Ala Glu His Leu Arg Ser Asp Pro Gly Leu Arg Gly
    290                 295                 300

Asn Ile Leu
305

<210> SEQ ID NO 13
<211> LENGTH: 460
<212> TYPE: DNA
<213> ORGANISM: Rattus rattus

<400> SEQUENCE: 13
attcccacca acattcaagg agacgagtca gctgaagaca aaactgccag aaaatctttc      60
ttctaaaata aaactgttgc agctgtactc ggaggccagc gtcgctcttc tgaaattgaa     120 taacccaaa ggtttccccg agctgaacaa gcagaccaag aagaacatga gcatcagtgg     180
gaaggaactg gccatcagcc ctgcctatct gctgtgggac ctgagcgcca tcagccagtc     240
caagcaggat gaagatgtgt ctgccagccg cttcgaggat aacgaagagc tgaggtactc     300
actgagatct atcgagagac atgattccat gagtccttta tgaattctgg ccatatcttc     360
aatcatgatc tcagtagtat tcctctgaaa tggcacacat ttttctaatg agaacttgaa     420 atgtaaaatat tgtgtttgtg ctgtaaattt tgtgtatttc                           460

<210> SEQ ID NO 14
<211> LENGTH: 113
<212> TYPE: PRT
<213> ORGANISM: Rattus rattus

<400> SEQUENCE: 14

Phe Pro Pro Thr Phe Lys Glu Thr Ser Gln Leu Lys Thr Lys Leu Pro
1               5                   10                  15

Glu Asn Leu Ser Ser Lys Ile Lys Leu Leu Gln Leu Tyr Ser Glu Ala
            20                  25                  30

Ser Val Ala Leu Leu Lys Leu Asn Asn Pro Lys Gly Phe Pro Glu Leu
        35                  40                  45
```

| Asn | Lys | Gln | Thr | Lys | Lys | Asn | Met | Ser | Ile | Ser | Gly | Lys | Glu | Leu | Ala |
|---|---|---|---|---|---|---|---|---|---|---|---|---|---|---|---|
| | 50 | | | | 55 | | | | 60 | | | | | | |

| Ile | Ser | Pro | Ala | Tyr | Leu | Leu | Trp | Asp | Leu | Ser | Ala | Ile | Ser | Gln | Ser |
|---|---|---|---|---|---|---|---|---|---|---|---|---|---|---|---|
| 65 | | | | | 70 | | | | 75 | | | | | 80 | |

| Lys | Gln | Asp | Glu | Asp | Val | Ser | Ala | Ser | Arg | Phe | Glu | Asp | Asn | Glu | Glu |
|---|---|---|---|---|---|---|---|---|---|---|---|---|---|---|---|
| | | | | 85 | | | | | 90 | | | | | 95 | |

| Leu | Arg | Tyr | Ser | Leu | Arg | Ser | Ile | Glu | Arg | His | Asp | Ser | Met | Ser | Pro |
|---|---|---|---|---|---|---|---|---|---|---|---|---|---|---|---|
| | | | 100 | | | | | 105 | | | | 110 | | | |

Leu

<210> SEQ ID NO 15
<211> LENGTH: 1105
<212> TYPE: DNA
<213> ORGANISM: Drosophila melanogaster
<220> FEATURE:
<221> NAME/KEY: misc_feature
<222> LOCATION: (903)..(903)
<223> OTHER INFORMATION: n is a, g, t, or c
<221> NAME/KEY: misc_feature
<222> LOCATION: (935)..(935)
<223> OTHER INFORMATION: n is a, g, t, or c
<221> NAME/KEY: misc_feature
<222> LOCATION: (1023)..(1023)
<223> OTHER INFORMATION: n is a, g, t, or c
<221> NAME/KEY: misc_feature
<222> LOCATION: (1035)..(1035)
<223> OTHER INFORMATION: n is a, g, t, or c
<221> NAME/KEY: misc_feature
<222> LOCATION: (1071)..(1071)
<223> OTHER INFORMATION: n is a, g, t, or c
<221> NAME/KEY: misc_feature
<222> LOCATION: (1100)..(1100)
<223> OTHER INFORMATION: n is a, g, t, or c

<400> SEQUENCE: 15

| | | | | | |
|---|---|---|---|---|---|
| ctgcaggaat | tcggcacgag | gcggttcgat | gacaagaatg | agctgcggta | ctctctgagg | 60 |
| tccctggaaa | acacgccgc | atggatcagg | catgtgtaca | tagtaaccaa | tggccagatt | 120 |
| ccaagttggc | tggatctcag | ctacgaaagg | gtcacggtgg | tgccccacga | agtcctggct | 180 |
| cccgatcccg | accagctgcc | caccttctcc | agctcggcca | tcgagacatt | tctgcaccgc | 240 |
| ataccaaagc | tgtccaagag | gttcctctac | ctcaacgacg | acatattcct | gggagctccg | 300 |
| ctgtatccgg | aggacttgta | cactgaagcg | gagggagttc | gcgtgtacca | ggcatggatg | 360 |
| gtgcccggct | gcgccttgga | ttgcccctgg | acgtacatag | gtgatggagc | ttgcgatcgg | 420 |
| cactgcaaca | ttgatgcgtg | ccaatttgat | ggaggcgact | gcagtgaaac | tgggccagcg | 480 |
| agcgatgccc | acgtcattcc | accaagcaaa | gaagtgctcg | aggtgcagcc | tgccgctgtt | 540 |
| ccacaatcaa | gagtccaccg | atttcctcag | atgggtctcc | aaaagctgtt | caggcgcagc | 600 |
| tctgccaatt | ttaaggatgt | tatgcggcac | cgcaatgtgt | ccacactcaa | ggaactacgt | 660 |
| cgcattgtgg | agcgttttaa | caaggccaaa | ctcatgtcgc | tgaacccga | actggagacc | 720 |
| tccagctccg | agccacagac | aactcagcgc | cacgggctgc | gcaaggagga | ttttaagtct | 780 |
| tccaccgata | tttactctca | ctcgctgatt | gccaccaata | tgttgctgaa | tagagcctat | 840 |
| ggctttaagg | cacgccatgt | cctggcgcac | gtgggcttcc | taattgacaa | ggatattgtg | 900 |
| gangccatgc | aacgacgttt | taccagcgaa | ttctngacac | tggccattaa | cgctttccga | 960 |
| gccccaacag | atttgcagta | cgcattcgct | tactacttct | ttctaatgag | cgaaatccaa | 1020 |
| gtnatgagtg | tagangaaat | cttcgatgaa | gtcgacaccg | gacggtttgg | ncacctggtc | 1080 |
| ggatccagaa | gtgcgaaccn | tttta | | | | 1105 |

<210> SEQ ID NO 16
<211> LENGTH: 502
<212> TYPE: PRT
<213> ORGANISM: Drosophila melanogaster

<400> SEQUENCE: 16

```
Gly Thr Arg Arg Phe Asp Asp Lys Asn Glu Leu Arg Tyr Ser Leu Arg
1               5                   10                  15

Ser Leu Glu Lys His Ala Ala Trp Ile Arg His Val Tyr Ile Val Thr
            20                  25                  30

Asn Gly Gln Ile Pro Ser Trp Leu Asp Leu Ser Tyr Glu Arg Val Thr
        35                  40                  45

Val Val Pro His Glu Val Leu Ala Pro Asp Pro Asp Gln Leu Pro Thr
    50                  55                  60

Phe Ser Ser Ser Ala Ile Glu Thr Phe Leu His Arg Ile Pro Lys Leu
65                  70                  75                  80

Ser Lys Arg Phe Leu Tyr Leu Asn Asp Asp Ile Phe Leu Gly Ala Pro
                85                  90                  95

Leu Tyr Pro Glu Asp Leu Tyr Thr Glu Ala Glu Gly Val Arg Val Tyr
            100                 105                 110

Gln Ala Trp Met Val Pro Gly Cys Ala Leu Asp Cys Pro Trp Thr Tyr
        115                 120                 125

Ile Gly Asp Gly Ala Cys Asp Arg His Cys Asn Ile Asp Ala Cys Gln
    130                 135                 140

Phe Asp Gly Gly Asp Cys Ser Glu Thr Gly Pro Ala Ser Asp Ala His
145                 150                 155                 160

Val Ile Pro Pro Ser Lys Glu Val Leu Glu Val Gln Pro Ala Ala Val
                165                 170                 175

Pro Gln Ser Arg Val His Arg Phe Pro Gln Met Gly Leu Gln Lys Leu
            180                 185                 190

Phe Arg Arg Ser Ser Ala Asn Phe Lys Asp Val Met Arg His Arg Asn
        195                 200                 205

Val Ser Thr Leu Lys Glu Leu Arg Arg Ile Val Glu Arg Phe Asn Lys
    210                 215                 220

Ala Lys Leu Met Ser Leu Asn Pro Glu Leu Glu Thr Ser Ser Ser Glu
225                 230                 235                 240

Pro Gln Thr Thr Gln Arg His Gly Leu Arg Lys Glu Asp Phe Lys Ser
                245                 250                 255

Ser Thr Asp Ile Tyr Ser His Ser Leu Ile Ala Thr Asn Met Leu Leu
            260                 265                 270

Asn Arg Ala Tyr Gly Phe Lys Ala Arg His Val Leu Ala His Val Gly
        275                 280                 285

Phe Leu Ile Asp Lys Asp Ile Val Glu Ala Met Gln Arg Arg Phe His
    290                 295                 300

Gln Gln Ile Leu Asp Thr Ala His Gln Arg Phe Arg Ala Pro Thr Asp
305                 310                 315                 320

Leu Gln Tyr Ala Phe Ala Tyr Tyr Ser Phe Leu Met Ser Glu Thr Lys
                325                 330                 335

Val Met Ser Val Glu Glu Ile Phe Asp Glu Phe Asp Thr Asp Gly Ser
            340                 345                 350

Ala Thr Trp Ser Asp Arg Glu Val Arg Thr Phe Leu Thr Arg Ile Tyr
        355                 360                 365

Gln Pro Pro Leu Asp Trp Ser Ala Met Arg Tyr Phe Glu Glu Val Val
    370                 375                 380
```

```
Gln Asn Cys Thr Arg Asn Leu Gly Met His Leu Lys Val Asp Thr Val
385                 390                 395                 400

Glu His Ser Thr Leu Val Tyr Glu Arg Tyr Glu Asp Ser Asn Leu Pro
            405                 410                 415

Thr Ile Thr Arg Asp Leu Val Val Arg Cys Pro Leu Leu Ala Glu Ala
                420                 425                 430

Leu Ala Ala Asn Phe Ala Val Arg Pro Lys Tyr Asn Phe His Val Ser
            435                 440                 445

Pro Lys Arg Thr Ser His Ser Asn Phe Met Met Leu Thr Ser Asn Leu
        450                 455                 460

Thr Glu Val Val Glu Ser Leu Asp Arg Leu Arg Arg Asn Pro Arg Lys
465                 470                 475                 480

Phe Asn Cys Ile Asn Asp Asn Leu Asp Ala Asn Arg Gly Glu Asp Asn
                485                 490                 495

Glu Asp Gly Ala Pro Ser
            500

<210> SEQ ID NO 17
<211> LENGTH: 2183
<212> TYPE: DNA
<213> ORGANISM: Homo sapiens

<400> SEQUENCE: 17
```

| | |
|---|---:|
| atggcgacct ccacgggtcg ctggcttctc ctccggcttg cactattcgg cttcctctgg | 60 |
| gaagcgtccg gcggcctcga ctcggggggcc tcccgcgacg acgacttgct actgccctat | 120 |
| ccacgcgcgc gcgcgcgcct cccccgggac tgcacacggg tgcgcgccgg caaccgcgag | 180 |
| cacgagagtt ggcctccgcc tcccgcgact cccggcgccg cggtctggcc cgtgcgcacc | 240 |
| ttcgtgtcgc acttcaggga ccgcgcggtg gccggccacc tgacgcgggc cgttgagccc | 300 |
| ctgcgcacct tctcggtgct ggagcccggt ggacccggcg ctgcgcggcc gagacgacgc | 360 |
| gccaccgtgg aggagacggc gcgggcggcc gactgccgtg tcgcccagaa cggcggcttc | 420 |
| ttccgcatga actcgggcga gtgcctgggc aacgtggtga cgacgagcgc gcgggtgagc | 480 |
| agctccgggg ggctgcagaa cgcgcagttc gggatccgcc gcgacgggac cctggtcacc | 540 |
| gggtacctgt ctgaggagga ggtgctggac actgagaacc catttgtgca gctgctgagt | 600 |
| ggggtcgtgt ggctgattcg taatggaagc atctacatca acgagagcca agccacagag | 660 |
| tgtgacgaga cacaggagac aggttccttt agcaaatttg tgaatgtgat atcagccagg | 720 |
| acggccattg ccacgaccg aaagggcag ctggtgctct tcatgcaga cggccatacg | 780 |
| gagcagcgtg gcatcaacct gtgggaaatg gcggagttcc tgctgaaaca ggacgtggtc | 840 |
| aacgccatca acctggatgg gggtggctct gccaccttg tgctcaacgg gaccttggcc | 900 |
| agttacccgt cagatcactg ccaggacaac atgtggcgct gtccccgcca agtgtccacc | 960 |
| gtggtgtgtg tgcacgaacc ccgctgccag ccgcctgact gccacggcca cgggacctgc | 1020 |
| gtggacgggc actgccaatg caccgggcac ttctggcggg gtcccggctg tgatgagctg | 1080 |
| gactgtggcc cctctaactg cagccagcac ggactgtgca cggagaccgg ctgccgctgt | 1140 |
| gatgccggat ggaccgggtc caactgcagt gaagagtgtc ccttggctg catgggccg | 1200 |
| ggctgccaga ggcgttgtaa gtgtgagcac cattgtcccc gtgaccccaa gactggcaac | 1260 |
| tgcagcgtct ccagagtaaa gcagtgtctc cagccacctg aagccaccct gagggcggga | 1320 |
| gaactctcct tttcaccag gaccgcctgg ctagccctca ccctggcgct ggccttcctc | 1380 |

-continued

```
ctgctgatca gcattgcagc aaacctgtcc ttgctcctgt ccagagcaga gaggaaccgg    1440
cgcctgcatg gggactatgc ataccacccg ctgcaggaga tgaacgggga gcctctggcc    1500
gcagagaagg agcagccagg gggcgcccac aacccttca aggactgaag cctcaagctg     1560
cccggggtgg cacgtcgcga aagcttgttt ccccacggtc tggcttctgc agggaaatt    1620 tcaaggccac tggcgtggac catctgggtg tcctcaatgg cccctgtggg gcagccaagt    1680
tcctgatagc acttgtgcct cagcccctca cctggccacc tgccagggca cctgcaaccc    1740
tagcaatacc atgctcgctg gagaggctca gctgcctgct tctcgcctgc ctgtgtctgc    1800
tgccgagaag cccgtgcccc cgggagggct gccgcactgc caaagagtct ccctcctcct    1860
ggggaagggg ctgccaacga accagactca gtgaccacgt catgacagaa cagcacatcc    1920
tggccagcac ccctggctgg agtgggttaa agggacgagt ctgccttcct ggctgtgaca    1980
cgggacccct tttctacaga cctcatcact ggatttgcca actagaattc gatttcctgt    2040
cataggaagc tccttggaag aagggatggg gggatgaaat catgtttaca gacctgtttt    2100
gtcatcctgc tgccaagaag ttttttaatc acttgaataa attgatataa taaaaggagc    2160
caccaggtgg tgtgtggatt ctg                                            2183
```

<210> SEQ ID NO 18
<211> LENGTH: 515
<212> TYPE: PRT
<213> ORGANISM: Homo sapiens

<400> SEQUENCE: 18

```
Met Ala Thr Ser Thr Gly Arg Trp Leu Leu Arg Leu Ala Leu Phe
1               5                   10                  15

Gly Phe Leu Trp Glu Ala Ser Gly Gly Leu Asp Ser Gly Ala Ser Arg
                20                  25                  30

Asp Asp Asp Leu Leu Pro Tyr Pro Arg Ala Arg Ala Arg Leu Pro
            35                  40                  45

Arg Asp Cys Thr Arg Val Arg Ala Gly Asn Arg Glu His Glu Ser Trp
        50                  55                  60

Pro Pro Pro Ala Thr Pro Gly Ala Gly Leu Ala Val Arg Thr
65                  70                  75                  80

Phe Val Ser His Phe Arg Asp Arg Ala Val Ala Gly His Leu Thr Arg
                85                  90                  95

Ala Val Glu Pro Leu Arg Thr Phe Ser Val Leu Glu Pro Gly Gly Pro
            100                 105                 110

Gly Gly Cys Ala Ala Arg Arg Arg Ala Thr Val Glu Glu Thr Ala Arg
        115                 120                 125

Ala Ala Asp Cys Arg Val Ala Gln Asn Gly Gly Phe Phe Arg Met Asn
    130                 135                 140

Ser Gly Glu Cys Leu Gly Asn Val Val Ser Asp Glu Arg Arg Val Ser
145                 150                 155                 160

Ser Ser Gly Gly Leu Gln Asn Ala Gln Phe Gly Ile Arg Arg Asp Gly
                165                 170                 175

Thr Leu Val Thr Gly Tyr Leu Ser Glu Glu Val Leu Asp Thr Glu
            180                 185                 190

Asn Pro Phe Val Gln Leu Leu Ser Gly Val Val Trp Leu Ile Arg Asn
        195                 200                 205

Gly Ser Ile Tyr Ile Asn Glu Ser Gln Ala Thr Glu Cys Asp Glu Thr
    210                 215                 220

Gln Glu Thr Gly Ser Phe Ser Lys Phe Val Asn Val Ile Ser Ala Arg
```

```
                            225                 230                 235                 240
        Thr Ala Ile Gly His Asp Arg Lys Gly Gln Leu Val Leu Phe His Ala
                            245                 250                 255
        Asp Gly His Thr Glu Gln Arg Gly Ile Asn Leu Trp Glu Met Ala Glu
                        260                 265                 270
        Phe Leu Leu Lys Gln Asp Val Val Asn Ala Ile Asn Leu Asp Gly Gly
                    275                 280                 285
        Gly Ser Ala Thr Phe Val Leu Asn Gly Thr Leu Ala Ser Tyr Pro Ser
                290                 295                 300
        Asp His Cys Gln Asp Asn Met Trp Arg Cys Pro Arg Gln Val Ser Thr
        305                 310                 315                 320
        Val Val Cys Val His Glu Pro Arg Cys Gln Pro Pro Asp Cys His Gly
                            325                 330                 335
        His Gly Thr Cys Val Asp Gly His Cys Gln Cys Thr Gly His Phe Trp
                        340                 345                 350
        Arg Gly Pro Gly Cys Asp Glu Leu Asp Cys Gly Pro Ser Asn Cys Ser
                    355                 360                 365
        Gln His Gly Leu Cys Thr Glu Thr Gly Cys Arg Cys Asp Ala Gly Trp
                370                 375                 380
        Thr Gly Ser Asn Cys Ser Glu Glu Cys Pro Leu Gly Trp His Gly Pro
        385                 390                 395                 400
        Gly Cys Gln Arg Arg Cys Lys Cys Glu His His Cys Pro Cys Asp Pro
                            405                 410                 415
        Lys Thr Gly Asn Cys Ser Val Ser Arg Val Lys Gln Cys Leu Gln Pro
                        420                 425                 430
        Pro Glu Ala Thr Leu Arg Ala Gly Glu Leu Ser Phe Phe Thr Arg Thr
                    435                 440                 445
        Ala Trp Leu Ala Leu Thr Leu Ala Leu Ala Phe Leu Leu Leu Ile Ser
                450                 455                 460
        Ile Ala Ala Asn Leu Ser Leu Leu Leu Ser Arg Ala Glu Arg Asn Arg
        465                 470                 475                 480
        Arg Leu His Gly Asp Tyr Ala Tyr His Pro Leu Gln Glu Met Asn Gly
                            485                 490                 495
        Glu Pro Leu Ala Ala Glu Lys Glu Gln Pro Gly Gly Ala His Asn Pro
                        500                 505                 510
        Phe Lys Asp
                515

<210> SEQ ID NO 19
<211> LENGTH: 2005
<212> TYPE: DNA
<213> ORGANISM: Mus musculus

<400> SEQUENCE: 19
gtttcccgcg acgatgacct gctgctgcct tacccactag cgcgcagacg tccctcgcga      60
gactgcgccc gggtgcgctc aggtagccca gagcaggaga gctggcctcc gccacctctg     120
gccacccacg aaccccgggc gccaagccac acgcggccg tgcgcacctt cgtgtcgcac      180
ttcgaggggc gcgcggtggc cggccacctg acgcgggtcg ccgatcccct acgcactttc    240
tcggtgctgg agcccggagg agccgggggc tgcggcggca aagcgccgc ggctactgtg     300 gaggacacag ccgtccgggc cggttgccgc atcgctcaga acgtggcttt cttccgcatg    360
agcactggcg agtgcttggg gaacgtggtg agcgacgggc ggctggtgag cagctcaggg    420
ggactgcaga acgcgcagtt cggtatccga cgcgatggaa ccatagtcac cgggtcctgt    480
```

```
cttgaagaag aggttctgga tcccgtgaat ccgttcgtgc agctgctgag cggagtcgtg      540
tggctcatcc gcaatggaaa catctacatc aacgagagcc aagccatcga gtgtgacgag      600
acacaggaga caggttcttt tagcaaattt gtgaatgtga tgtcagccag acagccgtg       660 ggtcatgacc gtgaggggca gcttatcctc ttccatgctg atggacagac ggaacagcgt      720
ggccttaacc tatgggagat ggcagagttc ctgcgtcaac aagatgtcgt caatgccatc      780
aacctggatg gaggcggttc tgctactttt gtgctcaatg ggaccctggc cagttaccct      840
tcagatcact gccaggacaa catgtggcgc tgtccccgcc aagtgtccac tgtggtgtgt      900
gtgcatgaac cgcgctgcca gccacccgac tgcagtggcc atgggacctg tgtggatggc      960
cactgtgaat gcaccagcca cttctggcgg ggcgaggcct gcagcgagct ggactgtggc     1020
ccctccaact gcagccagca tgggctgtgc acagctggct gccactgtga tgctgggtgg     1080
acaggatcca actgcagtga agagtgtcct ctgggctggt atgggccagg ttgccagagg     1140
ccctgccagt gtgagcacca gtgtttctgt gacccgcaga ctggcaactg cagcatctcc     1200
caagtgaggc agtgtctcca gccaactgag gctacgccga gggcaggaga gctggcctct     1260
ttcaccagga ccacctggct agccctcacc ctgacactaa ttttcctgct gctgatcagc     1320
actggggtca acgtgtcctt gttcctgggc tccaggccg agaggaaccg gcacctcgac      1380
ggggactatg tgtatcaccc actgcaggag gtgaacgggg aagcgctgac tgcagagaag     1440
gagcacatgg aggaaactag caacccttc aaggactgaa gagctgcccc aacggcatgc      1500
tccagataat cttgtccctg ctcctcactt ccacagggga cattgtgagg ccactggcat     1560
ggatgctatg cacccaccc tttgctggcc atattcctcc tgtccccatg ctgtggctca      1620
tgccaaccta gcaataagga gctctggaga gcctgcacct gcctcccgct cgcctatatc     1680
tgctgcccag aggcctgtct cgcacagggg tctcgccact gccaaagact cccaggaagt     1740
caaagactcc cagtaatcca ctagcaaatg gaactctgta acgccatcat aacaagagtg     1800
gccactctcc gcgtgcacag gtatgaaata taaatcctta cacacacaca cacacacacc     1860
ctcggctcag ccacggcact cgcctttat acagcgtcat cgctggacag ccaactagaa      1920
ctctgcatcc tgtcacagga agcacctcat aagaaggaat ggggagggaa ggcagtcgcc     1980
ttgttttcag accttagccg aattc                                           2005
```

<210> SEQ ID NO 20
<211> LENGTH: 492
<212> TYPE: PRT
<213> ORGANISM: Mus musculus

<400> SEQUENCE: 20

Val Ser Arg Asp Asp Leu Leu Leu Pro Tyr Pro Leu Ala Arg Arg
1               5                   10                  15

Arg Pro Ser Arg Asp Cys Ala Arg Val Arg Ser Gly Ser Pro Glu Gln
            20                  25                  30

Glu Ser Trp Pro Pro Pro Leu Ala Thr His Glu Pro Arg Ala Pro
        35                  40                  45

Ser His His Ala Ala Val Arg Thr Phe Val Ser His Phe Glu Gly Arg
    50                  55                  60

Ala Val Ala Gly His Leu Thr Arg Val Ala Asp Pro Leu Arg Thr Phe
65                  70                  75                  80

Ser Val Leu Glu Pro Gly Gly Ala Gly Gly Cys Gly Gly Arg Ser Ala
                85                  90                  95

-continued

```
Ala Ala Thr Val Glu Asp Thr Ala Val Arg Ala Gly Cys Arg Ile Ala
            100                 105                 110

Gln Asn Gly Gly Phe Phe Arg Met Ser Thr Gly Glu Cys Leu Gly Asn
        115                 120                 125

Val Val Ser Asp Gly Arg Leu Val Ser Ser Gly Gly Leu Gln Asn
130                 135                 140

Ala Gln Phe Gly Ile Arg Arg Asp Gly Thr Ile Val Thr Gly Ser Cys
145                 150                 155                 160

Leu Glu Glu Val Leu Asp Pro Val Asn Pro Phe Val Gln Leu Leu
                165                 170                 175

Ser Gly Val Val Trp Leu Ile Arg Asn Gly Asn Ile Tyr Ile Asn Glu
                180                 185                 190

Ser Gln Ala Ile Glu Cys Asp Glu Thr Gln Glu Thr Gly Ser Phe Ser
            195                 200                 205

Lys Phe Val Asn Val Met Ser Ala Arg Thr Ala Val Gly His Asp Arg
        210                 215                 220

Glu Gly Gln Leu Ile Leu Phe His Ala Asp Gly Gln Thr Glu Gln Arg
225                 230                 235                 240

Gly Leu Asn Leu Trp Glu Met Ala Glu Phe Leu Arg Gln Gln Asp Val
                245                 250                 255

Val Asn Ala Ile Asn Leu Asp Gly Gly Gly Ser Ala Thr Phe Val Leu
                260                 265                 270

Asn Gly Thr Leu Ala Ser Tyr Pro Ser Asp His Cys Gln Asp Asn Met
            275                 280                 285

Trp Arg Cys Pro Arg Gln Val Ser Thr Val Val Cys Val His Glu Pro
        290                 295                 300

Arg Cys Gln Pro Pro Asp Cys Ser Gly His Gly Thr Cys Val Asp Gly
305                 310                 315                 320

His Cys Glu Cys Thr Ser His Phe Trp Arg Gly Glu Ala Cys Ser Glu
                325                 330                 335

Leu Asp Cys Gly Pro Ser Asn Cys Ser Gln His Gly Leu Cys Thr Ala
                340                 345                 350

Gly Cys His Cys Asp Ala Gly Trp Thr Gly Ser Asn Cys Ser Glu Glu
            355                 360                 365

Cys Pro Leu Gly Trp Tyr Gly Pro Gly Cys Gln Arg Pro Cys Gln Cys
        370                 375                 380

Glu His Gln Cys Phe Cys Asp Pro Gln Thr Gly Asn Cys Ser Ile Ser
385                 390                 395                 400

Gln Val Arg Gln Cys Leu Gln Pro Thr Glu Ala Thr Pro Arg Ala Gly
                405                 410                 415

Glu Leu Ala Ser Phe Thr Arg Thr Thr Trp Leu Ala Leu Thr Leu Thr
                420                 425                 430

Leu Ile Phe Leu Leu Leu Ile Ser Thr Gly Val Asn Val Ser Leu Phe
            435                 440                 445

Leu Gly Ser Arg Ala Glu Arg Asn Arg His Leu Asp Gly Asp Tyr Val
        450                 455                 460

Tyr His Pro Leu Gln Glu Val Asn Gly Glu Ala Leu Thr Ala Glu Lys
465                 470                 475                 480

Glu His Met Glu Glu Thr Ser Asn Pro Phe Lys Asp
                485                 490

<210> SEQ ID NO 21
<211> LENGTH: 9792
<212> TYPE: DNA
```

<213> ORGANISM: Mus musculus

<400> SEQUENCE: 21

| | | | | | |
|---|---|---|---|---|---|
| caggctcggg | acttactata | acacaggaca | cttgtcacct | gaaagcttga | gtcagtcagt | 60 |
| tattatggtc | tgtgtgtgag | atacaagtgg | gtgcataggc | agtggtgcac | acatgtagat | 120 |
| cagactttct | acagccaatt | ctcttcttcc | tcctctccat | gggttcaggg | tcttcatctc | 180 |
| aggttgcaca | gcgagttcat | ttatgtgctg | tgccatctcg | ccagtcgttc | ctatatccta | 240 |
| gaggaaaact | agtttcttct | ggtcaagagg | aggaaagagt | ggagacctgt | cattctaaga | 300 |
| tacccaaaac | agggccaggt | tggggacctg | tgcctttaat | cccatcactt | ggggattagg | 360 |
| tagaagcaag | aggctctaga | ccagtctaca | cactgaattt | caagccagcc | tacctataaa | 420 |
| tcagagaccc | tgcttcaaaa | ataaaattaa | acaaaaacga | agataaacca | agctacccaa | 480 |
| aacacaagag | ttaatccagt | cagacaggtc | tagcaaatgc | taggatgaaa | ggtgtgcacc | 540 |
| accacgagtg | ggctgcaagc | ctctctctct | ctctctctct | ctctctctct | ctcgtttgtt | 600 |
| ttgtttttcg | agacaaggtt | tctctgtgta | gccctggctg | tcctggaact | cactctgtag | 660 |
| accaggctgg | cctcgagctt | cactcttaaa | agttcctctt | cctcctcctc | catcttttcc | 720 |
| tcctcttacc | ccctaggctc | cttttcctct | tcttgtcttt | cagataaagt | ctcaagtagt | 780 |
| ccagactggt | ctcaaactaa | ctaactagcc | aagaatagcc | aacctcttaa | cttccgattc | 840 |
| tcctgcctct | gctgaatgct | ggggttgtgg | cgtgggccac | cacttctggt | tgtgcaaca | 900 |
| cagaaggaac | tagggcttta | agcacgagaa | gcaagttctg | tacagactta | cacaggccca | 960 |
| gcatctgttc | ttgcaatttt | ctgtaagttt | gacataatat | gagaataaaa | agctatctat | 1020 |
| ctcccttcca | gccttaccct | ctctgatgga | attcgaatgc | gtaatcaaag | cacccaacag | 1080 |
| cctggcctga | aatcacgtgg | ggcaagccca | cgtgaccgga | gcaccaatcc | aatatggcgg | 1140 |
| cgcccagggg | gcccgggctg | ttcctcatac | ccgcgctgct | cggcttactc | ggggtggcgt | 1200 |
| ggtgcagctt | aagcttcggg | tgagtgcaag | ccgccggggc | cagcctggct | ggggtccacc | 1260 |
| tttcctgagc | gctctcaggc | acagccctcc | gacctcacga | tcgccccgtc | cctgcagggt | 1320 |
| ttcccgcgac | gatgacctgc | tgctgcctta | cccactagcg | cgcagacgtc | cctcgcgaga | 1380 |
| ctgcgcccgg | gtgcgctcag | gtagcccaga | gcaggagagc | tggcctccgc | cacctctggc | 1440 |
| cacccacgaa | ccccgggcgc | caagccacca | cgcggccgtg | cgcaccttcg | tgtcgcactt | 1500 |
| cgagggcgc | gcggtggccg | gccacctgac | gcggtcgcc | gatcccctac | gcactttctc | 1560 |
| ggtgctggag | cccggaggag | ccgggggctg | cggcggcaga | agcgccgcgg | ctactgtgga | 1620 |
| ggacacagcc | gtccgggccg | gttgccgcat | cgctcagaac | ggtggcttct | tccgcatgag | 1680 |
| cactggcgag | tgcttgggga | acgtggtgag | cgacgggcg | ctggtgagca | gctcaggggg | 1740 |
| actgcagaac | gcgcagttcg | gtatccgacg | cgatggaacc | atagtcaccg | ggtgaggagg | 1800 |
| cagggagccc | cggggctgta | gagggcaaag | ggtctctgat | gttctttcag | agccatgcct | 1860 |
| ccgagtccag | gtccctaacc | aaacttcctg | tctttcttct | tccgagtaat | gacgctgaca | 1920 |
| ccttccttcc | tttaagttta | ttcatgtgcc | actgaataat | ctgtgatcag | gccgtgtgtg | 1980 |
| gggacttggg | gaggcgaccg | tgagcctgaa | cacagtttgt | gccctagtga | actttgtgta | 2040 |
| gtattagaga | aacatttcgt | gttcaacgaa | gccatggaac | caattggaaa | tagtgtagag | 2100 |
| tttatggagc | agtcccagac | agctagctgg | aggccttttg | ctgtcctgat | aaaaatccag | 2160 |
| gttagacaag | gagcttgttg | agggcagcct | ttggaagttt | ctgtgtttct | tgaaatttga | 2220 |
| cagcagccag | agttgacagc | aggcaggcag | gagtagaagg | tagcgccatc | tggtgttcca | 2280 |

-continued

```
gttctcttcc aaggttccgt tttttgccaa ggctgggaag tgggctttcc ccaactcttc   2340
tcagcccttg gttgcaattt ctgggcctgc ccatgtatct ggttcttcat ccttcaacat   2400
cagccagtgt caccactgtt gatcttaggt tttcacagat cctaaaactt ctgccagtga   2460
ccagcgcctg cagtttctct tccctggctc tgtccttcaa cctctctaca ttccagccat   2520
ctccctagct cctctcttgg actcccttte agacttgttg tcatgatcac tgtctcagaa   2580
cccctattgc tccttacaa tggtccactg acctgctcac ctcctacttt tttttttaa    2640 atgtgtgtgc atctgtgtgt gcctgagggg agaccagagt ttgatttcaa atgtcttcta   2700
ttctcttttc ctccatctta ttttctaaca caaaatctga atctagagat cactggttca   2760
gttaacctgg ctggccggta aaccccaggg ccctcctgct tccctctgtc cacccccaccc  2820 cagcactaag gctacagtgt gtgctgttcc agccagcttt ctcatgggtg ctgaggatct   2880
gaacgcaggt tcacatgtgt ggtgggaagg cttttaccca atgctctgtc tttccagccc   2940
atcctccctt gttaactgcc aaacagctgc ctatcctgtc catgtgtagc tcactgctac   3000
ttcttttatt atgaggtcag cacatgttac taaagatggc aagagaagaa ggttctttca   3060
ttgtgtcata gctatagctc aggaggaatt ttatttcctg tgtaggcaca caggagagca   3120
tcttccagct cacactccaa ctgaactaac tgaacacctg cctatatatc caaagaaggg   3180
gtgtcagtgc caatcacagc acacctccag tgcaaatgaa ggtttgtgtt tgcaccaatc   3240
acagccttgc ctcttttagc atgcatcaca acaaagtcct cctagactat caggggatat   3300
gctctcttgg ccaaggtagg aatagttgca gtgtcatctg gcacaaacca tttcaaacgg   3360
cctggctgag gttatgcctt cgggaacctg aagtctttgt gtggttgtct ccaagtgtct   3420
gtggagctcc aggcggctgg tgctgacaga cgctttgtct agttggctgt ttgacttttg   3480
cttaagcagc cagggcagta gagtctaaca gatgctaatt tcaggatcag gaagactgta   3540
gaaaaatgag catcaagaag ccctggtac ccaaagctgc tcttgccaat gagtgaacct    3600
ctgccttccc gcttccaggt cctgtcttga agaagaggtt ctggatcccg tgaatccgtt   3660
cgtgcagctg ctgagcggag tcgtgtggct catccgcaat ggaaacatct acatcaacga   3720
gagccaagcc atcgagtgtg acgagacaca ggagacaggt caggaagcac aggtgttctg   3780
ttttatttgt attaggtttt gatttgttta ttttgtgcat gcagcgggtg catgcatgct   3840
cctttccttt cgccatgtga gtcctgagta ttgaactcag actgttaagt gtgatgggag   3900
gcactttacc cactgagcca ctttcccagc cctcagcatc agctttcttc agacccagga   3960
acagtgtgag tgggttattc tttagtgttc ccaaacattt actgagcagc tatttactgt   4020
ttagcactat ggtgagagtc ctagggattc agtcttatgt agaatataga aggagaatcc   4080
ttggcaataa gctggaaaat tgtgacaagt gccaagaaag aaacaggaga agggggaccg   4140
gtggggacca gaagcacagg tatgaggaaa gtgcctgcag atttgctgta tggtggcctc   4200
cacatggcct aggagtttgt cataaatgca gagccatgag tccaccctcc ctatacctcc   4260
catccagaaa ccactggtta aatcctaaca acttgggtgt gcaggcactc ccttggtgac   4320
tctgatggac actcaaggtc aagggccact tggggatggg ctgatgagtt ggcttggtca   4380
gtaaagtatt tgccttgaaa gtgtgaggac ctgagtggga gccccagaaa gaaacattaa   4440
aagccaagtg ctgggatgca cacttgcatt cccaggatg gagctggaag gcagggatag    4500
gcagatccac ggccacacgg tgatattcta agctaacaag agacctgtct cacacagaaa   4560
gtgggtggca cctgaggacc aacacccagg gttatcctct gacgtacctc cagagtggaa   4620
```

-continued

```
aatactgggg tggtggaaaa ggacactttg gtcctgggaa tctggctatt cagggtatag      4680
tgtagaggga gagggagact caagaggctg tctttgagtc aaaggaacaa gctatcagaa      4740
gaactcaggg cagaggcctg tggttcccag gctcagggca gccttcaagg ccctaggcag      4800
agagtagctg ctgggtgaac aagtacagaa gtgaggcctg gggcctcagg caaggcctgt      4860
gaaatccttc caccaacata gaagtttctg gagactgaga tcacatgaag tgcttctggc      4920
tgtggcatgg aagctcactg gaggtggagc tgggatgtgg ctcagtgatc cagtgcttgc      4980
cacacgtgca cgagggaagg agccatcaaa agagagaaag tcgggagacc tgaggggtcc      5040
cctggagagc tgggtaacca ccccgggccc ttctccttta ggttctttta gcaaatttgt      5100
gaatgtgatg tcagccagga cagccgtggg tcatgaccgt gaggggcagc ttatcctctt      5160
ccatgctgat ggacagacgg aacagcgtgg tgagtcccag gaaccttggg gctgtttgca      5220
cttcagccac cctaccttc cagtcggttc tggggtattg gtgggacaag acagctttcc       5280
ggccattttg gaagtttcat ctggaggcaa tagcatttac ctactagtga agaagccag      5340 ttaagccaga gaccacaggg gctcaagctg cataccccct ctgcacagcc ttaacctatg      5400
ggagatggca gagttcctgc gtcaacaaga tgtcgtcaat gccatcaacc tggatggagg      5460
cggttctgct acttttgtgc tcaatgggac cctggccagt tacccttcag atcactggta      5520
agaacccttg agccaccttt gtggctctct cagactgtct cactcagtca atactgagac      5580
cctgttgtgt gccaggccct gggtatccaa aagtgagcag aagagccgag atctcttccc      5640
tcagggtgct gcacagccca tccctggaaa cctgagacag gtcaggaaag gcctccctga      5700
ggacagtgaa gtaagacctg aggagatggc tggccggggt tgagagagcc tttaccggaa      5760
gacaaactgt acgcaatggg gaaatccgct aagtggccca gggagaggct ggagctatag      5820
ctcaggagga aaagtacttg cctcgcaagc gaaggacctg agtttaaact ccaaaaccca      5880
tataaaaagc cagatacgag caagtggcac atgcttgcag tcccagcctt gttgaggaag      5940
agtcaggtga atcctgaccc tctggccagc cagcctagcc tactttttgg caaggtccag      6000
gccagcgaga aagataaata aaataaagtt ttaaatgaca tgtatctaag gttgtcctga      6060
ctccatatgc gcacgcacgc atgcacgcac gcacaactgg cagaatggaa agggaggcaa      6120
actggacagc ctttataggc tgcggcaggg accagcacca aggcctagac ctcgtctcac      6180
agtgaatccc ccacagccag gacaacatgt ggcgctgtcc ccgccaagtg tccactgtgg      6240
tgtgtgtgca tgaaccgcgc tgccagccac ccgactgcag tggccatggg acctgtgtgg      6300
atggccactg tgaatgcacc agccacttct ggcggggcga ggcctgcagc gagctggact      6360
gtggcccctc caactgcagc cagcatgggc tgtgcacaga gagtgagtgg ggagcccaca      6420
ggagggtggt gctctggcgg gaccccagct cgcccatgct agactcccgc ctgtgtcctt      6480
acccagcctc tgtggtcttg ctttggtagc tggctgccac tgtgatgctg ggtggacagg      6540
atccaactgc agtgaaggtg agagctgcct gcaaacactc ctggagaggg tggcctggct      6600
gcacgcagct ggtatgacgc cttcgtccct ccttctggct tggaacttac cttcagagcc      6660
ttttctcatt tcgcatgtgg atacccgatg ttctacctac tgaaagagcc cacaagtagg      6720
aagccagatt ttcagtattg tcactcaact ctaaggacca atagcaaaaa aacaaagtgg      6780
ccacgcccct gagggagatc caccaaagtc cttaactcct ggaaagcagc tcctggtgat      6840
cctaggcatg ggtagggtgg tttcagcatc agctcagtgg agttcccatt cataatttct      6900
tcatcctttt aaggtcataa gttctagagc ccaccttaaa tctaggcagt attcttggtg      6960
tttatctgag acaaagtctt atacagccca cgcagttctc taacttagta tgtaaccgag      7020
```

```
aatggcctca agcaacctgc ttcctccttt caagcgctgg gattataggc atagcaccaa    7080
cttatagggt gctagaagtc aaacccaggg ccctatgtat atgcagcaag cactctagaa    7140
actggaacac agccctgttt gcagcccggt taccttggag ggttgggtcc cagggatctg    7200
agggcatctc cttcagcatg gccatgtgca cacccaggag ccaggctgtc tgtgacagga    7260
gaccatgcca cccaaggtga gacctccctg ccaccatctc ctctccacag agtgtcctct    7320
gggctggtat gggccaggtt gccagaggcc ctgccagtgt gagcaccagt gtttctgtga    7380
cccgcagact ggcaactgca gcatctccca aggtatgcgg ccttaaaggt tcttgagctg    7440
ggagcccttg gggcaggtct ggggtaggtg gactctcccc agcccttctt tctggtgtct    7500
tgcagtgagg cagtgtctcc agccaactga ggctacgccg agggcaggag agctggcctc    7560
tttcaccagg taagtgtttt agcaggcact gagcccctat gtctcatccg tgaggcacta    7620
gccaggccag gaggtcacag gttaccctct actttgcaag ctcagggaca gtcacaggta    7680
aaactggcat ccaggaaaga ccctgagcta cccagtggaa ctcaaaggta gcaggctatg    7740
ggtgtcatgc ctctggctgc agagactcca cttagatgct ggagcagggc catagagaca    7800
ggaaggactc accttatttc tgaactcttc cgtgtgttca ggctttgtgt tgttgttgct    7860
tcctttctgc tgtttcctgg gtttccagct ccatccccac agggctcatg aaagaattg     7920
tgaagcaggg ggtgtggctc aattggcaga ttgattgcct ggcatgcaga aagccctagg    7980
ttcaatcccc agcatttcat atcataaccc aggcatggtg gcatcatgtg cctgtaagtc    8040
cagcacttgg gaggtagaag cagaaaagcc acgagtttaa gaatgttagg gagtcttagg    8100
ccaacctggg atacctaaga caagagatag atgtagggag atagattgac agacagacag    8160
acagacagac agacagacag atcttgagct ggaccttctg gcacaagcct gtcatcctag    8220
ctattccagg aagctgaagc aggaagatag caaattcaag gccagcttaa gccacagatt    8280
gagttcaaga tcaacctgag caactttatg aaatcctatt ataacataaa agtaggggt     8340
gggaggttag gctgtagctc agtggtagag tgattgccta gcacgcacaa gacccaggtt    8400
caattcccag tactgcaaaa aatatattag gaaccccta aaagcagtaa cattcacatt      8460
agatgtgtgt gtgtgtgtgt gtgtgtgtgt gtgtgtgtgt gtgtgtgtgt gtgtgttttg    8520
ttgggtattt atttcattta catttccaat gctatcccaa aagtccccca catcctcccc    8580
cacccaccac cttgtttttt tttttttttt tttttttttt tttgacctga aactcacagg    8640
ttaggttaga caagctgact ggtgagctcc aacttccaac gtaccatcat gcctggcttt    8700
tgttttggtg tctctgtgta accctggatg tcctggagct ctctctgtag accagcctgg    8760
ccttaaactc acagaaaccc acctgtttct gcctcccatg tgctgggatt aaaggcgtgt    8820
gccacctcac ccagccctgc tggacttaaa ttgggtcttc atttttataag acaagcatga    8880
gctaattccc cagttcctaa aatgttttta acatccttaa acatcagaga ctgtctgtgg    8940
tattccctcc atgtgtcttc agtataccta ctcccctccc tgcctactgg gttcaacatg    9000
cccagtttgg gttctggctg cctgccccca ctcaagactc tcttttccat ctcaggacca    9060
cctggctagc cctcaccctg acactaattt tcctgctgct gatcagcact ggggtcaacg    9120
tgtccttgtt cctgggctcc agggccgaga ggaaccggca cctcgacggg gactatgtgt    9180
atcacccact gcaggaggtg aacggggaag cgctgactgc agagaaggag cacatggagg    9240
aaactagcaa cccccttcaag gactgaagag ctgcccaac ggcatgctcc agataatctt     9300
gtccctgctc ctcacttcca caggggacat tgtgaggcca ctggcatgga tgctatgcac    9360
```

-continued

```
cccacccttt gctggccata ttcctcctgt ccccatgctg tggctcatgc caacctagca    9420
ataaggagct ctggagagcc tgcacctgcc tcccgctcgc ctatatctgc tgcccagagg    9480
cctgtctcgc acagggtct cgccactgcc aaagactccc aggaagtcaa agactcccag    9540
taatccacta gcaaatggaa ctctgtaacg ccatcataac aagagtggcc actctccgcg    9600
tgcacaggta tgaaatataa atccttacac acacacacac acacaccctc ggctcagcca    9660
cggcactcgc cttttataca gcgtcatcgc tggacagcca actagaactc tgcatcctgt    9720
cacaggaagc acctcataag aaggaatggg gagggaaggc agtcgccttg ttttcagacc    9780
ttagccgaat tc                                                        9792
```

<210> SEQ ID NO 22
<211> LENGTH: 4
<212> TYPE: PRT
<213> ORGANISM: Artificial Sequence
<220> FEATURE:
<223> OTHER INFORMATION: synthetic peptide

<400> SEQUENCE: 22

```
    Ile Glu Gly Arg
    1
```

<210> SEQ ID NO 23
<211> LENGTH: 5
<212> TYPE: PRT
<213> ORGANISM: Artificial Sequence
<220> FEATURE:
<223> OTHER INFORMATION: synthetic peptide

<400> SEQUENCE: 23

```
    Asp Asp Asp Asp Lys
    1               5
```

<210> SEQ ID NO 24
<211> LENGTH: 6
<212> TYPE: PRT
<213> ORGANISM: Artificial Sequence
<220> FEATURE:
<223> OTHER INFORMATION: synthetic peptide

<400> SEQUENCE: 24

```
    Arg Ala Arg Tyr Lys Arg
    1               5
```

<210> SEQ ID NO 25
<211> LENGTH: 6
<212> TYPE: PRT
<213> ORGANISM: Artificial Sequence
<220> FEATURE:
<223> OTHER INFORMATION: synthetic peptide

<400> SEQUENCE: 25

```
    Pro Gly Ala Ala His Tyr
    1               5
```

<210> SEQ ID NO 26
<211> LENGTH: 46
<212> TYPE: PRT
<213> ORGANISM: Homo sapiens

<400> SEQUENCE: 26

```
    Asp Glu Glu Glu Ser Leu Lys Thr Gln Leu Ala Tyr Phe Thr Asp Ser
    1               5                   10                  15
    Lys Asn Thr Gly Arg Gln Leu Lys Asp Thr Phe Ala Asp Ser Leu Arg
```

```
            20                  25                  30
        Tyr Val Asn Lys Ile Leu Asn Ser Lys Phe Gly Phe Thr Ser
            35                  40                  45
```

<210> SEQ ID NO 27
<211> LENGTH: 112
<212> TYPE: DNA
<213> ORGANISM: Homo sapiens

<400> SEQUENCE: 27

```
gacgaagaag agtcattgaa gacacaattg gcatacttca ctgatagcaa gaatactggg      60
aggcaactaa aagatacatt tgcagattcc ctcagatatg taaataaat tc              112
```

<210> SEQ ID NO 28
<211> LENGTH: 49
<212> TYPE: DNA
<213> ORGANISM: Artificial Sequence
<220> FEATURE:
<223> OTHER INFORMATION: synthetic DNA

<400> SEQUENCE: 28

```
ctcagtaact tctgtgttaa ccggatgaac cggaattaat tcttatgac                  49
```

<210> SEQ ID NO 29
<211> LENGTH: 48
<212> TYPE: DNA
<213> ORGANISM: Artificial Sequence
<220> FEATURE:
<223> OTHER INFORMATION: synthetic DNA

<400> SEQUENCE: 29

```
gaggcaatta attaacgtct ctgcagattc cctcagatat gtaaataa                   48
```

<210> SEQ ID NO 30
<211> LENGTH: 11
<212> TYPE: PRT
<213> ORGANISM: Homo sapiens

<400> SEQUENCE: 30

```
    Asp Glu Glu Glu Ser Leu Lys Thr Gln Leu Ala
    1               5                   10
```

<210> SEQ ID NO 31
<211> LENGTH: 10
<212> TYPE: PRT
<213> ORGANISM: hybrid

<400> SEQUENCE: 31

```
    Ala Asp Ser Leu Arg Tyr Val Asn Lys Ile
    1               5                   10
```

<210> SEQ ID NO 32
<211> LENGTH: 88
<212> TYPE: DNA
<213> ORGANISM: hybrid

<400> SEQUENCE: 32

```
gacgaagaag agtcattgaa gacacaattg gcctacttgg ccttaattaa cgtctctgca      60
gattccctca gatatgtaaa taaaattc                                         88
```

<210> SEQ ID NO 33
<211> LENGTH: 25
<212> TYPE: PRT
<213> ORGANISM: hybrid

-continued

```
<400> SEQUENCE: 33

Thr Gln Leu Ala Tyr Phe Thr Asp Ser Lys Asn Thr Gly Ile Glu Gly
1               5                   10                  15

Arg Asp Thr Phe Ala Asp Ser Leu Arg
            20                  25

<210> SEQ ID NO 34
<211> LENGTH: 75
<212> TYPE: DNA
<213> ORGANISM: hybrid

<400> SEQUENCE: 34
acacaattgg cctacttcac tgatagcaag aatactggga tcgagggaag agatacattt      60
gcagattccc tcaga                                                      75

<210> SEQ ID NO 35
<211> LENGTH: 25
<212> TYPE: PRT
<213> ORGANISM: hybrid

<400> SEQUENCE: 35

Thr Gln Leu Ala Tyr Phe Thr Asp Ser Lys Asn Arg Ala Arg Tyr Lys
1               5                   10                  15

Arg Asp Thr Phe Ala Asp Ser Leu Arg
            20                  25

<210> SEQ ID NO 36
<211> LENGTH: 75
<212> TYPE: DNA
<213> ORGANISM: hybrid

<400> SEQUENCE: 36
acacaattgg cctacttcac tgatagcaag aatagagcca gatacaagag agatacattt      60
gcagattccc tcaga                                                      75

<210> SEQ ID NO 37
<211> LENGTH: 25
<212> TYPE: PRT
<213> ORGANISM: hybrid

<400> SEQUENCE: 37

Thr Gln Leu Ala Tyr Phe Thr Asp Ser Lys Asn Thr Asp Asp Asp
1               5                   10                  15

Lys Asp Thr Phe Ala Asp Ser Leu Arg
            20                  25

<210> SEQ ID NO 38
<211> LENGTH: 25
<212> TYPE: PRT
<213> ORGANISM: hybrid

<400> SEQUENCE: 38

Thr Gln Leu Ala Tyr Phe Thr Asp Ser Lys Asn Pro Gly Ala Ala His
1               5                   10                  15

Tyr Asp Thr Phe Ala Asp Ser Leu Arg
            20                  25
```

SOLUBLE GLCNAC PHOSPHOTRANSFERASE

BACKGROUND OF THE INVENTION

1. Field of the Invention

The present invention relates to a soluble GlcNAc phosphotransferase, a method of making the same and a method of phosphorylating with the same.

2. Discussion of the Background

Lysosomes are organelles in eukaryotic cells that function in the degradation of macromolecules into component parts that can be reused in biosynthetic pathways or discharged by the cell as waste. Normally, these macromolecules are broken down by enzymes known as lysosomal enzymes or lysosomal hydrolases. However, when a lysosomal enzyme is not present in the lysosome or does not function properly, the enzymes specific macromolecular substrate accumulates in the lysosome as "storage material" causing a variety of diseases, collectively known as lysosomal storage diseases.

Lysosomal storage diseases can cause chronic illness and death in hundreds of individuals each year. There are approximately 50 known lysosomal storage diseases, e.g., Pompe Disease, Hurler Syndrome, Fabry Disease, Maroteaux-Lamy Syndrome (mucopolysaccharidosis VI), Morquio Syndrome (mucopolysaccharidosis IV), Hunter Syndrome (mucopolysaccharidosis II), Farber Disease, Acid Lipase Deficiency, Krabbe Disease, and Sly Syndrome (mucopolysaccharidosis VII). In each of these diseases, lysosomes are unable to degrade a specific compound or group of compounds because the enzyme that catalyzes a specific degradation reaction is missing from the lysosome, is present in low concentrations in the lysosome, or is present at sufficient concentrations in the lysosome but is not functioning properly.

Lysosomal storage diseases have been studied extensively and the enzymes (or lack thereof) responsible for particular diseases have been identified. Most of the diseases are caused by a deficiency of the appropriate enzyme in the lysosome, often due to mutations or deletions in the structural gene for the enzyme. For some lysosomal storage diseases, the enzyme deficiency is caused by the inability of the cell to target and transport the enzymes to the lysosome, e.g., I-cell disease and pseudo-Hurler polydystrophy.

Lysosomal Storage diseases have been studied extensively and the enzymes (or lack thereof) responsible for particular diseases have been identified (Scriver, Beaudet, Sly, and Vale, eds., The Metabolic Basis of Inherited Disease, 6th Edition, 1989, Lysosomal Enzymes, Part 11, Chapters 61–72, pp. 1565–1839). Within each disease, the severity and the age at which the disease presents may be a function of the amount of residual lysosomal enzyme that exists in the patient.

The lysosomal targeting pathways have been studied extensively and the process by which lysosomal enzymes are synthesized and transported to the lysosome has been well described. Komfeld, S. (1986). "Trafficking of lysosomal enzymes in normal and disease states." *Journal of Clinical Investigation* 77: 1–6 and Kornfeld, S. (1990). "Lysosomal enzyme targeting." *Biochem. Soc. Trans.* 18: 367–374. Generally, lysosomal enzymes are synthesized by membrane-bound polysomes in the rough endoplastic reticulum ("RER") along with secretory glycoproteins. In the RER, lysosomal enzymes acquire N-linked oligosaccharides by the en-bloc transfer of a preformed oligosaccharide from dolichol phosphate containing 2 N-acetylglucosamine, 9-mannose and 3-glucose. Glycosylated lysosomal enzymes are then transported to the Golgi apparatus along with secretory proteins. In the cis-Golgi or intermediate compartment lysosomal enzymes are specifically and uniquely modified by the transfer of GlcNAc-phosphate to specific mannoses. In a second step, the GlcNAc is removed thereby exposing the mannose 6-phosphate ("M6P") targeting determinant. The lysosomal enzymes with the exposed M6P binds to M6P receptors in the trans-Golgi and is transported to the endosome and then to the lysosome. In the lysosome, the phosphates are rapidly removed by lysosomal phosphatases and the mannoses are removed by lysosomal mannosidases (Einstein, R. and Gabel, C. A. (1991). "Cell- and ligand-specific depospshorylation of acid hydrolases: evidence that the mannose 6-phosphate is controlled by compartmentalization." *Journal of Cell Biology* 112: 81–94).

The synthesis of lysosomal enzymes having exposed M6P is catalyzed by two different enzymes, both of which are essential if the synthesis is to occur. The first enzyme is UDP-N-acetylglucosamine: lysosomal enzyme N-Acetylglucosamine-1-phosphotransferase ("GlcNAc-phosphotransferase") (E.C. 2.7.8.17). GlcNAc-phosphotransferase catalyzes the transfer of N-acetylglucosamine-1-phosphate from UDP-GlcNAc to the 6 position of 1,2-linked mannoses on the lysosomal enzyme. The recognition and addition of N-acetylgluocosamine-1-phosphate to lysosomal hydrolases by GlcNAc-phosphotransferase is the critical and determining step in lysosomal targeting. The second step is catalyzed by N-acetylglucosamine-1-phosphodiester-N-Acetylglucosaminidase ("phosphodiester α-GlcNAcase") (E.C. 3.1.4.45). Phosphodiester α-GlcNAcase catalyzes the removal of N-Acetylglucosamine from the GlcNAc-phosphate modified lysosomal enzyme to generate a terminal M6P on the lysosomal enzyme.

GlcNAc-phosphotransferase is an enzyme that contains six subunits; α2β2γ2. The α and β subunits are encoded on a single mRNA and proteolytically cleaved after translation. The γ subunit is encoded on a separate mRNA molecule. Removal of the transmembrane domain from the α/β polyprotein results in a soluble form of the enzyme. This soluble form of GlcNAc-phosphotransferase facilitates a quicker and simpler purification scheme that reduces or eliminates the need for detergents to extract the non-soluble GlcNAc-phosphotransferase from membrane fractions. However, notwithstanding the ease of purification the recombinant soluble GlcNAc-phosphotransferase was not efficiently subject to post-translational proteolytic cleavage when expressed in mammalian cells such as 293T cells and CHO-K1 cells. Uncleaved forms of α/β/γ GlcNAc-phosphotransferase had poor GlcNAc phosphotransferase activity.

To solve this problem, the present inventors have discovered that by interposing a unique proteolytic cleavage site between the α and β subunits in the GlcNAc polyprotein, the polyprotein is cleaved and when expressed with the γ-subunit effectively phosphorylates an enzyme substrate.

In addition, the present inventor has discovered, quite unexpectedly, that the α and β subunits alone is catalytically active. Furthermore, the absence of the γ-subunit results in loss of substrate specificity to only those lysosomal enzymes targeted via the mannose-6-phosphate targeting systems, e.g., acid α-glucosidase, acid β-galactosidase, β-hexaminidase, and others as described herein. This loss of substrate specificity allows the soluble GlcNAc-phosphotransferase containing the α and β tetramer to effectively phosphorylated any glycoprotein having an appropriate acceptor oligosaccharide, for example, mannose-6 through mannose-9 isomers (Baranski et al (1990) Cell 63:281–291).

SUMMARY OF THE INVENTION

Thus, an object of the present invention is a method of phosphorylating a protein comprising contacting the protein with a soluble GlcNAc-phosphotransferase.

In one embodiment, the protein comprises an asparagine-linked oliogosaccharide with a high mannose structure.

In another embodiment the soluble GlcNAc-phosphotransferase contains an α subunit, a β subunit and a proteolytic cleavage site interposed between said α and β subunits, wherein said proteolytic cleavage site is not natural to said GlcNAc-phosphotrasferase.

In another embodiment, the soluble GlcNAc-phosphotransferase comprises α, β, and γ subunits.

It is another object of the present invention that in the method of phosphorylating a protein in a host cell, which contains an isolated polynucleotide encoding the soluble GlcNAc-phosphotransferase. The method is accomplished by culturing the host cell for a time under conditions suitable for expression of the soluble GlcNAc-phosphotransferase; the soluble GlcNAc-phosphotransferase is isolated and then may be employed to phosphorylate glycoproteins.

It is another object of the invention that in a method of phosphorylating a protein, a host cell containing an isolated polynucleotide encoding soluble GlcNAc-phosphotransferase is cultured for a time under conditions suitable for expression of the soluble GlcNAc-phosphotransferase, where the soluble GlcNAc-phosphotransferase has an α subunit, a β subunit, and a proteolytic cleavage site interposed between the α and β subunits, where the proteolytic cleavage site is not endogenous to the GlcNAc-phosphotransferase; the soluble GlcNAc-phosphotransferase is isolated, the isolated GlcNAc-phosphotransferase is cleaved with a proteolytic enzyme specific for the proteolytic cleavage site; and the α and β subunits are expressed with a γ subunit of GlcNAc-phosphotransferase to effectuate phosphorylation.

It is another object of the invention to provide soluble GlcNAc-phosphotransferase containing an α subunit, a β subunit and a proteolytic cleavage site interposed between the α and β subunits, where the proteolytic cleavage site is not endogenouse to GlcNAc-phosphotransferase; as well as polynucleotides which encode the soluble GlcNAc-phosphotransferase.

It is another object of the invention to provide methods of producing an α and β GlcNAc-phosphotransferase polyprotein by culturing a host cell of the invention (that which contains and expresses the GlcNAc-phosphotransferase) for a time and under conditions suitable for expression of the α and β GlcNAc-phosphotransferase polyprotein and collecting the protein produced. In one embodiment, the α and β GlcNAc-phosphotransferase subunits are cleaved in the host cell by a protease which is expressed in the cell, wherein the protease is specific for he proteolytic cleavage site interposed between the α and β subunits or are cleaved after collection from the host.

It is another object of the invention to provide a method for making a GlcNAc-phosphotransferase by combining the α and β subunits of GlcNAc-phosphotransferase with a γ subunit of GlcNAc-phosphotransferase and the GlcNAc-phosphotransferase obtained by such methods. Such methods may be accomplished in vitro by combining already expressed and collected protein subunits or by introducing a polynucleotide which encodes a γ subunit of GlcNAc-phosphotransferase into a host cell which also has the α and β subunits being expressed; culturing the host cell for a time and under conditions for the expression of the various subunits; and collecting the GlcNAc-phosphotransferase.

It is another object of the invention to provide methods of treating a patient suffering from a lysosomal storage disease, by preparing a phosphorylated lysosomal hydrolase, employing the advantages of the soluble GlcNAc-phosphotransferase, and subsequently contacting the lysosomal hydrolase with an isolated GlcNAc-phosphotransferase to produce a phosphorylated lysosomal hydrolase; the modified protein is then administered to a patient in need of treatment.

DETAILED DESCRIPTION OF THE INVENTION

Figure 1:
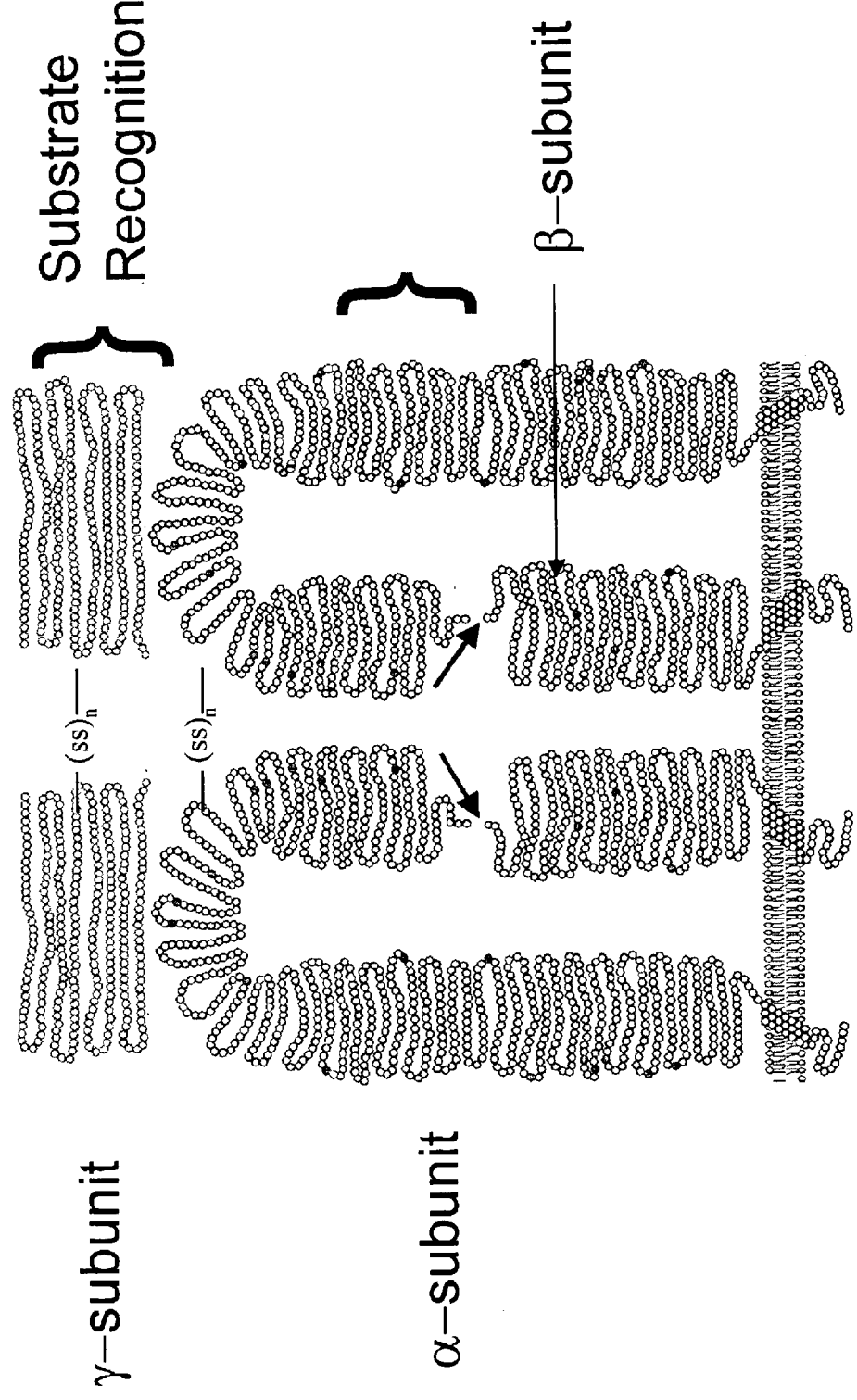
FIG. 1. Model structure of GlcNAc-phosphotransferase.
Figure 2:
FIG. 2. Schematic diagram of the phosphorylation of a lysosomal enzyme.
Figure 3:
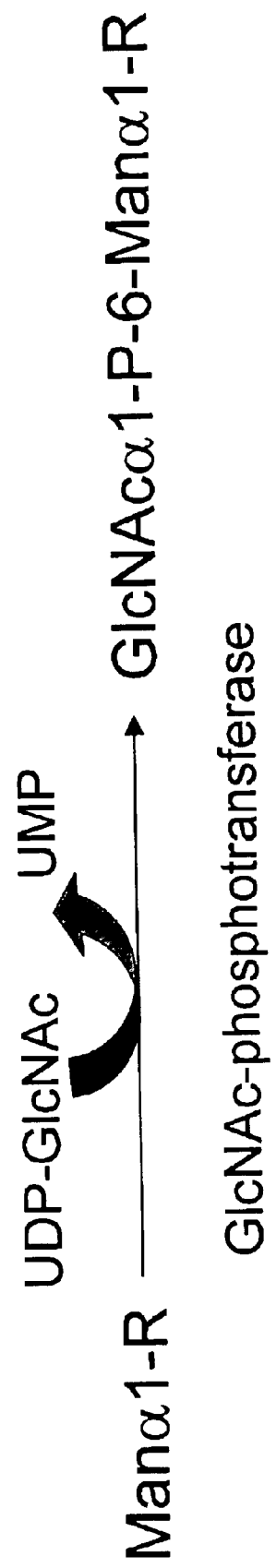
FIG. 3. Schematic diagram of the reaction of GlcNAc-phosphotransferase. One unit of GlcNAc-phosphotransferase activity is defined as 1 pmol of GlcNAc phosphate transferred to α-methylmannoside per hour in a reaction containing 150 μM UDP-GlcNAc and 100 mM α-methylmannoside at 37° C.
Figure 4:
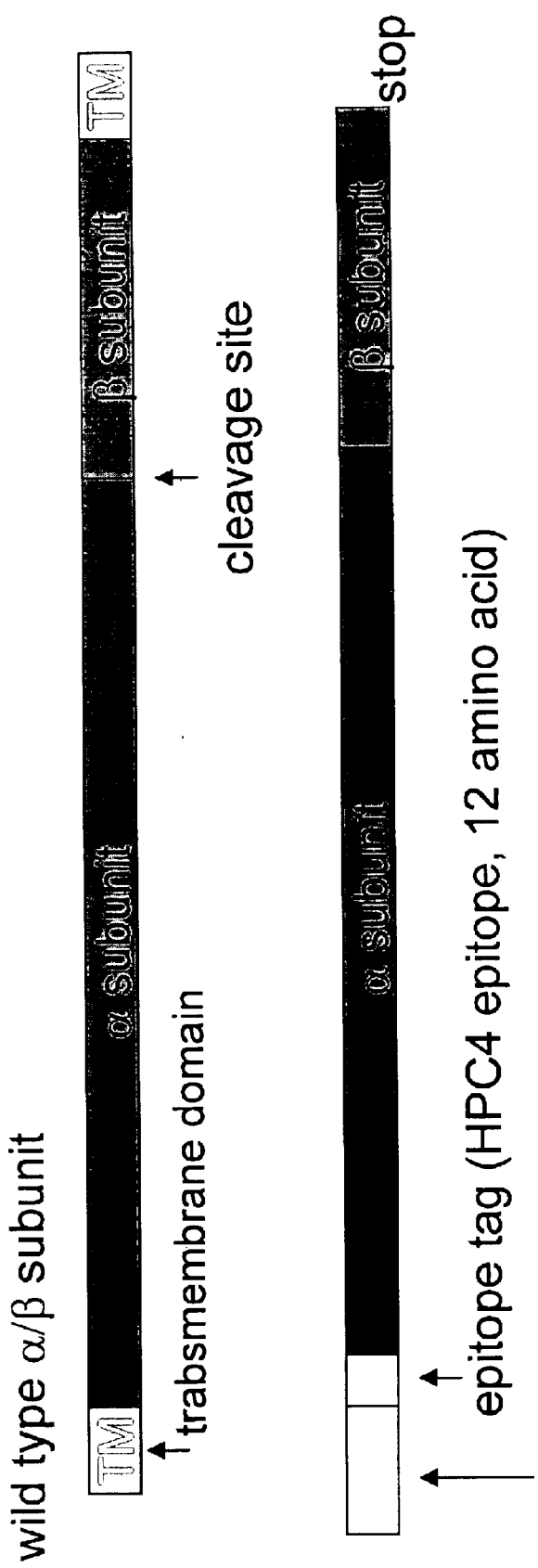
FIG. 4. Molecular engineering of GlcNAc phosphotransferase. cDNA encoding recombinant soluble human GlcNAc-phosphotransferase α/β subunits was made by replacing N-terminal and C-terminal putative transmembrane domains with a secretion signal (Ig) and a epitope tag (HPC4) and stop codon, respectively.
Figure 5:
FIG. 5. Schematic diagram for introducing proteolytic cleavage sites between the alpha and beta subunits. The junction between the alpha and beta subunits is shown (SEQ ID NO:26) and various cleavage sites are shown below (SEQ ID NOS:22–25) the junction of the cleavage sites and α/β sequence is shown in SEQ ID NOS:33,35, 37 and 38.
Figure 6A:
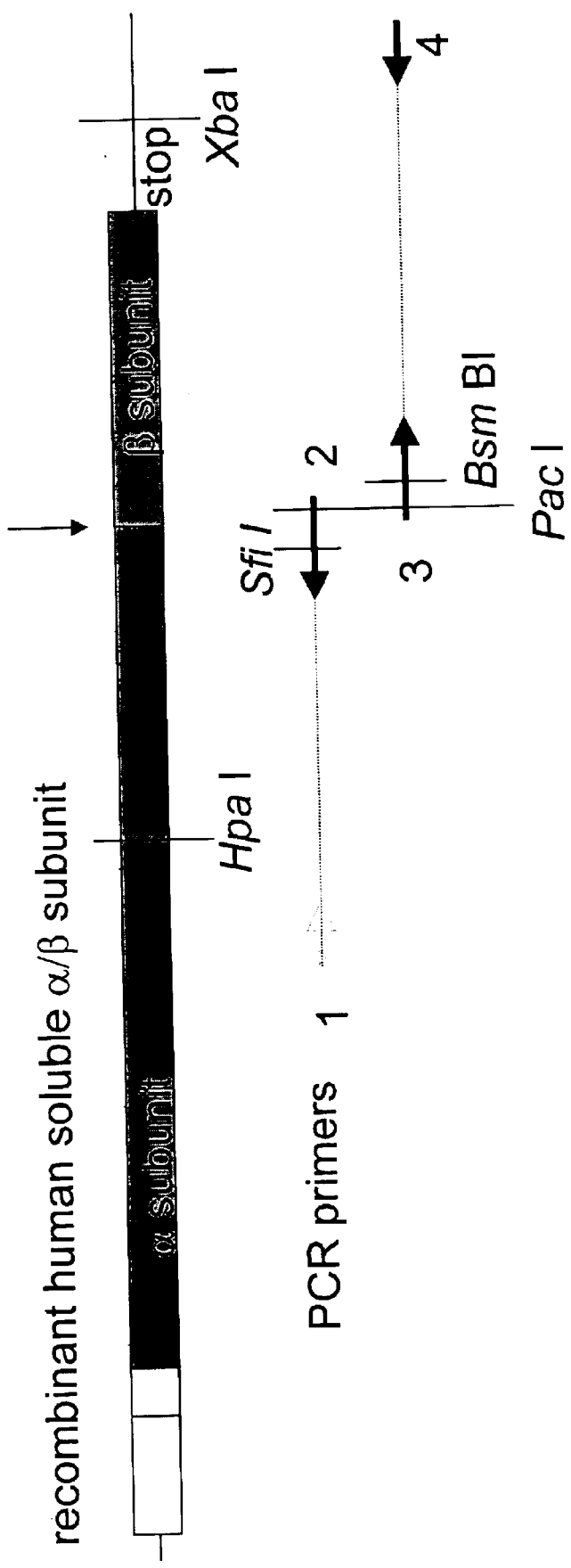
FIG. 6.(A) Schematic diagram for engineering GlcNAc-phosphotransferase. PCR products were prepared to replace the sequence between Hpa I to XbaI to introduce unique restriction enzyme sites around the α/β cleavage site. (B) Schematic and nucleotide sequence of PCR primer sits and target nucleotides. The amino acid sequence at the top of the Figure is SEQ ID NO:26 and the DNA sequence below is SEQ ID NO:27. Primers 2 and 3 have the sequences of SEQ ID NOS:28 and 29, respectively. The amino acid sequences at the bottom of the Figure are SEQ ID NOS:30 and 31 and the nucleotide sequence (+strand) is SEQ ID NO:32 and the complement of SEQ ID NO:32.(C). Overview of the introduction of protease cleavage sites into the engineered GlcNAc-phophotransferase. The sequences at the top of the Figure correspond to SEQ ID NOS:28–31 and fragments of SEQ ID NO:32 and its complement. The amino acid sequence and corresponding DNA sequence of the Factor Xa cleavage site is SEQ ID NOS:33 and 34, respectively. The amino acid sequence and corresponding DNA sequence of the Furin cleavage site is SEQ ID NOS:35 and 36, respectively. The amino acid sequence of the Enterokinase cleavage site is SEQ ID NO:37. The amino acid sequence of the Genease I cleavage site is in SEQ ID NO:38 and the wildtype amino acid sequence shown in SEQ ID NO:26. (amino acids 8–33).
Figure 6B:
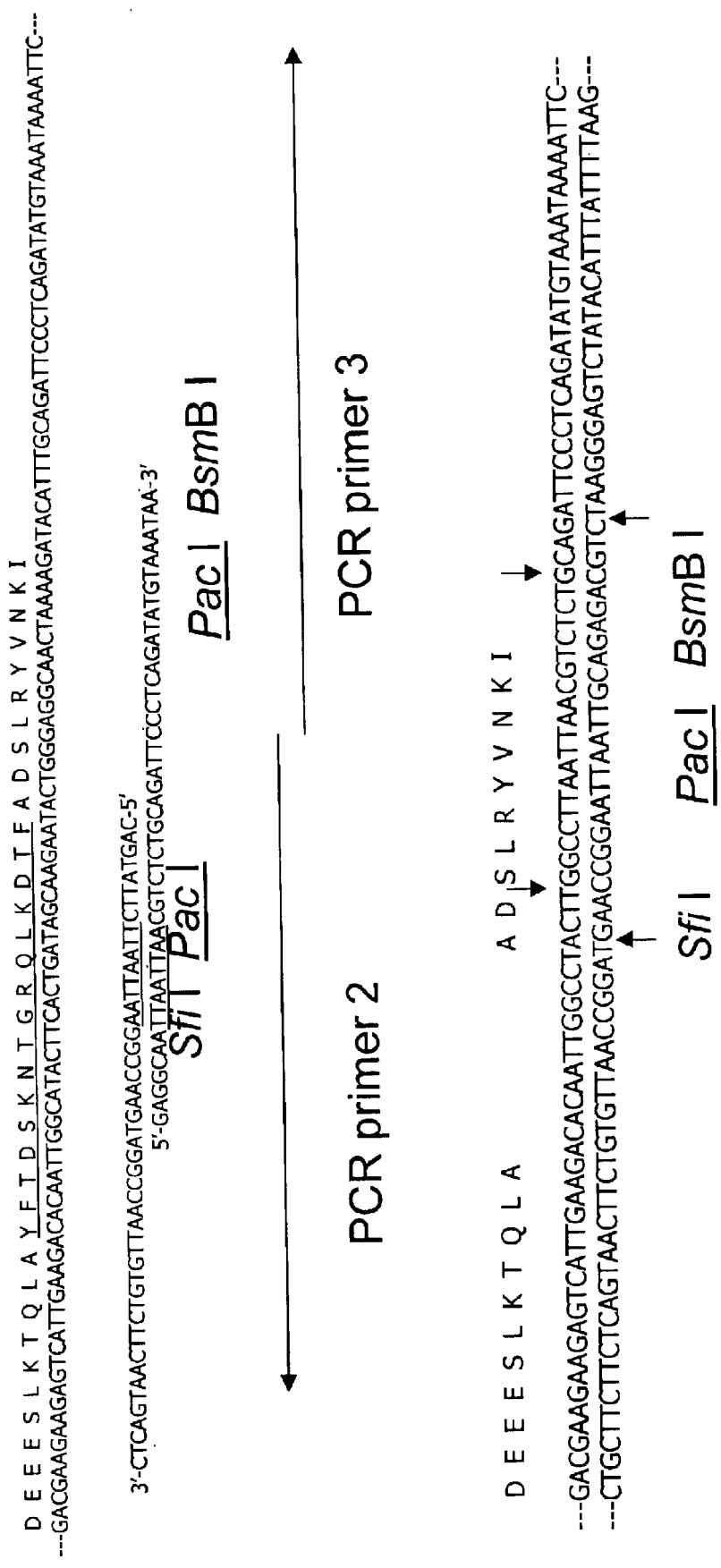
Figure 6C:
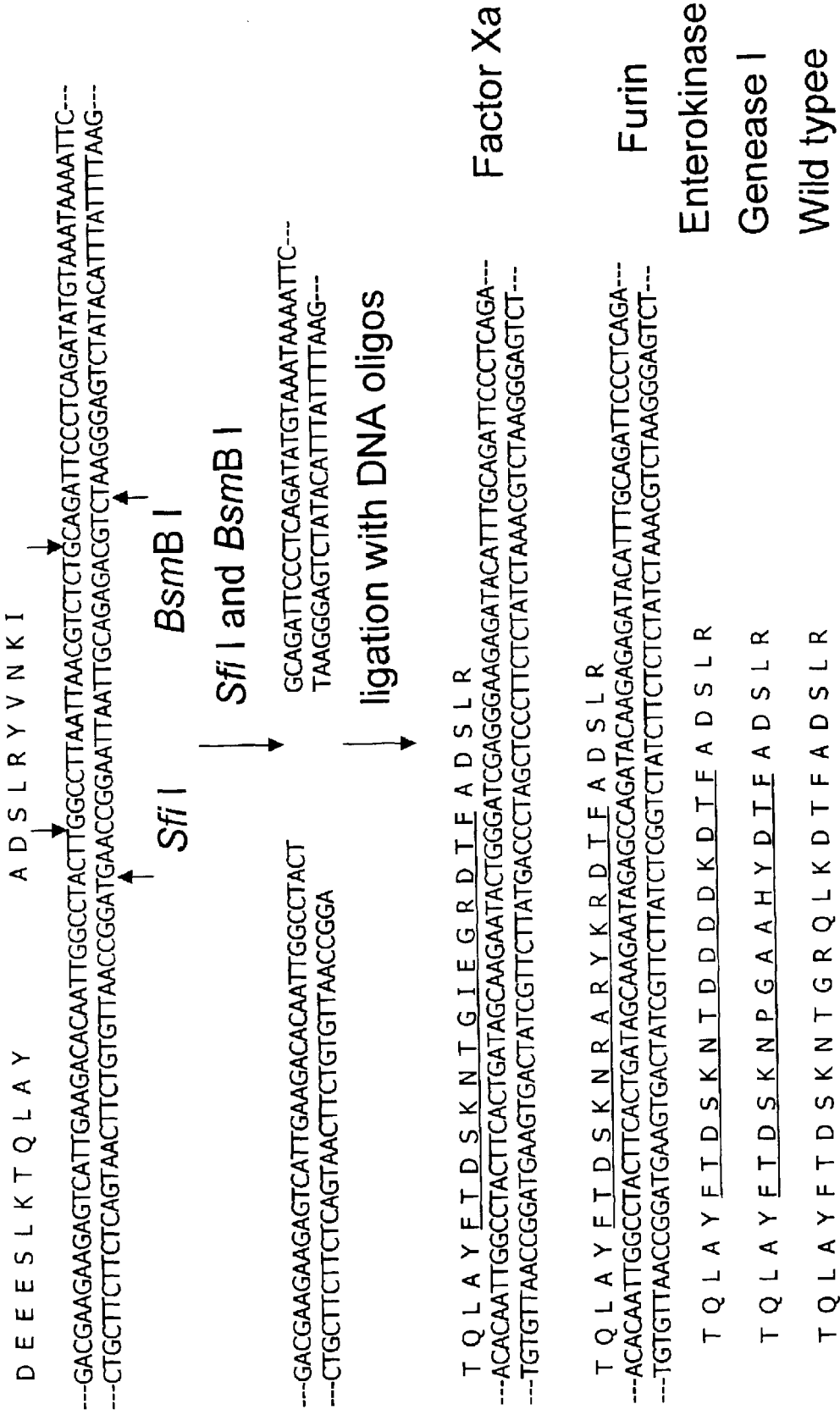

Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting. Reference is made to standard textbooks of molecular biology that contain definitions and methods and means for carrying out basic techniques, encompassed by the present invention. See, for example, Sambrook et al., Molecular Cloning: A Laboratory Manual, Third Edition, Cold Spring Harbor Laboratory Press, New York (2001), Current Protocols in Molecular Biology, Ausebel et al (eds.), John Wiley & Sons, New York (2001) and the various references cited therein.

Within the context of the present invention "Isolated" means separated out of its natural environment.

Within the context of the present invention "Polynucleotide" in general relates to polyribonucleotides and polydeoxyribonucleotides, it being possible for these to be non-modified RNA or DNA or modified RNA or DNA.

The term "GlcNAc-phosphotransferase" as used herein refers to enzymes that are capable of catalyzing the transfer of N-acetylglucosamine-1-phosphate from UDP-GlcNAc to the 6' position of 1,2-linked mannoses on lysosomal enzymes. The GlcNAc-phosphotrasferase is composed of six subunits: 2 α subunits, 2 β-subunits and 2 γ subunits. The amino acid sequence of the α subunit is shown in SEQ ID NO:4 (amino acids 1–928), the human β subunit is shown in SEQ ID NO:5 (amino acids 1–328), and the human γ subunit is shown in SEQ ID NO:7 (amino acids 25–305, signal sequence is in amino acids 1–24).

A novel soluble GlcNAc phosphotransferase has been prepared which is composed of a non-endogenous proteolytic cleavage site interposed between the α and β subunits. When combined with the γ subunit, this GlcNAc phosphotransferase exhibits high levels of activity. The soluble GlcNAc-phosphotransferase protein or polypeptide as used herein is understood to mean the sequences exemplified in this application as well as those which have substantial identity to SEQ ID NO:2. This soluble GlcNAc-phosphotransferase is missing the transmembrane domain of the non-engineered GlcNAc-phosphotransferase and has a Furin proteolytic cleavage site interposed between the α and β subunits.

The partial rat and Drosphila melanogaster α/β GlcNAc-phosphotransferase amino acid sequences are shown in SEQ ID NO:14 and 16, respectively.

Preferably, the GlcNAc-phosphotransferase polypeptides are those which are at least 70%, preferably at least 80% and more preferably at least 90% to 95% identical to the GlcNAc-phosphotransferase amino acid sequences described herein.

Polynucleotides which encode the α and β subunits of GlcNAc-phosphotransferase or soluble GlcNAc-phosphotransferase mean the sequences exemplified in this application as well as those which have substantial identity to those sequences and which encode an enzyme having the activity of the α and β subunits of GlcNAc-phosphotransferase. Preferably, such polynucleotides are those which hybridize under stringent conditions and are at least 70%, preferably at least 80% and more preferably at least 90% to 95% identical to those sequences The nucleotide sequence for the human α/β subunit precursor cDNA is shown in SEQ ID NO:3 (nucleotides 165–3932), the nucleotide sequence of the α subunit is in nucleotides 165–2948 of SEQ ID NO:3, the nucleotide sequence of the β subunit is shown in nucleotides 2949–3932 of SEQ ID NO:3, and the nucleotide sequence of the γ subunit is shown in SEQ ID NO:6 (nucleotides 25–305). The soluble GlcNAc-phosphotransferase nucleotide sequence is shown in SEQ ID NO:1. The partial rat and Drosphila melanogaster α/β GlcNAc-phosphotransferase nucleotide sequences are shown in SEQ ID NO: 13 and 15, respectively.

The term "phosphodiester α-GlcNAcase" as used herein refers to enzymes that are capable of catalyzing the removal of N-Acetylglucosamine from GlcNAc-phosphate-mannose diester modified lysosomal enzymes to generate terminal M6P.

Polynucleotides which encode phosphodiester α-GlcNAcase as used herein is understood to mean the sequences exemplified in this application as well as those which have substantial identity to SEQ ID NO:19 (murine) or SEQ ID NO:17 (human) and which encode an enzyme having the activity of phosphodiester α-GlcNAcase. Preferably, such polynucleotides are those which hybridize under stringent conditions and are at least 70%, preferably at least 80% and more preferably at least 90% to 95% identical to SEQ ID NOS:17 and/or 19.

The phosphodiester α-GlcNAcase protein or polypeptide as used herein is understood to mean the sequences exemplified in this application as well as those which have substantial identity to SEQ ID NO:20 (murine) or SEQ ID NO:18 (human). Preferably, such polypeptides are those which are at least 70%, preferably at least 80% and more preferably at least 90% to 95% identical to SEQ ID NOS:18 and/or 20.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1×to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5×to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267–284 (1984): $T_m$=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with approximately 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995).

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482–489 (1981), to find the best segment of identity or similarity between two sequences. Gap performs global alignments: all of one sequence with all of another similar sequence using the method of Needleman and Wunsch, J. Mol. Biol. 48:443–453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

Recombinant expression vectors containing a nucleic acid sequence encoding the enzymes can be prepared using well known techniques. The expression vectors include a DNA sequence operably linked to suitable transcriptional or translational regulatory nucleotide sequences such as those derived from mammalian, microbial, viral, or insect genes. Examples of regulatory sequences include transcriptional promoters, operators, enhancers, mRNA ribosomal binding sites, and appropriate sequences which control transcription and translation initiation and termination. Nucleotide sequences are "operably linked" when the regulatory sequence functionally relates to the DNA sequence for the appropriate enzyme. Thus, a promoter nucleotide sequence is operably linked to a GlcNAc-phosphotransferase DNA sequence if the promoter nucleotide sequence controls the transcription of the appropriate DNA sequence.

The ability to replicate in the desired host cells, usually conferred by an origin of replication and a selection gene by which transformants are identified, may additionally be incorporated into the expression vector.

In addition, sequences encoding appropriate signal peptides that are not naturally associated with GlcNAc-phosphotransferase can be incorporated into expression vectors. For example, a DNA sequence for a signal peptide (secretory leader) may be fused in-frame to the enzyme sequence so that the enzyme is initially translated as a fusion protein comprising the signal peptide. A signal peptide that is functional in the intended host cells enhances extracellular secretion of the appropriate polypeptide. The signal peptide may be cleaved from the polypeptide upon secretion of enzyme from the cell.

Suitable host cells for expression of the GlcNAc-phosphotransferase include prokaryotes, yeast, archae, and other eukaryotic cells. Appropriate cloning and expression vectors for use with bacterial, fungal, yeast, and mammalian cellular hosts are well known in the art, e.g., Pouwels et al. Cloning Vectors: A Laboratory Manual, Elsevier, N.Y. (1985). The vector may be a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsulated virus by well-known techniques for infection and transduction. Viral vectors may be replication competent or replication defective. In the latter case viral propagation generally will occur only in complementing host cells. Cell-free translation systems could also be employed to produce the enzymes using RNAs derived from the present DNA constructs.

Prokaryotes useful as host cells in the present invention include gram negative or gram positive organisms such as *E. coli* or *Bacilli*. In a prokaryotic host cell, a polypeptide may include a N-terminal methionine residue to facilitate expression of the recombinant polypeptide in the prokaryotic host cell. The N-terminal Met may be cleaved from the expressed recombinant GlcNAc-phosphotransferase or phosphodiester-GlcNAcase polypeptide. Promoter sequences commonly used for recombinant prokaryotic host cell expression vectors include -lactamase and the lactose promoter system.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector.

Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., Nature275:615, (1978); and Goeddel et al., Nature 281:544, (1979)), tryptophan (trp) promoter system (Goeddel et al., Nucl. Acids Res. 8:4057, (1980)), and tac promoter (Maniatis, Molecular Cloning: A Laboratory Manual, Cold Spring Harbor Laboratory, p. 412 (1982)).

Yeasts useful as host cells in the present invention include those from the genus *Saccharomyces, Pichia, K. Actinomycetes* and *Kluyveromyces*. Yeast vectors will often contain an origin of replication sequence from a 2 μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvatee decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285–195 (1991). Other suitable promoters and vectors for yeast and yeast transformation protocols are well known in the art.

Yeast transformation protocols are known to those of skill in the art. One such protocol is described by Hinnen et al., *Proceedings of the National Academy of Sciences USA*, 75:1929 (1978). The Hinnen protocol selects for Trp.sup.+ transformants in a selective medium, wherein the selective medium consists of 0.67% yeast nitrogen base, 0.5% casamino acids, 2% glucose, 10 μg/ml adenine, and 20 μg/ml uracil.

Mammalian or insect host cell culture systems well known in the art could also be employed to express recombinant GlcNAc-phosphotransferase or phosphodiester-GlcNAcase polypeptides, e.g., Baculovirus systems for production of heterologous proteins in insect cells (Luckow and Summers, Bio/Technology 6:47 (1988)) or Chinese hamster ovary (CHO) cells for mammalian expression may be used. Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

The enzymes of the present invention may, when beneficial, be expressed as a fusion protein that has the enzyme attached to a fusion segment. The fusion segment often aids in protein purification, e.g., by permitting the fusion protein to be isolated and purified by affinity chromatography. Fusion proteins can be produced by culturing a recombinant cell transformed with a fusion nucleic acid sequence that encodes a protein including the fusion segment attached to either the carboxyl and/or amino terminal end of the enzyme. Preferred fusion segments include, but are not limited to, glutathione-S-transferase, β-galactosidase, a poly-histidine segment capable of binding to a divalent metal ion, and maltose binding protein. In addition, the HPC-4 epitope purification system may be employed to facilitate purification of the enzymes of the present invention. The HPC-4 system is described in U.S. Pat. No. 5,202,253, the relevant disclosure of which is herein incorporated by reference.

According to the present invention, isolated and purified GlcNAc-phosphotransferase enzymes may be produced by the recombinant expression systems described above. The method comprises culturing a host cell transformed with an expression vector comprising a DNA sequence that encodes the enzyme under conditions sufficient to promote expression of the enzyme. The enzyme is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium. When expression systems that secrete the recombinant protein are employed, the culture medium first may be concentrated. Following the concentration step, the concentrate can be applied to a purification matrix such as a gel filtration medium. Alternatively, an anion exchange resin can be employed, e.g., a matrix or substrate having pendant diethylaminoethyl (DEAE) groups. The matrices can be acrylamide, agarose, dextran, cellulose, or other types commonly employed in protein purification. Also, a cation exchange step can be employed. Suitable cation exchangers include various insoluble matrices comprising sulfopropyl or carboxymethyl groups. Further, one or more reversed-phase high performance liquid chromatography (RP-HPLC) steps employing hydrophobic RP-HPLC media (e.g., silica gel having pendant methyl or other aliphatic groups) can be employed to further purify the enzyme. Some or all of the foregoing purification steps, in various combinations, are well known in the art and can be employed to provide an isolated and purified recombinant protein.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification, or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

The GlcNAc phosphotransferase α and β subunits are encoded by a single mRNA. The natural GlcNAc-phosphotransferase consists of a transmembrane domain and a proteolytic cleavage site, which is employed during post-translational processing to separate the α and β polypeptides. Genetic manipulation of the GlcNAc-phosphotransferase coding sequence to remove the transmembrane domain yields a α and β polyprotein, which is soluble and more easily recoverable when the coding sequence is expressed in a culture system.

The soluble GlcNAc-phosphotransferase α and β polyprotein can be further engineered to remove the endogenous or natural proteolytic cleavage site. As used herein "endogenouse or natural proteolytic cleavage site" means the cleavage site, which is found in the naturally occurring wildtype GlcNAc-phosphotransferase α and β protein, and which is encoded from the corresponding gene or nucleotide sequence. Preferably, following removal or concurrent with the removal the proteolytic cleavage site is replaced with a non-natural or non-endogenous proteolytic cleavage site is inserted between the α and β subunits. This proteolytic site should catalyze the cleavage of a peptide bond in a site determinative manner. Examples of such non-natural proteolytic cleavage sites include Furin, Factor Xa, Enterokinase, and Genease (SEQ ID NOS:22–25).

The soluble GlcNAc-phosphotransferease engineered to contain a non-natural proteolytic site can then been subjected to the corresponding protease to cleave the αβ polyprotein at the proteolytic site yielding separate α and β GlcNAc-phosphotransferase subunits. The GlcNAc-phosphotransferase α and β polyprotein can be cleaved either in vitro or in vivo. In vitro proteolysis includes containing either crude, preferably partially purified, and more preferably purified, GlcNAc-phosphotransferase polyprotein and then subjecting the GlcNAc phosphotransferase poloyprotein to proteolysis reactions, these reactions conditions will vary depending on the enzyme used and concentration of the protein and proteolytic enzyme.

In vivo proteolysis includes overexpressing the gene encoding the protease with the soluble GlcNAc-phosphotransferase in a cell and then isolating the separated α and β subunits. The coexpression can be performed by cotransfection of the genes, transfection of the soluble GlcNAc-phosphotransferase polynucleotide followed by the transfection of the protease, transfection of the soluble GlcNAc phosphotransferase into a cell that stably expresses the protease or transfecting the protease into a cell, which stably expresses the soluble GlcNAc-phosphotransferase. Alternatively, the soluble GlcNAc-phosphotransferase can be expressed in a cell, which has a natural or endogenous protease present in the cell, and use that protease to achieve proteolytic cleavage.

The invention also provides methods of phosphorylating a protein with the soluble GlcNAc-phosphotransferase α and β subunits alone or in combination with the γ subunit. Additionally, the phosphorylated proteins may subsequently be treated with phosphodiester α-GlcNAcase. The GlcNAc-phosphotransferase soluble or non-soluble, containing only the α and β subunits or all of α, β and γ can be assayed for activity in the same manner. For example, the GlcNAc-phosphotransferase can be measured by assessing the ability to transfer GlcNAc phosphate to α-methylmannosidase per hour in a reaction containing UDP-GlcNAc and α-methylmannoside.

In one embodiment of the present invention, the phosphorylated proteins are lysosomal enzymes that utilize the M6P transport system and thus obtainphosphorylated lysosomal enzymes. Lysosomal hydrolases are produced by treating the high mannose hydrolases with GlcNAc-phosphotransferase which catalyzes the transfer of N-acetylglucosamine-1-phosphate from UDP-GlcNAc to the 6' position of 1,2-linked or other mannoses on the hydrolase.

Examples of such lysosomal enzymes (and diseases linked to their deficiency) include α-glucosidase (Pompe Disease), α-L-iduronidase (Hurler Syndrome), α-galactosidase A (Fabry Disease), arylsulfatase (Maroteaux-Lamy Syndrome), N-acetylgalactosamine-6-sulfatase or β-galactosidase (Morquio Syndrome), iduronate 2-sulfatase (Hunter Syndrome), ceramidase (Farber Disease), galactocerebrosidase (Krabbe Disease), β-glucuronidase (Sly Syndrome), Heparan N-sulfatase (Sanfilippo A), N-Acetyl-α-glucosaminidase (Sanfilippo B), Acetyl CoA-α-glucosaminide N-acetyl transferase, N-acetyl-glucosamine-6 sulfatase (Sanfilippo D), Galactose 6-sulfatase (Morquio A), Arylsulfatase A, B, and C (Multiple Sulfatase Deficiency), Arylsulfatase A Cerebroside (Metachromatic Leukodystrophy), Ganglioside (Mucolipidosis IV), Acid β-galactosidase $G_{M1}$ Galglioside ($G_{M1}$ Gangliosidosis), Acid β-galactosidase (Galactosialidosis), Hexosaminidase A (Tay-Sachs and Variants), Hexosaminidase B (Sandhoff), α-fucosidase (Fucsidosis), α-N-Acetyl galactosaminidase (Schindler Disease), Glycoprotein Neuraminidase (Sialidosis), Aspartylglucosamine amidase (Aspartylglucosaminuria), Acid Lipase (Wolman Disease), Acid Ceramidase (Farber Lipogranulomatosis), Lysosomal Sphingomyelinase and other Sphingomyelinase (Nieman-Pick).

In another embodiment of the invention, the lysosomal hydrolase glucocerbrosidase whose deficiency is the causative agent of Gaucher's disease may be subject to phosphorylation with the soluble GlcNAc phosphotransferase α and β subunits alone. This modified GBA may then be treated with phosphodiester α-GlcNAcase to complete the modification of the GBA thereby making the enzyme available for targeting tissues via the M6P receptor. This modified GBA has been found to bind to the mannose receptor with high affinity resulting in an increased bioavailablity of the enzyme compared to the current GBA employed in therapeutic protocols, particularly in lung and bone tissues.

Methods for treating lysosomal enzymes with the enzymes of the present invention are within the skill of the artisan. Generally, the lysosomal enzymes is at a concentration of about 10 mg/ml and GlcNAc-phosphotransferase is present in a concentration of about 1 to about 10 million units per milliliter. The enzymes are incubated at about 20° C. for about 48 hours or longer in the presence of a buffer that maintains the pH at about 6–7 and any stabilizers or coenzymes required to facilitate the reaction. Then, phosphodiester α-GlcNAcase can be added to the system to a concentration of about 250,000 to 100,000 units/mL and the system is allowed to incubate for about 6 or more hours. The modified lysosomal enzymes having highly phosphorylated oligosaccharides is then recovered by conventional means.

In a preferred embodiment, the lysosomal hydrolase at 10 mg/ml is incubated in 50 mm Sodium Acetate pH 6.5, 20 mM $MnCl_2$, 0.3 mM (300 μM) with GlcNAc phosphotransferase at 1 to 10 million units/ml at 20° C. for 48 hours or longer,. The GBA is then treated with phosphodiester-α GlcNAcase for 6 hours. The modified enzyme is then repurified by conventional chromatography.

In a further aspect, the present invention provides a method for the treatment of lysosomal storage diseases by administering a disease treating amount of the highly phosphorylated lysosomal hydrolases of the present invention to a patient suffering from the corresponding lysosomal storage disease. While dosages may vary depending on the disease and the patient, the enzyme is generally administered to the patient in amounts of from about 0.1 to about 1000 milligrams per kg of patient per month, preferably from about 1 to about 500 milligrams per kg of patient per month. The highly phosphorylated Genzymes of the present invention are more efficiently taken into the cell and the lysosome than the naturally occurring or less phosphorylated enzymes and are therefore effective for the treatment of the disease. Within each disease, the severity and the age at which the disease presents may be a function of the amount of residual lysosomal enzyme that exists in the patient. As such, the present method of treating lysosomal storage diseases includes providing the highly phosphorylated lysosomal hydrolases at any or all stages of disease progression.

The lysosomal enzyme is administered by any convenient means. For example, the enzyme can be administered in the form of a pharmaceutical composition containing the enzyme and any pharmaceutically acceptable carriers or by means of a delivery system such as a liposome or a controlled release pharmaceutical composition. The term "pharmaceutically acceptable" refers to molecules and compositions that are physiologically tolerable and do not typically produce an allergic or similar unwanted reaction such as gastric upset or dizziness when administered. Preferably, "pharmaceutically acceptable" means approved by a regulatory agency of the Federal or a state government or listed in the U.S. Pharmacopoeia or other generally recognized pharmacopoeia for use in animals, preferably humans. The term "carrier" refers to a diluent, adjuvant, excipient, or vehicle with which the compound is administered. Such pharmaceutical carriers can be sterile liquids, such as saline solutions, dextrose solutions, glycerol solutions, water and oils emulsions such as those made with oils of petroleum, animal, vegetable, or synthetic origin (peanut oil, soybean oil, mineral oil, or sesame oil). Water, saline solutions, dextrose solutions, and glycerol solutions are preferably employed as carriers, particularly for injectable solutions.

The enzyme or the composition can be administered by any standard technique compatible with enzymes or their compositions. For example, the enzyme or composition can be administered parenterally, transdermally, or transmucosally, e.g., orally or nasally. Preferably, the enzyme or composition is administered by intravenous injection.

The following Examples provide an illustration of embodiments of the invention and should not be construed to limit the scope of the invention, which is set forth in the appended claims. In the following Examples, all methods described are conventional unless other wise specified.

Figure 7:
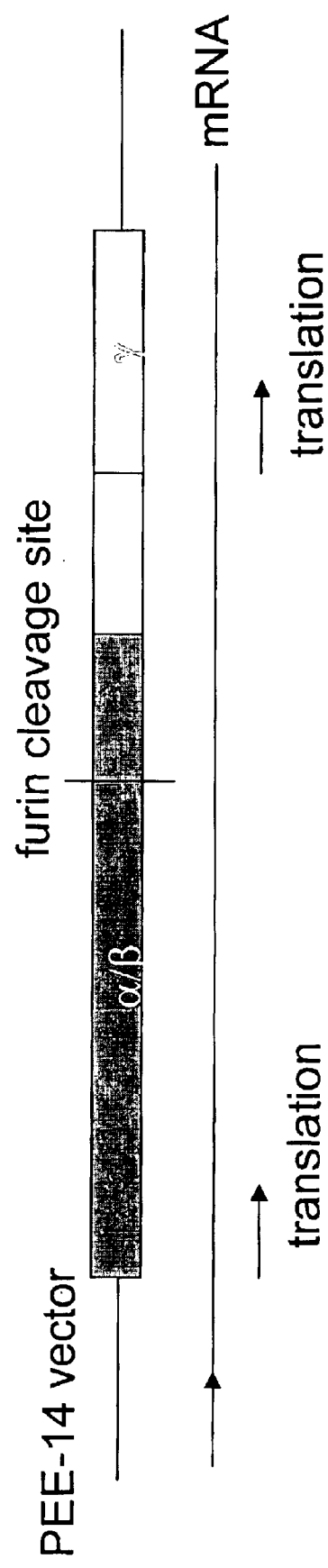
FIG. 7. Schematic overview of the expression of α/β/γ GlcNAc phosphotransferase on a single mRNA molecule and translated employing an Internal Ribosome Entry Sequence (IRES).

EXAMPLES
Materials and Methods
Construction of the Furin-cleavage site containing α/β subunit of GlcNAc-phosphotransferase—The molecular cloning and expression of wild type human UDP-N-acetylglucosamine: lysosomal-enzyme-N-acetylglucosamine-1-phosphotransferase (GlcNAc-phosphotransferase) is described in U.S. Ser. No. 09/636,060 and PCT/US00/21970, incorporated herein by reference. Also, the construction and expression of recombinant soluble human UDP-N-acetylglucosamine: lysosomal-enzyme-N-acetylglucosamine-1-phosphotransferase (GlcNAc-phosphotransferase) is described in U.S. Ser. No. 09/636,060 and PCT/US00/21970, incorporated herein by reference. The soluble GlcNAc-phosphotransferase α/β subunit cDNA was contained within the Nhe I and Xba I site of pcDNA 6/V5/His-A (Invitrogen). This plasmid, designated, pMK 52 was used as the starting material for the construction of the furin-cleavage site containing α/β subunit of recombinant soluble GlcNAc-phosphotransferase as shown in FIG. 7.

In order to construct the furin-cleavage site containing α/β subunit of recombinant soluble GlcNAc-phosphotransferase, an intermediate plasmid was constructed to provide the necessary restriction sites for cloning. The intermediate plasmid, designated as pPW6, was constructed by replacing DNA sequence between Hpa I site to Xba I site with DNA fragments prepared by PCR. This replacement generated novel and unique Sfi I and Bsm BI restriction sites which was used to introduce furin specific cleavage site between α and β subunits . Then the sequence between unique Sfi I and Bsm BI restriction sites was replaced with synthetic oligo nucleotides which code amino acid sequence for furin-cleavage sequence. The plasmid thus made was designated pPW 9. PPW 9 was used for transient expression of α/β subunit in 293 T cells. PPW9 was also used as a starting material to make bi-cistronic vectors expressing α/β and γ subunit of GlcNAc-phosphotransferase (see below). PPW9 was also used to make a plasmid for stable expression using pEE14 and pEE14.1 (Lonza Biologics).

Construction of the bi-cistronic expression vector which express Furin-cleavage site containing α/β subunit and wild type γ subunit of GlcNAc-phosphotransferase—To express both α/β subunit and γ subunit from one vector, the bi-cistronic vector pIRES (Clontech) was used. pIRES has internal ribosome entry sequence between two multiple cloning site, therefore two polypeptides are translated from single mRNA. Nhe I-Xba I fragment of pPW9 which encode furin cleavage site containing α/β subunit was subcloned into Nhe I site of multiple cloning site A of pIRES. Nhe I-Xba I fragment of pMK 17 which encode wild type γ subunit was subcloned into Xba I site of multiple cloning site B of pIRES. The plasmid thus made was designated pMK 158 and used for transient expresssion of GlcNAc-phosphotransferase in 293 T cells. To prepare bi-cistronic vector which has pEE14 as a back bone, Nhe I-XbaI fragment of pMK 158 was subcloned into the XbaI site of pEE14 and the plasmid thus made was designated pMK 163.

The plasmid pMK 155, expressing α/β was constructed as follows. A Nhe I-Xba I fragement from pPW9 was sucloned into the XbaI site of pEE14 to prepare a plasmid for stable expression of the α/β GlcNAc-phosphotransferase. The plasmid pMK193 was constructed to express α/β and γ subunits using two promoters rather than the IRES element. The Nhe I-Xba I fragement from pPW9 was sucloned into the XbaI site of pEE6.1 (Lonza Biologics) and the cDNA for the γ subunit was subcloned into the EcoRI site of pEE 14.1 (Lonza Biologics). These two plasmids were combined together following the manufacturer's instructions to yield a plasmid that expresses α/β and γ subunits from a single plasmid using two CMV promoters.

Transient Expression of Recombinant human GlcNAc-phosphostransferase Enzyme—The plasmid pMK 158 encoding α/β (furin-cleavage site containing) and subunit of recombinant soluble human GlcNAc-phosphotransferase was initially tested in a mammalian cell culture system using 293T cells for transient protein expression. The transfection of pMK158 into 293T cells was performed using the FUGENE-6 Transfection reagent (Roche) according to the manufacturer's protocol. Briefly, 293T cells were plated in 10-cm dishes at approximately 50% confluency in 10 ml of Dulbecco's Modified Eagle's Medium (DMEM) supplemented with 10% (v/v) fetal bovine serum (FBS). Subsequently, 6 µg of pMK158 was transfected with 18 µl of the FUGENE-6 reagent and the culture was incubated at 37° C. for three days in a 5% $CO_2$ atmosphere. The media was assayed for GlcNAc-phosphotransferase activity by measuring the transfer of GlcNAc-[$^{32}$P] from the synthetic substrate [$^{32}$P]-UDP-GlcNAc to α-methylmannoside to produce GlcNAc-[32P]monophosphate-methylmannoside. The medium from the transfected cells was shown to contain active GlcNAc-phosphotransferase and plasmid pMK163 which has same coding sequence with pMK 158 was then used for the stable expression of r GlcNAc-phosphotransferase. Cleavage of the α/β protein in vivo was confirmed by SDS-PAGE to compare the size of HPC4 tagged protein, which is the α subunit.

Stable Expression of Recombinant Human GlcNAc-phosphotransferase

Stable cell lines were made according to the manufacturer's instructions using the pMK 163, 155 and 193 plasmids described above.

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polypeptide comprising SEQ ID NO:2.

2. An N-acetylglycosamine-1-phosphotransferase (GlcNAc-phosphotransferase) comprising an α subunit, a β subunit and a site-specific proteolytic cleavage site interposed between said α and β subunits, wherein said site-specific proteolytic cleavage site is not endogenous to GlcNAc-phosphotransferase, wherein said α subunit is encoded by nucleotides 165 to 2948 of SEQ ID NO:3, or a sequence that hybridizes under stringent conditions to the complement of nucleotides 165 to 2948 of SEQ ID NO:3, wherein said stringent conditions comprise hybridization in 50% formamide, 1M NaCl, 1% SDS at 37° C. and washing in 0.1×SSC at 65° C. and which encodes a protein when combined with a β subunit protein encoded by nucleotides 2949 to 2932 of SEQ ID NO:3 has GlcNAc-phosphotransferase activity; and wherein said β-subunit is encoded by nucleotides 2949 to 3932 of SEQ ID NO:3, or a sequence that hybridizes under stringent conditions to the complement of nucleotides 2949 to 3932 of SEQ ID NO:3, wherein said stringent conditions comprise hybridization in 50% formamide, 1M NaCl, 1% SDS at 37° C. and washing in 0.1×SSC at 65° C. and which encodes a protein when combined with an α subunit protein encoded by nucleotides 165 to 2948 of SEQ ID NO:3 has GlcNAc-phosphotransferase activity.

3. The GlcNAc-phosphotransferase of claim 2, wherein said α-subunit comprises amino acids 1–928 of SEQ ID NO:4.

4. The GlcNAc-phosphotransferase of claim 2, wherein said β subunit comprises amino acids 1 to 328 of SEQ ID NO:5.

5. The GlcNAc-phosphotransferase of claim 2, wherein said GlcNAc-phosphotransferase further comprises a γ subunit.

6. The GlcNAc-phosphotransferase of claim 5, wherein said γ subunit comprises the amino acid sequence of SEQ ID NO:7.

7. The GlcNAc-phosphotransferase of claim 2, wherein said site-specific proteolytic cleavage site is selected from the group consisting of a Furin proteolytic cleavage site, a Factor Xa proteolytic cleavage site, a Enterokinase proteolytic cleavage site, and a proteolytic cleavage site comprising SEQ ID NO:25.

8. The GlcNAc-phosphotransferase of claim 7, wherein said site-specific proteolytic cleavage site is a Furin proteolytic cleavage site.

9. The GlcNAc-phosphotransferase of claim 8, wherein said Furin proteolyfic cleavage site comprises SEQ ID NO:24.

10. A method of phosphorylating a lysosomal hydrolase protein comprising an asparagine-linked oligosaccharide with a high mannose structure, the method comprising contacting said lysosomal hydrolase protein with the isolated polypeptide of claim 1 for a time and under conditions suitable to produce a phosphorylated lysosomal hydrolase protein.

11. The method of claim 10, wherein said lysosomal hydrolase protein is selected from the group consisting of α-glucosidase, α-L-iduronidase, α-galactosidase A, arylsulfatase, N-acetlygalactosamine-α-sulfatase, β-galactosidase, iduronate 2-sulfatase, ceramidase, galactocerebrosidase, β-glucoronidase, Heparan N-sulfatase, N-Acetyl-α-glucosaminidase, N-acetyl-glucosamine-6 sulfatase, Galactose 6-sulfatase, Arylsulfatase A, Arylsulfatase B, Arylsulfatase C, Ganglioside sialidase, Acid β-galactosidase, Hexosaminidase A, Hexosaminidase B, α-fucosidase, α-N-Acetyl galactosaminidase, Glycoprotein Neuraminidase, Aspartylgucosamine amidase, Acid Lipase, Acid Ceramidase, Sphingomyelinase, and Glucocerebrosidase.

12. The method of claim 10, further comprising contacting said phosphoryalated protein with an isolated N-acetylglucosamine-1-phosphodiester-N-Acetyglucosaminidase (phosphodiester α-GlcNAcase).

13. The method of claim 12, wherein said phosphodiester α-GlcNAcase comprises the amino acid sequence of SEQ ID NO:18.

14. The method of claim 12, wherein said phosphodiester α-GlcNAcase is encoded by a nucleotide sequence comprising SEQ ID NO:17 or a nucleotide sequence that hybridizes under stringent conditions to the complement of SEQ ID NO:17, wherein said stringent conditions comprise hybridization in 50% formamide, 1M NaCl, 1% SDS at 37° C. and washing in 0.1×SSC at 65° C., and which encodes a protein with phosphodiester α-GlcNAcase activity.

15. The method of claim 10, wherein prior to said contacting the method comprises: culturing a host cell which comprises a polynucleotide encoding the polypeptide for a time under conditions suitable for expression of the polypeptide; and isolating said polypeptide.

16. A method of phosphorylating a lysosomal hydrolase protein comprising an asparagine-linked oligosaccharide with a high mannose structure, the method comprising contacting said protein with the GlcNAc phosphotransferase of claim 2 for a time and under conditions suitable to produce a phosphorylated protein.

17. The method of claim 16, wherein said α-subunit comprises amino acids 1–928 of SEQ ID NO:4.

18. The method of claim 16, wherein said β subunit comprises amino acids 1 to 328 of SEQ ID NO:5.

19. The method of claim 16, wherein said GlcNAc-phosphotransferase further comprises a γ subunit.

20. The method of claim 19, wherein said γ subunit is encoded by SEQ ID NO:6, or a nucleotide sequence that hybridizes under stringent conditions to the complement of SEQ ID NO:6, wherein said stringent conditions comprise hybridization in 50% formamide, 1M NaCl, 1% SDS at 37° C. and washing in 0.1×SSC at 65° C.

21. The method of claim 19, wherein said γ subunit comprises the amino acid sequence of SEQ ID NO:7.

22. The method of claim 16, wherein said site-specific proteolytic cleavage site is selected from the group consisting of a Furin proteolytic cleavage site, a Factor Xa proteolytic cleavage site, a Enterokinase proteolytic cleavage site, and a proteolytic cleavage site comprising SEQ ID NO:25.

23. The method of claim 22, wherein said site-specific proteolytic cleavage site is a Furin proteolytic cleavage site.

24. The method of claim 23, wherein said Furin proteolytic cleavage site comprises SEQ ID NO:24.

25. The method of claim 16, wherein said lysosomal hydrolase protein is selected from the group consisting of α-glucosidase, α-L-iduronidase, α-galactosidase A, arylsulfatase, N-acetlygalactosamine-α-sulfatase, β-galactosidase, iduronate 2-sulfatase, ceramidase, galactocerebrosidase, β-glucoronidase, Heparan N-sulfatase, N-Acetyl-α-glucosaminidase, N-acetyl-glucosamine-6 sulfatase, Galactose 6-sulfatase, Arylsulfatase A, Arylsulfatase B, Arylsulfatase C, Ganglioside sialidase, Acid β-galactosidase Hexosaminidase A, Hexosaminidase B, α-fucosidase, α-N-Acetyl galactosaminidase, Glycoprotein Neuraminidase, Aspartyl-glucosamine amidase, Acid Lipase, Acid Ceramidase, Sphingomyelinase, and Glucocerebrosidase.

26. The method of claim 16, further comprising contacting said phosphoryalated protein with an isolated phosphodiester α-GlcNAcase.

27. The method of claim 26, wherein said phosphodiester α-GlcNAcase comprises the amino acid sequence of SEQ ID NO:18.

28. The method of claim 26, wherein said phosphodiester α-GlcNAcase is encoded by a nucleotide sequence comprising SEQ ID NO:17 or a nucleotide sequence that hybridizes under stringent conditions to the complement of SEQ ID NO:17, wherein said stringent conditions comprise hybridization in 50% formamide, 1M NaCl, 1% SDS at 37° C. and washing in 0.1×SSC at 65° C.

29. The method of claim 16, wherein prior to said contacting the method comprises: culturing a host cell which comprises a polynucleotide encoding the GlcNAc-phosphotransferase for a time under conditions suitable for expression of the GlcNAc-phosphotransferase; and isolating said GlcNAc-phosphotransferase.

* * * * *